(12) United States Patent
Overmyer et al.

(10) Patent No.: US 12,396,724 B2
(45) Date of Patent: Aug. 26, 2025

(54) SURGICAL INSTRUMENT WITH MULTIPLE INTERFACE CONFIGURATIONS

(71) Applicant: CILAG GMBH INTERNATIONAL, Zug (CH)

(72) Inventors: Mark D. Overmyer, Cincinnati, OH (US); Brett E. Swensgard, West Chester, OH (US); Shane R. Adams, Lebanon, OH (US); Thomas W. Lytle, IV, Liberty Township, OH (US); Richard L. Leimbach, Cincinnati, OH (US); Frederick E. Shelton, IV, Hillsboro, OH (US); Kevin L. Houser, Springsboro, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/644,295

(22) Filed: Apr. 24, 2024

(65) Prior Publication Data
US 2024/0307058 A1   Sep. 19, 2024

Related U.S. Application Data

(63) Continuation of application No. 17/590,525, filed on Feb. 1, 2022, now Pat. No. 12,023,023, which is a
(Continued)

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 34/25* (2016.02);
(Continued)

(58) Field of Classification Search
CPC ..... A61B 17/068; A61B 17/072; A61B 34/25; A61B 90/98; G16H 10/60; G16H 40/63; G05B 19/05
See application file for complete search history.

(56) References Cited

U.S. PATENT DOCUMENTS 5,769,791 A   6/1998   Benaron
6,211,626 B1  4/2001   Lys
(Continued)

FOREIGN PATENT DOCUMENTS

CN   102188269 A1   9/2011
CN   103118615 A    5/2013
(Continued)

*Primary Examiner* — Nathaniel C Chukwurah
(74) *Attorney, Agent, or Firm* — Troutman Pepper Locke LLP

(57) ABSTRACT

A surgical instrument includes a handle assembly, an elongate shaft, an end effector, and control system having a processor and a memory. The handle assembly is movable between a plurality of positions and includes an interface. The control system can cause the processor to toggle between a plurality of interface configurations each associated with one of the positions of the handle assembly. Additionally, or alternatively, the control system can toggle the interface between a primary interface configuration with operational controls and a secondary interface configuration with navigation controls. Additionally, or alternatively, the interface can include a touchscreen configured to provide a firing input signal to the processor. Additionally, or alternatively, a surgical assembly can include the surgical instrument and a remote operating unit with a secondary interface configured to control the end effector.

16 Claims, 38 Drawing Sheets

Related U.S. Application Data continuation of application No. 16/585,883, filed on Sep. 27, 2019, now Pat. No. 11,259,799, which is a continuation of application No. 16/164,094, filed on Oct. 18, 2018, now Pat. No. 10,898,185, which is a continuation of application No. 15/459,515, filed on Mar. 15, 2017, now Pat. No. 10,588,626, which is a continuation of application No. 14/226,126, filed on Mar. 26, 2014, now Pat. No. 10,004,497.

(51) Int. Cl.
| | | |
|---|---|---|
| *A61B 34/00* | (2016.01) | |
| *A61B 90/98* | (2016.01) | |
| *G05B 19/05* | (2006.01) | |
| *G16H 10/60* | (2018.01) | |
| *G16H 40/63* | (2018.01) | |
| *A61B 17/00* | (2006.01) | |
| *A61B 17/29* | (2006.01) | |
| *A61B 90/00* | (2016.01) | |
| *G16H 20/40* | (2018.01) | |

(52) U.S. Cl.
CPC .............. *A61B 90/98* (2016.02); *G05B 19/05* (2013.01); *G16H 10/60* (2018.01); *G16H 40/63* (2018.01); *A61B 2017/00017* (2013.01); *A61B 2017/00115* (2013.01); *A61B 2017/00199* (2013.01); *A61B 2017/00212* (2013.01); *A61B 2017/00221* (2013.01); *A61B 2017/00225* (2013.01); *A61B 2017/00398* (2013.01); *A61B 2017/0046* (2013.01); *A61B 2017/00482* (2013.01); *A61B 2017/2927* (2013.01); *A61B 2090/0805* (2016.02); *A61B 2090/0807* (2016.02); *A61B 2090/0808* (2016.02); *A61B 2090/0811* (2016.02); *G05B 2219/14018* (2013.01); *G16H 20/40* (2018.01); *Y10T 29/49826* (2015.01)

(56) References Cited

U.S. PATENT DOCUMENTS

| | | | |
|---|---|---|---|
| 8,161,977 | B2 | 4/2012 | Shelton, IV |
| 10,004,497 | B2 | 6/2018 | Overmyer |
| 2002/0077565 | A1 | 6/2002 | Burdorff |
| 2004/0114034 | A1 | 6/2004 | Squilla |
| 2006/0282064 | A1 | 12/2006 | Shimizu |
| 2007/0085496 | A1 | 4/2007 | Philipp |
| 2009/0090763 | A1* | 4/2009 | Zemlok ............ A61B 17/07207 227/175.2 |
| 2009/0289096 | A1* | 11/2009 | Shelton, IV ..... A61B 17/07207 227/180.1 |
| 2010/0256624 | A1 | 10/2010 | Brannan |
| 2011/0017801 | A1 | 1/2011 | Zemlok |
| 2011/0082486 | A1 | 4/2011 | Messerly |
| 2011/0121049 | A1 | 5/2011 | Malinouskas |
| 2011/0204119 | A1 | 8/2011 | McCuen |
| 2012/0071796 | A1 | 3/2012 | Smith |
| 2012/0138658 | A1 | 6/2012 | Ullrich |
| 2012/0223121 | A1 | 9/2012 | Viola |
| 2013/0206814 | A1 | 8/2013 | Morgan |

FOREIGN PATENT DOCUMENTS

| | | |
|---|---|---|
| EP | 1915957 A2 | 4/2008 |
| EP | 2044890 A1 | 8/2009 |
| EP | 2486860 A2 | 8/2012 |
| JP | 2008253496 A | 10/2008 |
| JP | 2012166018 A | 9/2012 |
| WO | 1997041767 A2 | 11/1997 |
| WO | 2010104753 A1 | 9/2010 |
| WO | 2012015795 A1 | 2/2012 |
| WO | 2012109760 A1 | 8/2012 |

\* cited by examiner

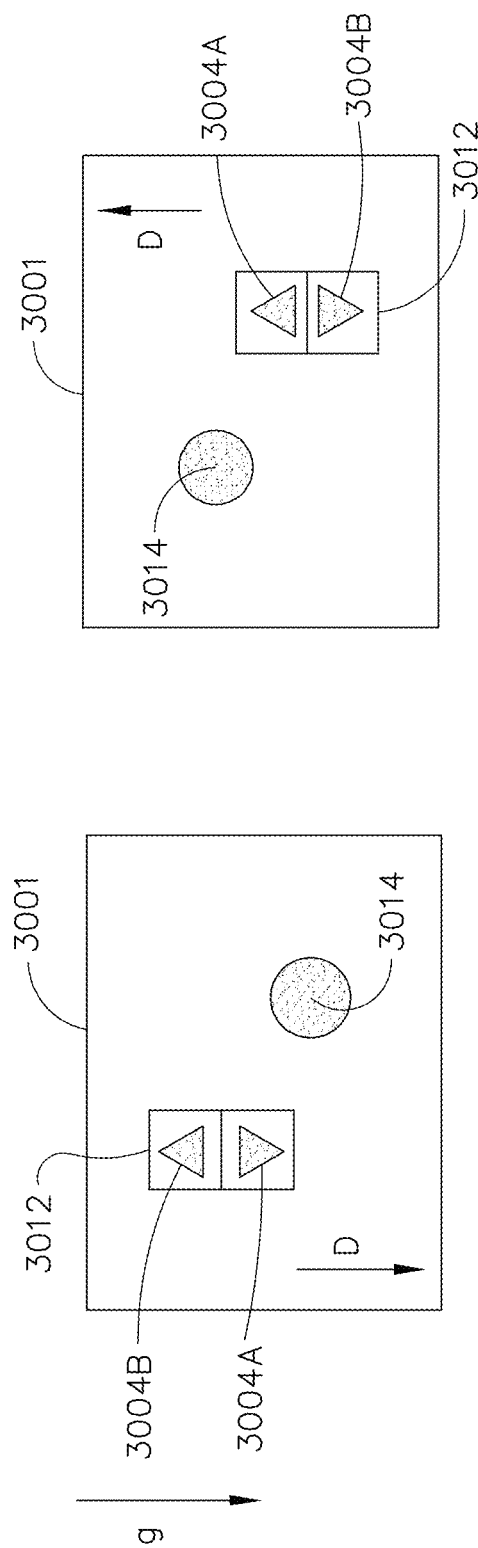
FIG. 14A
FIG. 14B
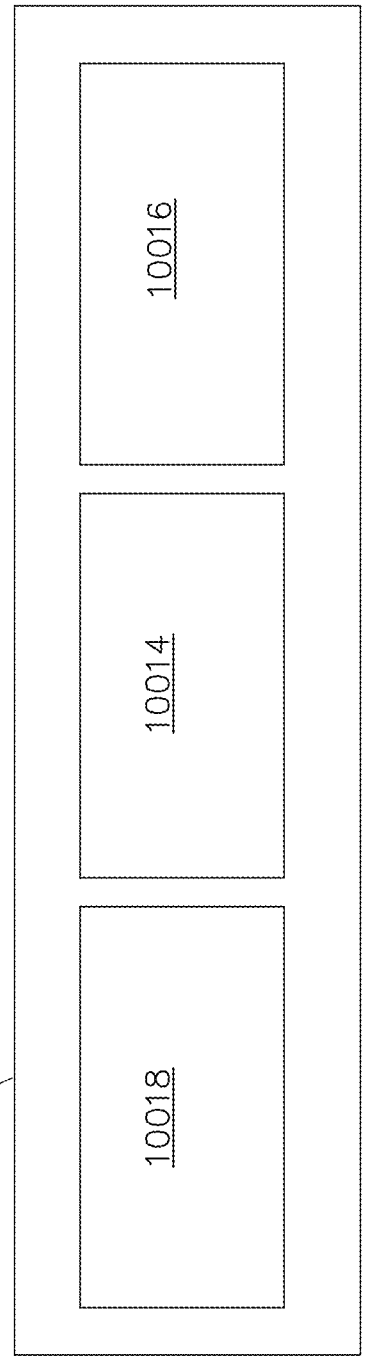
FIG. 15

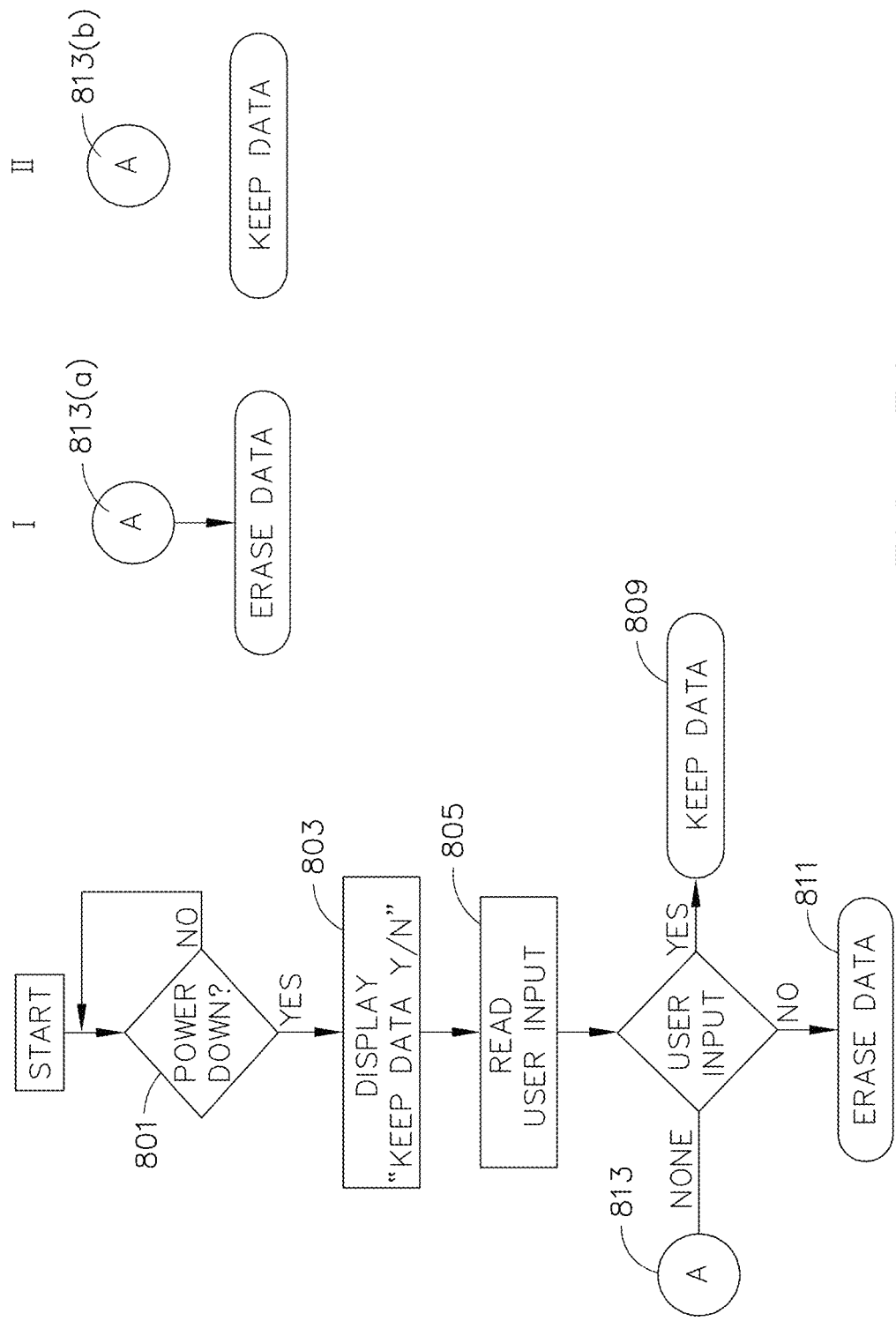

SURGICAL INSTRUMENT WITH MULTIPLE INTERFACE CONFIGURATIONS

CROSS-REFERENCE TO RELATED APPLICATIONS

This application is a continuation application claiming priority under 35 U.S.C. § 120 to U.S. patent application Ser. No. 17/590,525, entitled INTERFACE SYSTEMS FOR USE WITH SURGICAL INSTRUMENTS, filed Feb. 1, 2022, now U.S. Pat. No. 12,023,023, which is a continuation application claiming priority under 35 U.S.C. § 120 to U.S. patent application Ser. No. 16/585,883, entitled INTERFACE SYSTEMS FOR USE WITH SURGICAL INSTRUMENTS, filed Sep. 27, 2019, which issued on Mar. 1, 2022 as U.S. Pat. No. 11,259,799, which is a continuation application claiming priority under 35 U.S.C. § 120 to U.S. patent application Ser. No. 16/164,094, entitled SURGICAL INSTRUMENT POWER MANAGEMENT THROUGH SLEEP AND WAKE UP CONTROL, filed Oct. 18, 2018, which issued on Jan. 26, 2021 as U.S. Pat. No. 10,898,185, which is a continuation application claiming priority under 35 U.S.C. § 120 to U.S. patent application Ser. No. 15/459,515, entitled SURGICAL INSTRUMENT DISPLAYING SUBSEQUENT STEP OF USE, filed Mar. 15, 2017, which issued on Mar. 17, 2020 as U.S. Pat. No. 10,588,626, which is a continuation application claiming priority under 35 U.S.C. § 120 to U.S. patent application Ser. No. 14/226,126, entitled INTERFACE SYSTEMS FOR USE WITH SURGICAL INSTRUMENTS, filed Mar. 26, 2014, which issued on Jun. 26, 2018, as U.S. Pat. No. 10,004,497, the entire disclosures of which are hereby incorporated by reference herein.

BACKGROUND

The present invention relates to surgical instruments and, in various circumstances, to surgical stapling and cutting instruments and staple cartridges therefor that are designed to staple and cut tissue.

BRIEF DESCRIPTION OF THE DRAWINGS

The features and advantages of this invention, and the manner of attaining them, will become more apparent and the invention itself will be better understood by reference to the following description of instances of the invention taken in conjunction with the accompanying drawings, wherein:

FIG. 14A is a side view of the handle assembly of FIG. 10 in an upright position;

FIG. 14B is a side view of the handle assembly of FIG. 10 in an upside down position;

FIG. 15 is a schematic illustration of the display of FIG. 10 showing a plurality of icons;

FIG. 30 is a flow chart depicting a method for processing data recorded by a surgical instrument according to various embodiments of the present disclosure;

DETAILED DESCRIPTION

Figure 1:
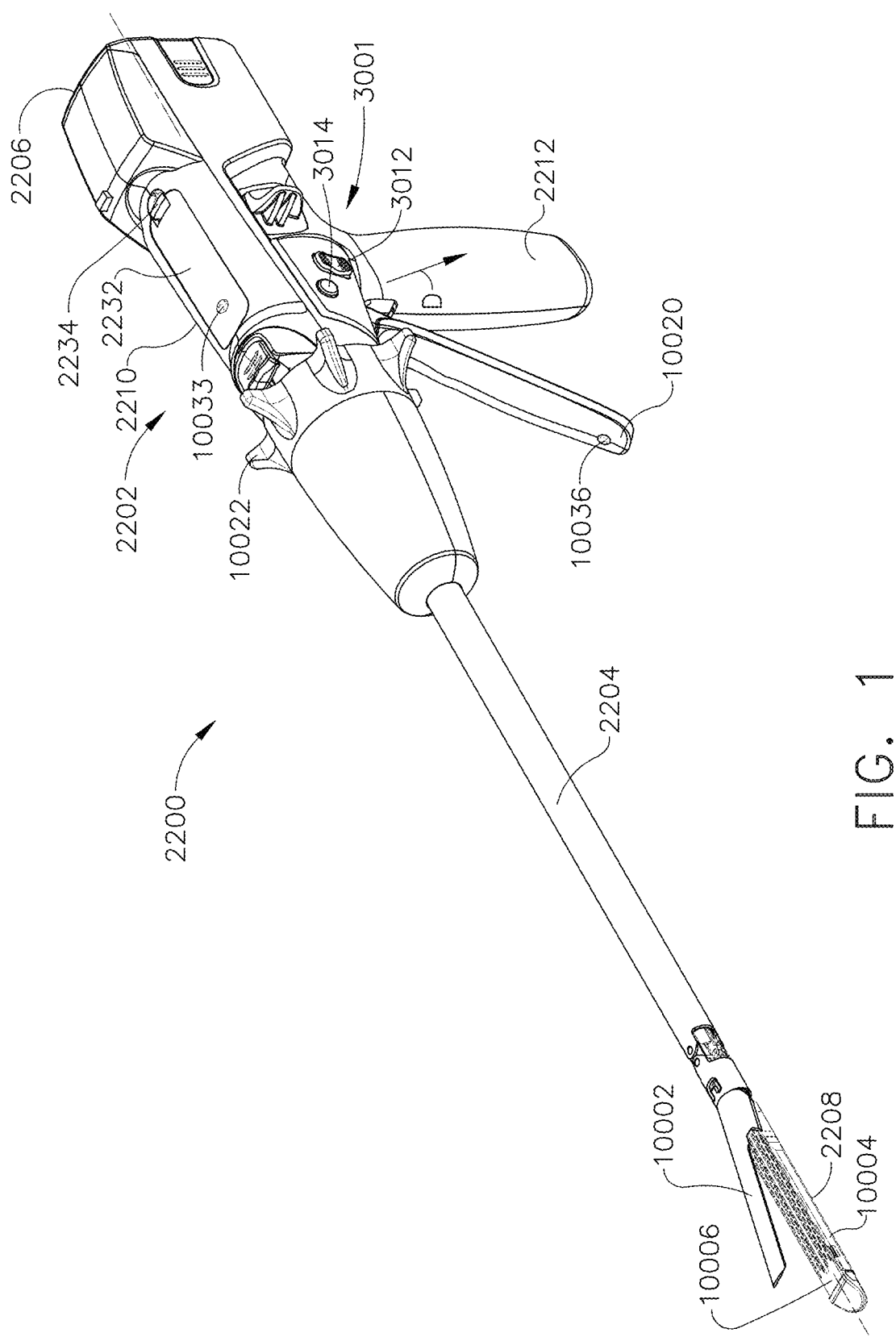
FIG. 1 is a perspective view of a surgical instrument comprising a handle assembly and a shaft assembly including an end effector.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003; U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986, are hereby incorporated by reference in their entireties.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent applications that were filed on Mar. 26, 2014, and are each herein incorporated by reference in their respective entireties:

U.S. patent application Ser. No. 14/226,142, entitled SURGICAL INSTRUMENT COMPRISING A SENSOR SYSTEM, now U.S. Pat. No. 9,913,642;

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

FIG. 1 generally depicts a motor-driven surgical instrument 2200. In certain circumstances, the surgical instrument 2200 may include a handle assembly 2202, a shaft assembly 2204, and a power assembly 2206 (or "power source" or "power pack"). The shaft assembly 2204 may include an end effector 2208 which, in certain circumstances, can be configured to act as an endocutter for clamping, severing, and/or stapling tissue, although, in other circumstances, different types of end effectors may be used, such as end effectors for other types of surgical devices, graspers, cutters, staplers, clip appliers, access devices, drug/gene therapy devices, ultrasound, RF and/or laser devices, etc. Several RF devices may be found in U.S. Pat. No. 5,403,312, entitled ELECTROSURGICAL HEMOSTATIC DEVICE, which issued on Apr. 4, 1995, which is incorporated herein by reference in its entirety.

Referring again to FIG. 1, the handle assembly 2202 may comprise a housing 2210 that includes a handle 2212 that may be configured to be grasped, manipulated, and/or actuated by a clinician. However, it will be understood that the various unique and novel arrangements of the housing 2210 may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the shaft assembly 2204 disclosed herein and its respective equivalents. For example, the housing 2210 disclosed herein may be employed with various robotic systems, instruments, components, and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535. The disclosure of U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, is incorporated by reference herein in its entirety.

In certain instances, the surgical instrument 2200 may include several operable systems that extend, at least partially, through the shaft 2204 and are in operable engagement with the end effector 2208. For example, the surgical instrument 2200 may include a closure assembly that may transition the end effector 2208 between an open configuration and a closed configuration, an articulation assembly that may articulate the end effector 2208 relative to the shaft 2204, and/or a firing assembly that may fasten and/or cut tissue captured by the end effector 2208. In addition, the housing 2210 may be separably couplable to the shaft 2204 and may include complimenting closure, articulation, and/or firing drive systems for operating the closure, articulation, and firing assemblies, respectively.

In use, an operator of the surgical instrument 2200 may desire to reset the surgical instrument 2200 and return one or more of the assemblies of the surgical instrument 2200 to a default position. For example, the operator may insert the end effector 2208 into a surgical site within a patient through an access port and may then articulate and/or close the end effector 2208 to capture tissue within the cavity. The operator may then choose to undo some or all of the previous actions and may choose to remove the surgical instrument 2200 from the cavity, for instance. The surgical instrument 2200 may include one more systems configured to facilitate a reliable return of one or more of the assemblies described above to a home state with minimal input from the operator thereby allowing the operator to remove the surgical instrument from the cavity.

Figure 3:
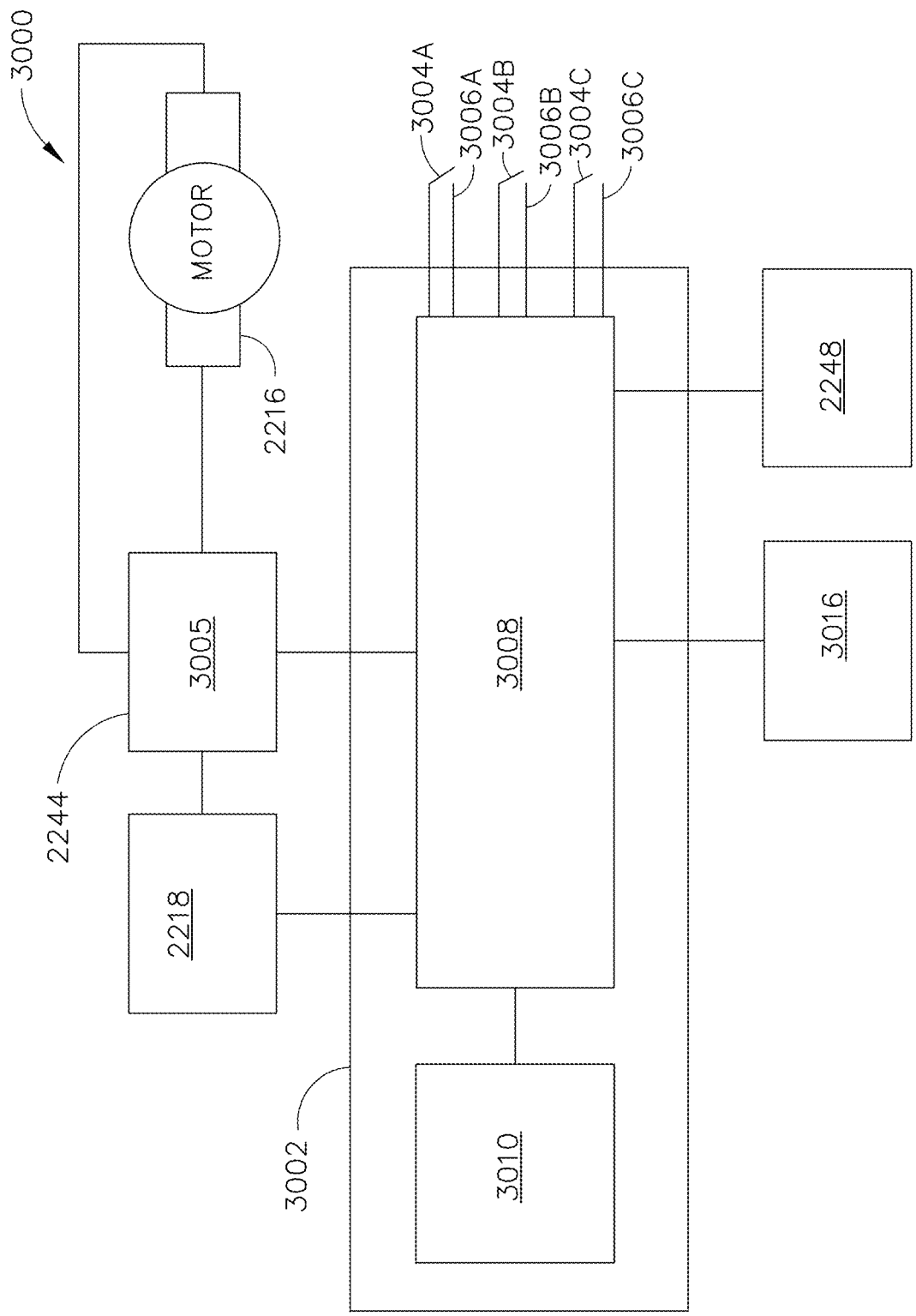
FIG. 3 is a schematic block diagram of a control system of the surgical instrument of FIG. 1.

Referring to FIGS. 1 and 3, the surgical instrument 2200 may include a control system 3000. A surgical operator may utilize the control system 3000 to articulate the end effector 2208 relative to the shaft 2204 between an articulation home state position and an articulated position, for example. In certain instances, the surgical operator may utilize the control system 3000 to reset or return the articulated end effector 2208 to the articulation home state position. The control system 3000 can be positioned, at least partially, in the housing 2210. In certain instances, as illustrated in in FIG. 3, the control system 3000 may comprise a microcontroller 3002 ("controller") which can be configured to receive an input signal and, in response, activate a motor 2216 to cause the end effector 2208 to articulate in accordance with such an input signal, for example.

Further to the above, the end effector 2208 can be positioned in sufficient alignment with the shaft 2204 in the articulation home state position, also referred to herein as an unarticulated position such that the end effector 2208 and at least a portion of shaft 2204 can be inserted into or retracted from a patient's internal cavity through an access port such as, for example, a trocar positioned in a wall of the internal cavity without damaging the access port. In certain instances, the end effector 2208 can be aligned, or at least substantially aligned, with a longitudinal axis "LL" passing through the shaft 2204 when the end effector 2208 is in the articulation home state position, as illustrated in FIG. 1. In at least one instance, the articulation home state position can be at any angle up to and including 5°, for example, with the longitudinal axis "LL" on either side of the longitudinal axis "LL". In another instance, the articulation home state position can be at any angle up to and including 3°, for example, with the longitudinal axis "LL" on either side of the longitudinal axis "LL". In yet another instance, the articulation home state position can be at any angle up to and including 7°, for example, with the longitudinal axis "LL" on either side of the longitudinal axis "LL".

The control system 3000 can be operated to articulate the end effector 2208 relative to the shaft 2204 in a plane extending along the longitudinal axis "LL" in a first direction such as, for example, a clockwise direction and/or a second direction such as, for example, a counterclockwise direction. In at least one instance, the control system 3000 can be operated to articulate the end effector 2208 in the clockwise direction form the articulation home state position to an articulated position 10 degrees to the right of the longitudinal axis "LL", for example. In another example, the control system 3000 can be operated to articulate the end effector 2208 in the counterclockwise direction form the articulated position at 10 degrees to the right of the longitudinal axis "LL" to the articulation home state position. In yet another example, the control system 3000 can be operated to articulate the end effector 2208 relative to the shaft 2204 in the counterclockwise direction from the articulation home state position to an articulated position 10 degrees to the left of the longitudinal axis "LL", for example. The reader will appreciate that the end effector can be articulated to different angles in the clockwise direction and/or the counterclockwise direction.

Figure 2:
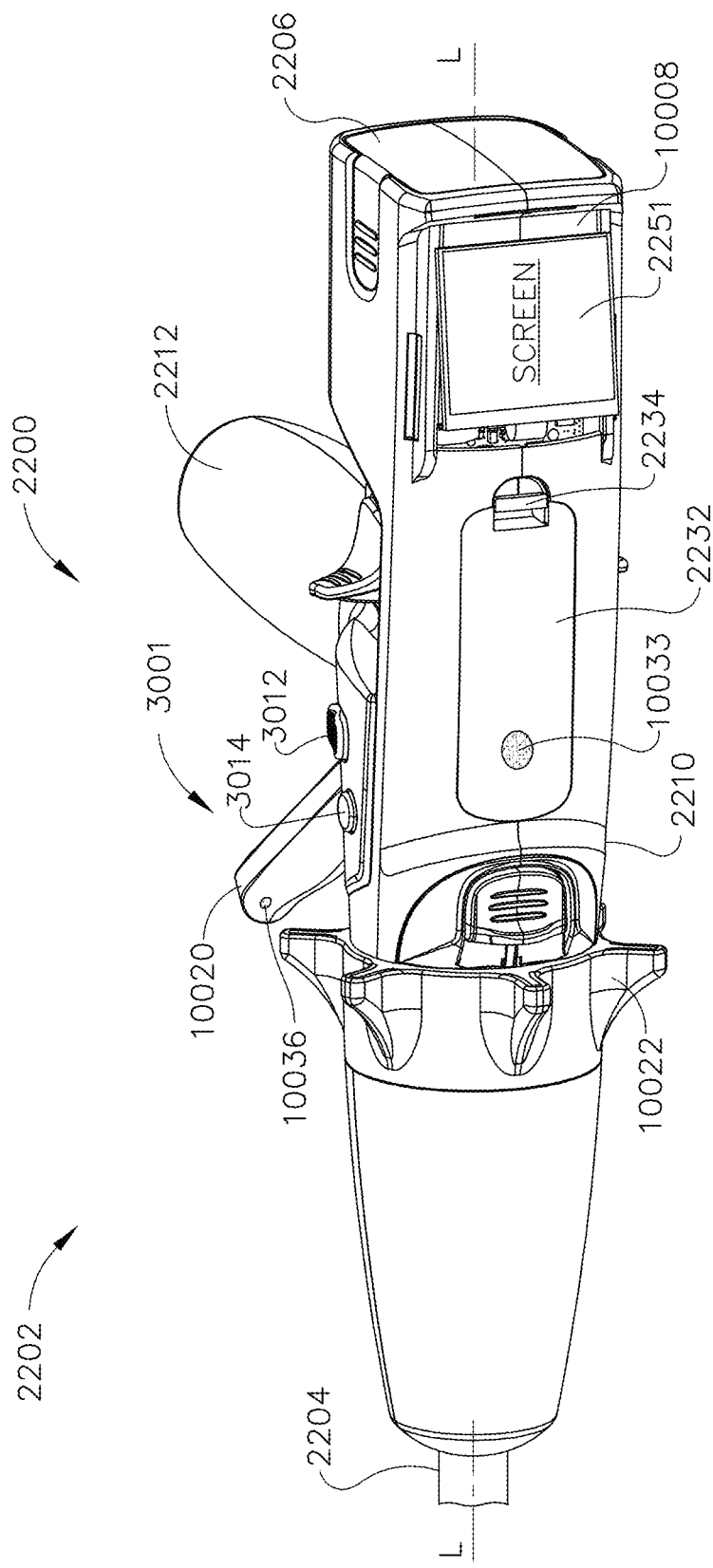
FIG. 2 is a perspective view of the handle assembly of the surgical instrument of FIG. 1.

Referring to FIGS. 1 and 2, the housing 2210 of the surgical instrument 2200 may comprise an interface 3001 which may include a plurality of controls that can be utilized by the operator to operate the surgical instrument 2200. In certain instances, the interface 3001 may comprise a plurality of switches which can be coupled to the controller 3002 via electrical circuits, for example. In certain instances, as illustrated in FIG. 3, the interface 3001 comprises three switches 3004A-C, wherein each of the switches 3004A-C is coupled to the controller 3002 via electrical circuits such as, for example electrical circuits 3006A-C, respectively. The reader will appreciate that other combinations of switches and circuits can be utilized with the interface 3001.

Referring to FIG. 3, the controller 3002 may generally comprise a microprocessor 3008 ("processor") and one or more memory units 3010 operationally coupled to the processor 3008. By executing instruction code stored in the memory 3010, the processor 3008 may control various components of the surgical instrument 2200, such as the motor 2216, various drive systems, and/or a user display, for example. The controller 3002 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the controller 3002 may include a hybrid circuit comprising discrete and integrated circuit elements or components on one or more substrates, for example.

In certain instances, the microcontroller 3002 may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHZ, a prefetch buffer to improve performance above 40 MHZ, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

In various forms, the motor 2216 may be a DC brushed driving motor having a maximum rotation of, approximately, 25,000 RPM, for example. In other arrangements, the motor 2216 may include a brushless motor, a cordless motor, a synchronous motor, a stepper motor, or any other suitable electric motor. A battery 2218 (or "power source" or "power pack"), such as a Li ion battery, for example, may be coupled to the housing 2212 to supply power to the motor 2216, for example.

Referring again to FIG. 3, the surgical instrument 2200 may include a motor controller 3005 in operable communication with the controller 3002. The motor controller 3005 can be configured to control a direction of rotation of the motor 2216. In certain instances, the motor controller 3005 may be configured to determine the voltage polarity applied to the motor 2216 by the battery 2218 and, in turn, determine the direction of rotation of the motor 2216 based on input from the controller 3002. For example, the motor 2216 may reverse the direction of its rotation from a clockwise direction to a counterclockwise direction when the voltage polarity applied to the motor 2216 by the battery 2218 is reversed by the motor controller 3005 based on input from the controller 3002. In addition, the motor 2216 can be operably coupled to an articulation drive which can be driven by the motor 2216 distally or proximally depending on the direction in which the motor 2216 rotates, for example. Furthermore, the articulation drive can be operably coupled to the end effector 2208 such that, for example, the axial translation of the articulation drive proximally may cause the end effector 2208 to be articulated in the counterclockwise direction, for example, and/or the axial translation of the articulation drive distally may cause the end effector 2208 to be articulated in the clockwise direction, for example.

Figure 7:
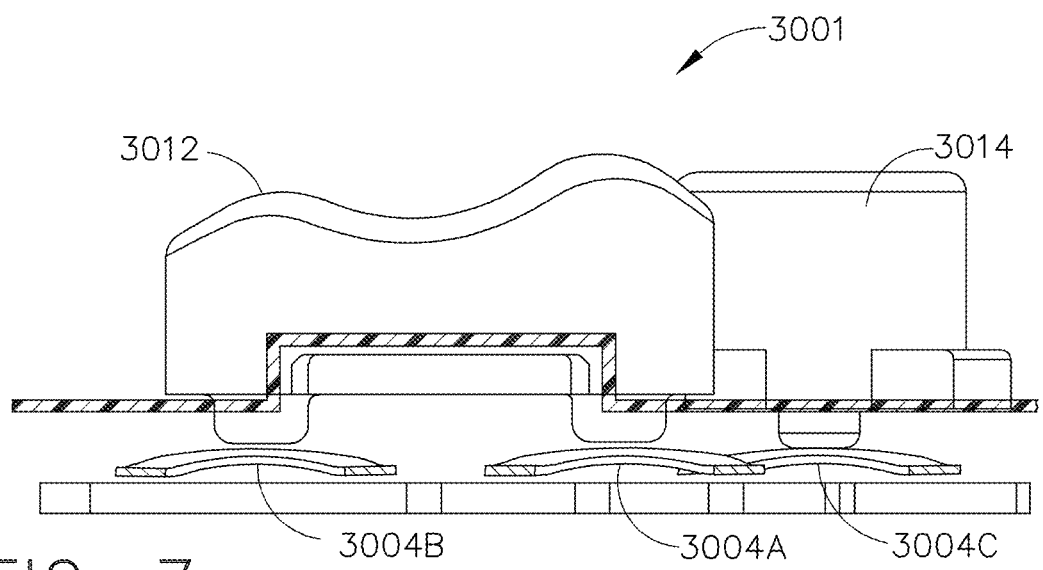
FIG. 7 is a schematic illustration of an interface of the surgical instrument of FIG. 1 in an inactive or neutral configuration.

In various instances, referring to FIGS. 1-3, the interface 3001 can be configured such that the switch 3004A can be dedicated to the clockwise articulation of the end effector 2208, for example, and the switch 3004B can be dedicated to the counterclockwise articulation of the end effector 2208, for example. In such instances, the operator may articulate the end effector 2208 in the clockwise direction by closing the switch 3004A and may articulate the end effector 2208 in the counterclockwise direction by closing the switch 3004B. In various instances, the switches 3004A-C can comprise open-biased dome switches, as illustrated in FIG. 7. Other types of switches can also be employed such as, for example, capacitive switches.

Figure 8:
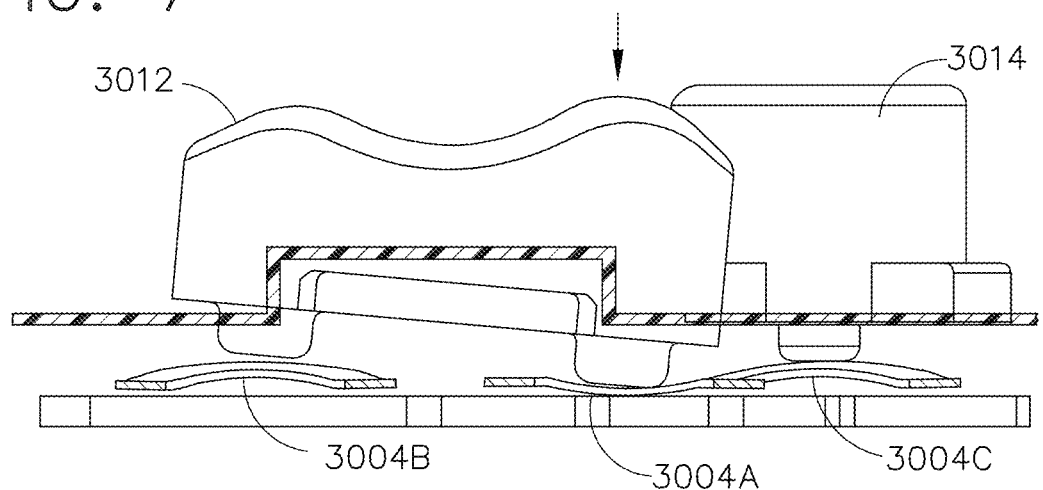
FIG. 8 is a schematic illustration of the interface of FIG. 7 activated to articulate an end effector.

Referring to FIG. 7, the dome switches 3004A and 3004B can be controlled by a rocker 3012. Other means for controlling the switches 3004A and 3004B are contemplated by the present disclosure. In the neutral position, as illustrated in FIG. 7, both of the switches 3004A and 3004B are biased in the open position. The operator, for example, may articulate the end effector 2208 in the clockwise direction by tilting the rocker forward thereby depressing the dome switch 3004A, as illustrated in FIG. 8. In result, the circuit 3006A (FIG. 3) may be closed signaling the controller 3002 to activate the motor 2216 to articulate the end effector 2208 in the clockwise direction, as described above. The motor 2216 may continue to articulate the end effector 2208 until the operator releases the rocker 3012 thereby allowing the dome switch 3004A to return to the open position and the rocker 3012 to the neutral position. In some circumstances, the controller 3002 may be able to identify when the end effector 2208 has reached a predetermined maximum degree of articulation and, at such point, interrupt power to the motor 2216 regardless of whether the dome switch 3004A is being depressed. In a way, the controller 3002 can be configured to override the operator's input and stop the motor 2216 when a maximum degree of safe articulation is reached. Alternatively, the operator may articulate the end effector 2208 in the counterclockwise direction by tilting the rocker 3012 back thereby depressing the dome switch 3004B, for example. In result, the circuit 3006B may be closed signaling the controller 3002 to activate the motor 2216 to articulate the end effector 2208 in the counterclockwise direction, as described above. The motor 2216 may continue to articulate the end effector 2208 until the operator releases the rocker 3012 thereby allowing the dome switch 3004B to return to the open position and the rocker 3012 to the neutral position. In some circumstances, the controller 3002 may be able to identify when the end effector 2208 has reached a predetermined maximum degree of articulation and, at such point, interrupt power to the motor 2216 regardless of whether the dome switch 3004B is being depressed. In a way, the controller 3002 can be configured to override the operator's input and stop the motor 2216 when a maximum degree of safe articulation is reached.

As described above in greater detail, an operator may desire to return the end effector 2208 to the articulation home state position to align, or at least substantially align, the end effector 2208 with the shaft 2204 in order to retract the surgical instrument 2200 from a patient's internal cavity, for example. In various instances, the control system 3000 may include a virtual detent that may alert the operator when the end effector 2208 has reached the articulation home state position. In certain instances, the control system 3000 may be configured to stop the articulation of the end effector 2208 upon reaching the articulation home state position, for example. In certain instances, the control system 3000 may be configured to provide feedback to the operator when the end effector 2208 reaches the articulation home state position, for example.

Figure 4:
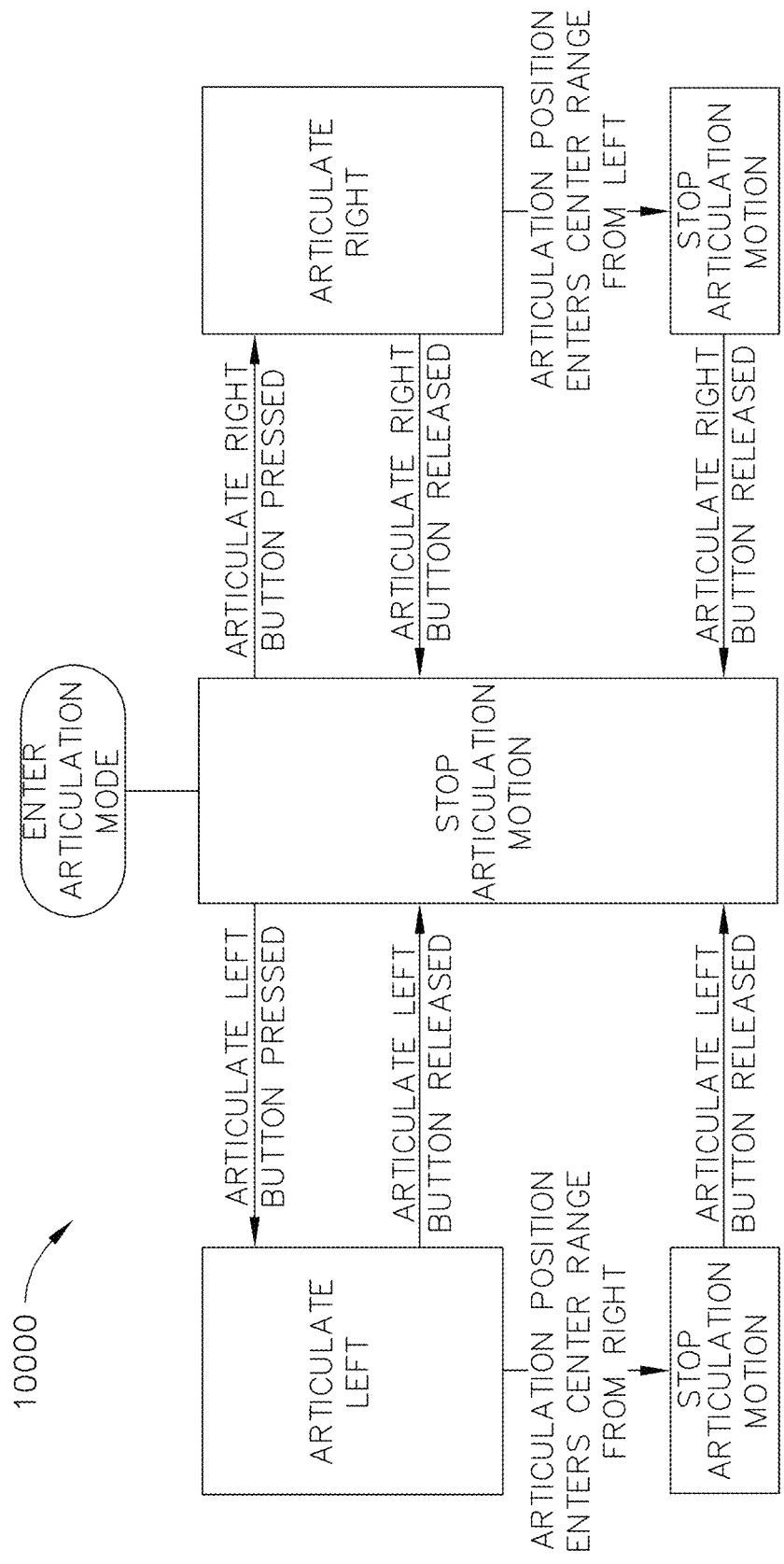
FIG. 4 is a schematic block diagram of a module for use with the surgical instrument of FIG. 1.

In certain instances, the control system 3000 may comprise various executable modules such as software, programs, data, drivers, and/or application program interfaces (APIs), for example. FIG. 4 depicts an exemplary virtual detent module 10000 that can be stored in the memory 3010, for example. The module 10000 may include program instructions, which when executed may cause the processer 3008, for example, to alert the operator of the surgical instrument 2200 when the end effector 2208 reaches the articulation home state position during the articulation of the end effector 2208 from an articulated position, for example.

As described above, referring primarily to FIGS. 3, 7, and 8, the operator may use the rocker 3012 to articulate the end effector 2208, for example. In certain instances, the operator may depress the dome switch 3004A of the rocker 3012 to articulate the end effector 2208 in a first direction such as a clockwise direction to the right, for example, and may depress the dome switch 3004B to articulate the end effector 2208 in a second direction such as a counterclockwise direction to the left, for example. In various instances, as illustrated in FIG. 4, the module 10000 may modulate the response of the processor 3008 to input signals from the dome switches 3004A and/or 3004B. For example, the processor 3008 can be configured to activate the motor 2216 to articulate the end effector 2208 to the right, for example, while the dome switch 3004A is depressed; and the processor 3008 can be configured to activate the motor 2216 to articulate the end effector 2208 to the left, for example, while the dome switch 3004B is depressed. In addition, the processor 3008 may be configured to stop the articulation of the end effector 2208 by causing the motor 2216 to stop, for example, when input signals from the dome switches 3004A and/or 3004B are stopped such as when the operator releases the dome switches 3004A and/or 3004B, respectively.

In various instances, as described above, the articulation home state position may comprise a range of positions. In certain instances, the processor 3008 can configured to detect when the end effector 2208 enters the range of positions defining the articulation home state position. In certain instances, the surgical instrument 2200 may comprise one or more positioning systems (not shown) for sensing and recording the articulation position of the end effector 2208. The processor 3008 can be configured to employ the one or more positioning systems to detect when the end effector 2208 enters the articulation home state position.

As illustrated in FIG. 4, in certain instances, upon reaching the articulation home state position, the processor 3008 may stop the articulation of the end effector 2208 to alert the operator that the articulation home state position is reached; the processor 3008, in certain instances, may stop the articulation in the articulation home state position even if the operator continues to depress the rocker 3012. In certain instances, in order to continue past the articulation home state position, the operator may release the rocker 3012 and then tilt it again to restart the articulation. In at least one such instance, the operator may push the rocker 3012 to depress dome switch 3004A, for example, to rotate the end effector 2208 toward its home state position until the end effector 2208 reaches its home state position and the processor 3008 stops the articulation of the end effector 2208, wherein the operator can then release the rocker 3012 and, then, push the rocker 3012 to depress the dome switch 3004A once again in order to continue the articulation of the end effector 2208 in the same direction.

Figure 5:
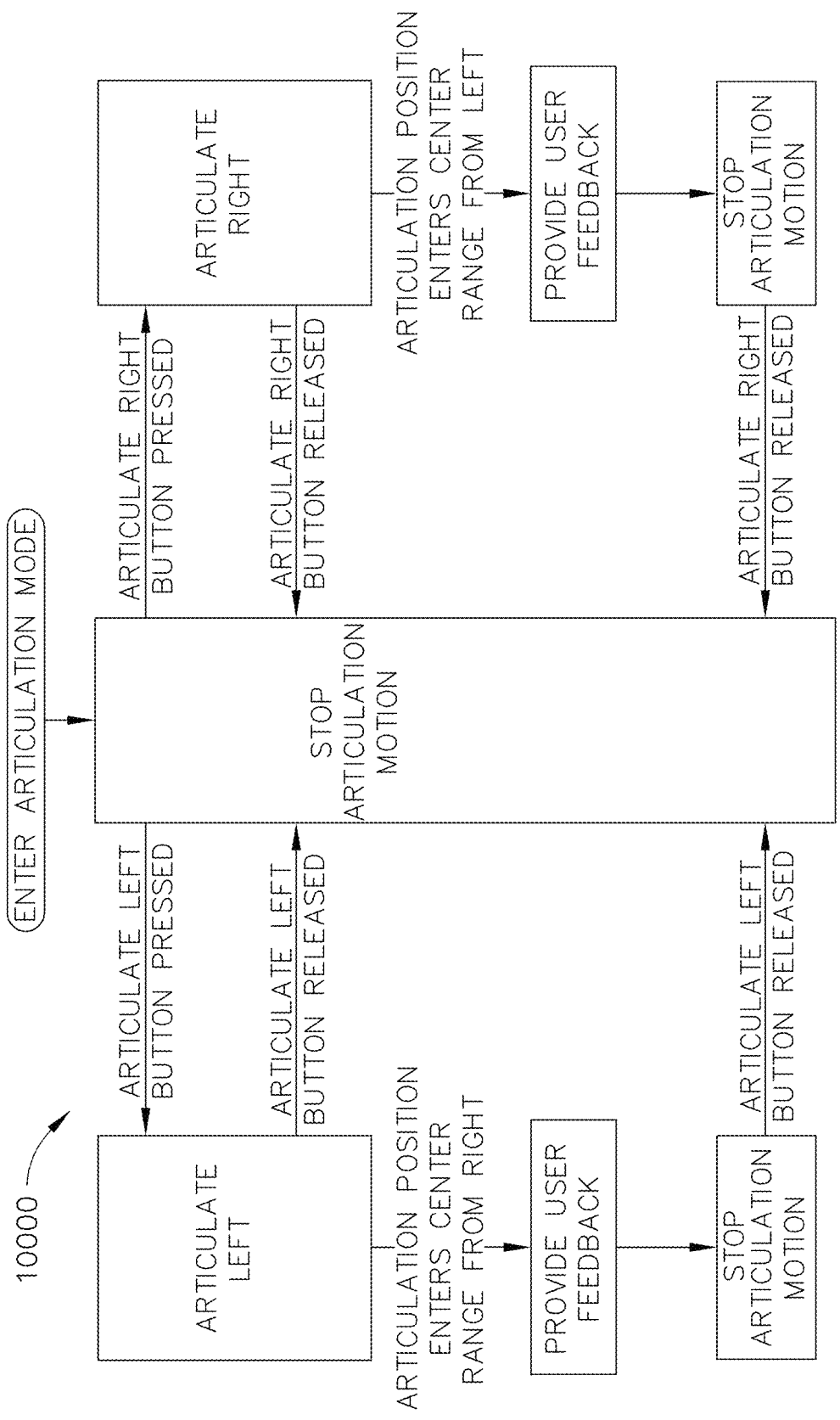
FIG. 5 is a schematic block diagram of a module for use with the surgical instrument of FIG. 1.

In certain instances, as illustrated in FIG. 5, the module 10000 may comprise a feedback mechanism to alert the operator when the articulation home state position is reached. Various feedback devices 2248 (FIG. 3) can be employed by the processor 3008 to provide sensory feedback to the operator. In certain instances, the devices 2248 may comprise, for example, visual feedback devices such as display screens and/or LED indicators, for example. In certain instances, the devices 2248 may comprise audio feedback devices such as speakers and/or buzzers, for example. In certain instances, the devices 2248 may comprise tactile feedback devices such as a mechanical detent, for example, which can provide haptic feedback, for example. In some instances, haptic feedback can be provided by a vibrating motor, for example, that can provide a pulse of vibrations to the handle of the surgical instrument, for example. In certain instances, the devices 2248 may comprise combinations of visual feedback devices, audio feedback devices, and/or tactile feedback devices, for example.

In certain instances, the processor 3008 can be configured to stop the articulation of the end effector 2208 and provide feedback to the operator when the articulation home state position is reached, for example. In certain instances, the processor 3008 may provide feedback to the operator but may not stop the articulation of the end effector 2208 when the articulation home state position is reached. In at least one instance, the end effector 2208 can be moved from a position on a first side of the home state position toward the home state position, pass through the home state position, and continue moving in the same direction on the other side of the home state position. During such movement, the operator may be supplied with some form of feedback at the moment the end effector 2208 passes through the home state position. In certain instances, the processor 3008 may stop the articulation of the end effector 2208 but may not provide feedback to the operator when the articulation home state position is reached, for example. In certain instances, the processor 3008 may pause the end effector 2208 as it passes through its center position and then continue past its center position. In at least one instance, the end effector 2208 can temporarily dwell in its center position for about 2 seconds, for example, and then continue its articulation so long as the articulation switch 3012 remains depressed.

In various instances, an operator of the surgical instrument 2200 may attempt to articulate the end effector 2208 back to its unarticulated position utilizing the rocker switch 3012. As the reader will appreciate, the operator may not be able to accurately and/or repeatably align the end effector 2208 with the longitudinal axis of the surgical instrument shaft. In various instances, though, the operator can readily position the end effector 2208 within a certain range of the center position. For instance, an operator may push the rocker switch 3012 to rotate the end effector 2208 toward its center position and then release the rocker switch 3012 when the operator believes that the end effector 2208 has reached its center position or is close to its center position. The processor 3008 can interpret such circumstances as an attempt to recenter the end effector 2208 and, in the event that the end effector 2208 is not in its center position, the processor 3008 can automatically center the end effector 2208. In at least one example, if the operator of the surgical instrument releases the rocker switch 3012 when the end effector 2208 is within about 10 degrees on either side of the center position, for example, the processor 3008 may automatically recenter the end effector 2208.

Figure 6:
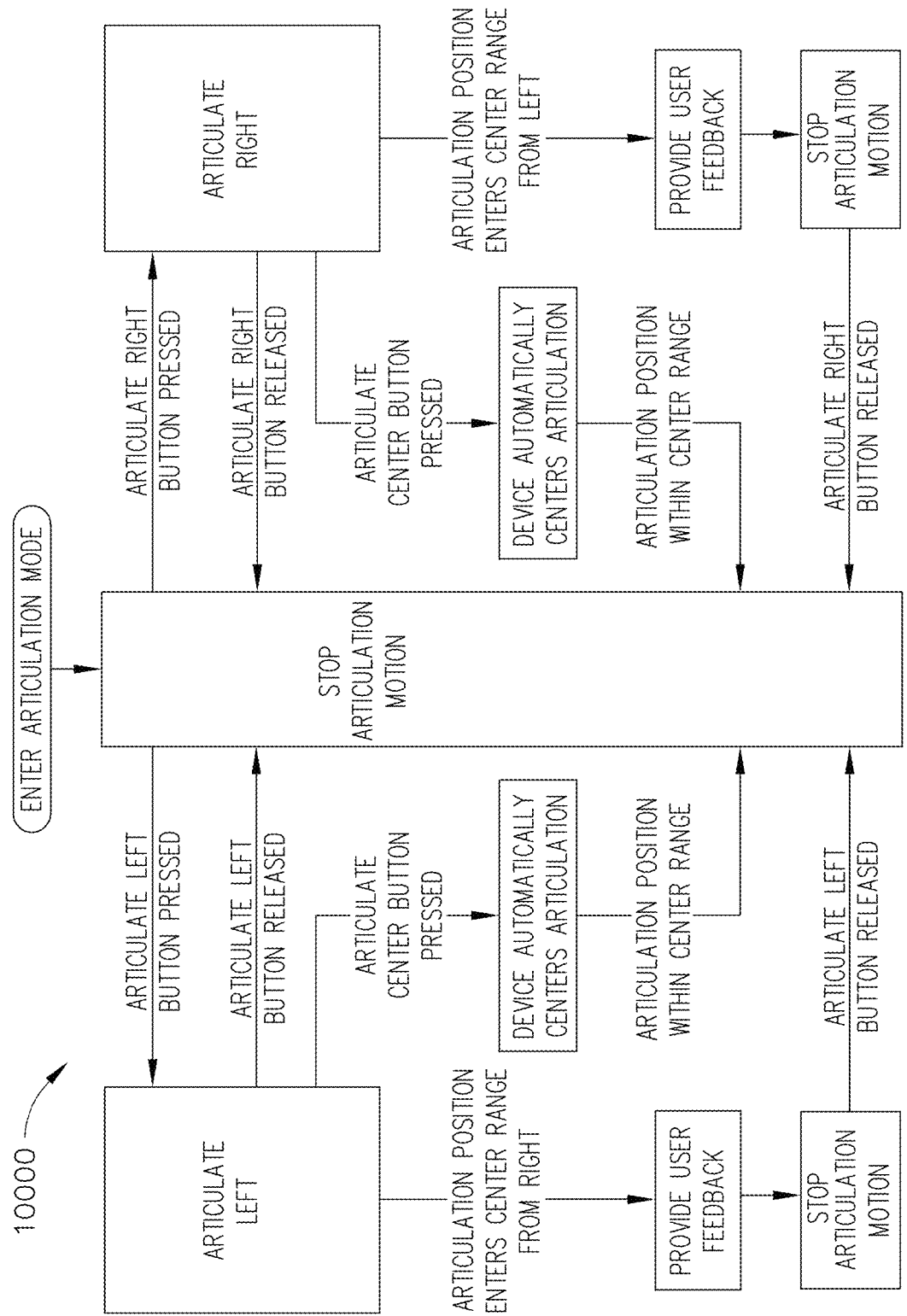
FIG. 6 is a schematic block diagram of a module for use with the surgical instrument of FIG. 1.
Figure 9:
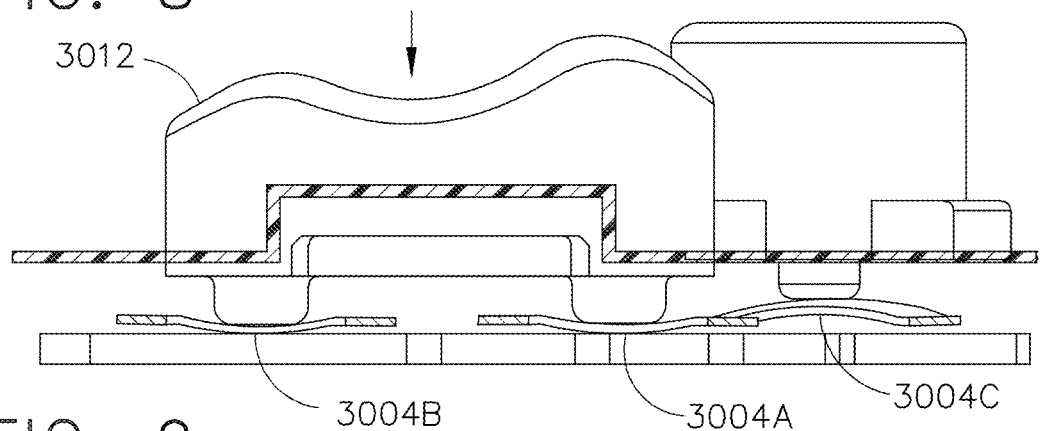
FIG. 9 is a schematic illustration of the interface of FIG. 7 activated to return the end effector to an articulation home state position.

In various instances, referring primarily to FIGS. 3, 6, and 9, the module 10000 may comprise an articulation resetting or centering mechanism. In certain instances, the control system 3000 may include a reset input which may reset or return the end effector 2208 to the articulation home state position if the end effector 2208 is in an articulated position. For example, upon receiving a reset input signal, the processor 3008 may determine the articulation position of the end effector 2208 and, if the end effector 2208 is in the articulation home state position, the processor 3008 may take no action to change the articulation position of the end effector 2208. However, if the end effector 2208 is in an articulated position when the processor 3008 receives a reset input signal, the processor 3008 may activate the motor 2216 to return the end effector 2208 to the articulation home state position. As illustrated in FIG. 9, the operator may depress the rocker 3012 downward to close the dome switches 3004A and 3004B simultaneously, or at least within a short time period from each other, which may transmit the reset input signal to the processor 3008 to reset or return the end effector 2208 to the articulation home state position. The operator may then release the rocker 3012 to allow the rocker 3012 to return to the neutral position and the switches 3004A and 3004B to the open positions. Alternatively, the interface 3001 of the control system 3000 may include a separate reset switch such as, for example, another dome switch which can be independently closed by the operator to transmit the articulation reset input signal to the processor 3008.

Referring again to FIG. 1, the end effector 2208 of the surgical instrument 2200 may include a first jaw comprising an anvil 10002 and a second jaw comprising a channel 10004 configured to receive a staple cartridge 10006 which may include a plurality of staples. In certain instances, the end effector 2208 can be transitioned between an open configuration and a closed configuration to capture tissue between the anvil 10002 and the staple cartridge 10006, for example. Furthermore, the surgical instrument 2200 may include a firing member which can be moved axially between a firing home state position and a fired position to deploy the staples from the staple cartridge 10006 and/or cut the tissue captured between the anvil 10002 and the staple cartridge 10006 when the end effector 2208 is in the closed configuration.

As discussed above, the end effector 2208 can be transitioned between an open configuration and a closed configuration to clamp tissue therein. In at least one embodiment, the anvil 10002 can be moved between an open position and a closed position to compress tissue against the staple cartridge 10006. In various instances, the pressure or force that the anvil 10002 can apply to the tissue may depend on the thickness of the tissue. For a given gap distance between the anvil 10002 and the staple cartridge 10006, the anvil 10002 may apply a larger compressive pressure or force to thicker tissue than thinner tissue. The surgical instrument can include a sensor, such as a load cell, for example, which can detect the pressure or force being applied to the tissue. In certain instances, the thickness and/or composition of the tissue may change while pressure or force is being applied thereto. For instance, fluid, such as blood, for example, contained within the compressed tissue may flow outwardly into the adjacent tissue. In such circumstances, the tissue may become thinner and/or the compressive pressure or force applied to the tissue may be reduced. The sensor configured to detect the pressure of force being applied to the tissue may detect this change. The sensor can be in signal communication with the processor 3008 wherein the processor 3008 can monitor the pressure or force being applied to the tissue and/or the change in the pressure of force being applied to the tissue. In at least one instance, the processor 3008 can evaluate the change in the pressure or force and communicate to the operator of the surgical instrument when the pressure or force has reached a steady state condition and is no longer changing. The processor 3008 can also determine when the change in the pressure or force is at and/or below a threshold value, or rate. For instance, when the change in the pressure or force is above about 10 percent per second, the processor 3008 can illuminate a caution indicator associated with the firing actuator, for example, and when the change in the pressure or force is at or below about 10 percent per second, the processor can illuminate a ready-to-fire indicator associated with the firing actuator, for example. In some circumstances, the surgical instrument may prohibit the firing member from being advanced distally through the end effector 2208 until the change in pressure or force is at and/or below the threshold rate, for example.

In certain instances, the operator of the surgical instrument may elect to deploy only some of the staples stored within the end effector 2208. After the firing member has been sufficiently advanced, in such circumstances, the firing member can be retracted. In various other instances, the operator of the surgical instrument may elect to deploy all of the staples stored within the end effector 2208. In either event, the operator of the surgical instrument can depress a firing actuator extending from the handle assembly 2210 to actuate the motor 2216 and advance the firing member distally. The motor 2216 can be actuated once the firing actuator has been sufficiently depressed. In at least one mode of operation, further depression of the firing actuator may not affect the operation of the motor 2216. The motor 2216 may be operated in the manner dictated by the processor 3008 until the firing actuator is released. In at least one other mode of operation, the degree or amount in which the firing actuator is depressed may affect the manner in which the motor 2216 is operated. For instance, an initial depression of the firing actuator can be detected by the processor 3008 and, in response thereto, the processor 3008 can operate the motor 2216 at a first speed, wherein additional depression of the firing actuator can be detected by the processor 3008 and, in response thereto, the processor 3008 can operate the motor 2216 at a second speed, such as a faster speed, for example. In certain instances, the change in the depression of the firing actuator can be proportional to the change in the motor speed. In at least one instance, the change in the depression of the firing actuator can be linearly proportional to the change in the motor speed. In various circumstances, the further the firing actuator is pulled, the faster the motor 2216 is operated. In certain embodiments, the amount of pressure or force applied to the firing actuator may affect the manner in which the motor 2216 is operated. For instance, an initial pressure or force applied to the firing actuator can be detected by the processor 3008 and, in response thereto, the processor 3008 can operate the motor 2216 at a first speed, wherein additional pressure or force applied to the firing actuator can be detected by the processor 3008 and, in response thereto, the processor 3008 can operate the motor 2216 at a second speed, such as a faster speed, for example. In certain instances, the change in the pressure or force applied to the firing actuator can be proportional to the change in the motor speed. In at least one instance, the change in the pressure or force applied to the firing actuator can be linearly proportional to the change in the motor speed. The disclosure of U.S. Pat. No. 7,845,537, entitled SURGICAL INSTRUMENT HAVING RECORDING CAPABILITIES, which issued on Dec. 7, 2010, is incorporated by reference in its entirety.

As discussed above, the operator of the surgical instrument may elect to deploy all of the staples stored within the end effector 2208. In such circumstances, the operator may depress the firing actuator and then release the actuator when they believe that all of the staples have been deployed during a firing stroke of the firing member. In some instances, the surgical instrument can include an indicator which can be illuminated by the processor 3008 when the firing stroke has been completed. A suitable indicator can comprise a light emitting diode (LED), for example. In certain instances, the operator may believe that a firing stroke has been fully completed even though it may have only been nearly completed. The surgical instrument can comprise at least one sensor configured to detect the position of the firing member within its firing stroke wherein the sensor can be in signal communication with the processor 3008. In the event that the firing stroke is ended at a nearly completed position, the processor 3008 can command the motor 2216 to finish the firing stroke of the firing member. For instance, if the firing member has completed all but the last 5 mm of the firing stroke, for example, the processor 3008 can assume that the operator meant to complete the firing stroke and automatically complete the firing stroke.

Referring again to FIG. 1, the interface 3001 of the surgical instrument 2200 may include a home state input 3014. The operator may utilize the home state input to transmit a home state input signal to the processor 3008 to return the surgical instrument 2200 to home state which may include returning the end effector 2208 to the articulation home state position and/or the firing member to the firing home state position. As illustrated in FIGS. 3 and 7, the home state input 3014 may include a cap or a cover, for example, which can be depressed by the operator to close the switch 3004C and transmit the home state input signal through the circuit 3006C to the processor 3008. In certain instances, the home state input 3014 can be configured to return the end effector 2208 to the articulation home state position, and a separate input can be utilized to return the firing member to the firing home state position. In certain instances, the home state input 3014 can be configured to return the firing member to the firing home state position, and a separate input can be utilized to return the end effector 2208 to the articulation home state position such as, for example, the rocker 3012.

In various instances, the processor 3008 can be configured to cause the firing member to return to the firing home state position and the end effector 2208 to return to the articulation home state position upon receiving the home state input signal from the home state input 3014. In certain instances, the response of the processor 3008 to the home state input signal may depend on whether the surgical instrument 2200 is in a firing mode or an articulation mode; if the processor 3008 determines that the surgical instrument 2200 is in the articulation mode, the processor 3008 may cause the end effector 2208 to return to the articulation home state position in response to the home state input signal, for example; and if the processor 3008 determines that the surgical instrument 2200 is in the firing mode, the processor 3008 may cause the firing member to return to the firing home state position in response to the home state input signal, for example. In certain instances, the firing member can be advanced axially to fire the staples from the staple cartridge 10006 only when the end effector 2208 is in the closed configuration. In such instances, the surgical instrument 2200 can be in the firing mode only when the end effector 2208 is in the closed configuration. In certain instances, the end effector 2208 can be articulated only when the end effector 2208 is in the open configuration. In such instances, the surgical instrument 2200 can be in the articulation mode only when the end effector 2208 is in the open configuration. Accordingly, in certain instances, the processor 3008 can be configured to determine whether the surgical instrument 2200 is in the articulation mode or the firing mode by determining whether the end effector 2208 is in the open configuration or the closed configuration. In certain instances, one or more sensors 3016 (FIG. 3) can be employed by the processor 3008 to determine whether the end effector 2208 is in the open configuration or closed configuration.

Figure 10:
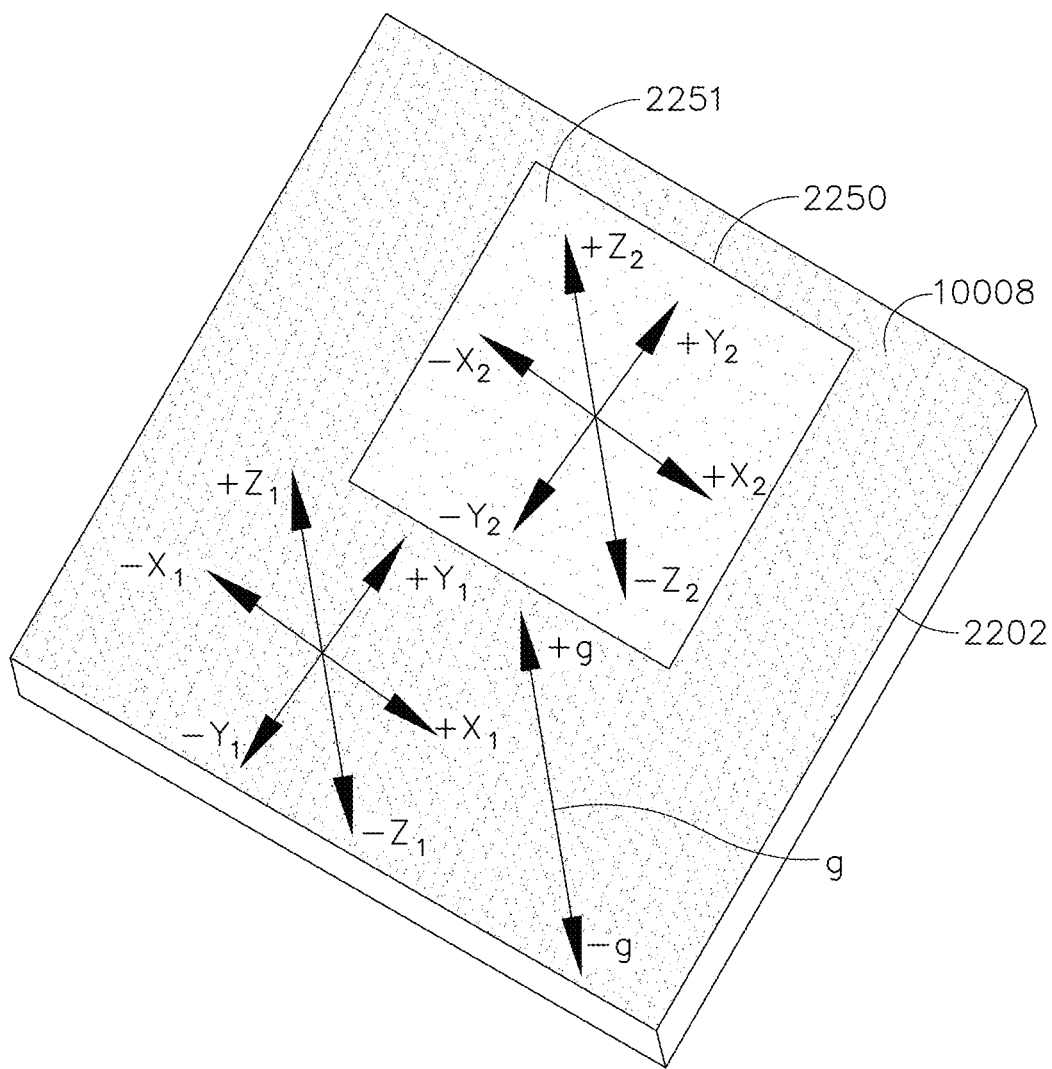
FIG. 10 is a schematic illustration of a partial view of a handle assembly of the surgical instrument of FIG. 1 depicting a display.

Referring now to FIGS. 1 and 10, the surgical instrument 2200 may comprise a screen 2251 which may be included in the handle assembly 2202, for example. The screen 2251 can be employed by one or more of the microcontrollers described herein to alert, guide, and/or provide feedback to the operator of the surgical instrument 2200, for example. The screen 2251 can produce an output display 2250. In use, the operator may tilt, flip, and/or rotate the handle assembly 2202, for example, and, in response, the microcontroller can change the orientation of the output display 2250 to improve, align, and/or adjust the orientation of the output display 2250 with respect to the view of the operator of the surgical instrument 2200 and/or any suitable frame of reference, such as an inertial, or at least substantially inertial, frame of reference, for example. A fixed frame of reference can be defined, at least in part, by gravity. In some instances, the downward acceleration of Earth's gravity can be represented by the vector-g in FIG. 10. In certain instances, a processor, such as the processor 3008, for example, may be configured to detect the changes in the position of the handle assembly 2202 with respect to the frame of reference and adopt one of a plurality of orientations of the screen 2251 in accordance with the relative position of the screen 2251 with respect to the frame of reference.

In certain instances, as illustrated in FIG. 10, the screen 2251 can be disposed on a top surface 10008 of the handle assembly 2202. In various instances, the surface 10008 may extend in a first plane defined by coordinates X1 and Y1 of a first set of Cartesian coordinates representing the handle assembly 2202. In various instances, the screen 2251 may be positioned within the first plane. In some instances, the screen 2251 may be positioned within a plane which extends parallel to the first plane and/or any suitable plane in a fixed relationship relative to the first plane. For the purposes of convenience herein, it will be assumed that the first set of Cartesian coordinates representing the handle assembly are aligned with the screen 2251 and, thus, referred to as a screen set of Cartesian coordinates. The output display 2250 can reside in a second plane defined by coordinates X2 and Y2 of a second, or display, set of Cartesian coordinates. In certain instances, as illustrated in FIG. 10, the first plane can be coplanar with the second plane, for example. Moreover, the first, or screen, set of Cartesian coordinates can be aligned with the second, or display, set of Cartesian coordinates, in at least some instances. For example, +X1 can be aligned with or parallel to +X2, +Y1 can be aligned with or parallel to +Y2, and +Z1 can be aligned with or parallel to +Z2. Correspondingly, in such instances, −X1 can be aligned with or parallel to −X2, −Y1 can be aligned with or parallel to −Y2, and −Z1 can be aligned with or parallel to −Z2. As will be described in greater detail below, the second, or display, set of Cartesian coordinates can be realigned with respect to the first, or screen, set of Cartesian coordinates in certain instances. In various instances, a certain arrangement of the display Cartesian coordinates can be preferred. For instance, a neutral position of the surgical instrument 2200 can coincide with the +Z1 axis of the screen coordinates being aligned with the +g vector. As will be described in greater detail below, the processor 3008 can tolerate a certain amount of deviation between the screen coordinates at the reference frame without changing the alignment o the display coordinates; however, beyond a certain deviation between the screen coordinates at the reference frame, the processor can change the alignment of the display coordinates relative to the screen coordinates.

Figure 11:
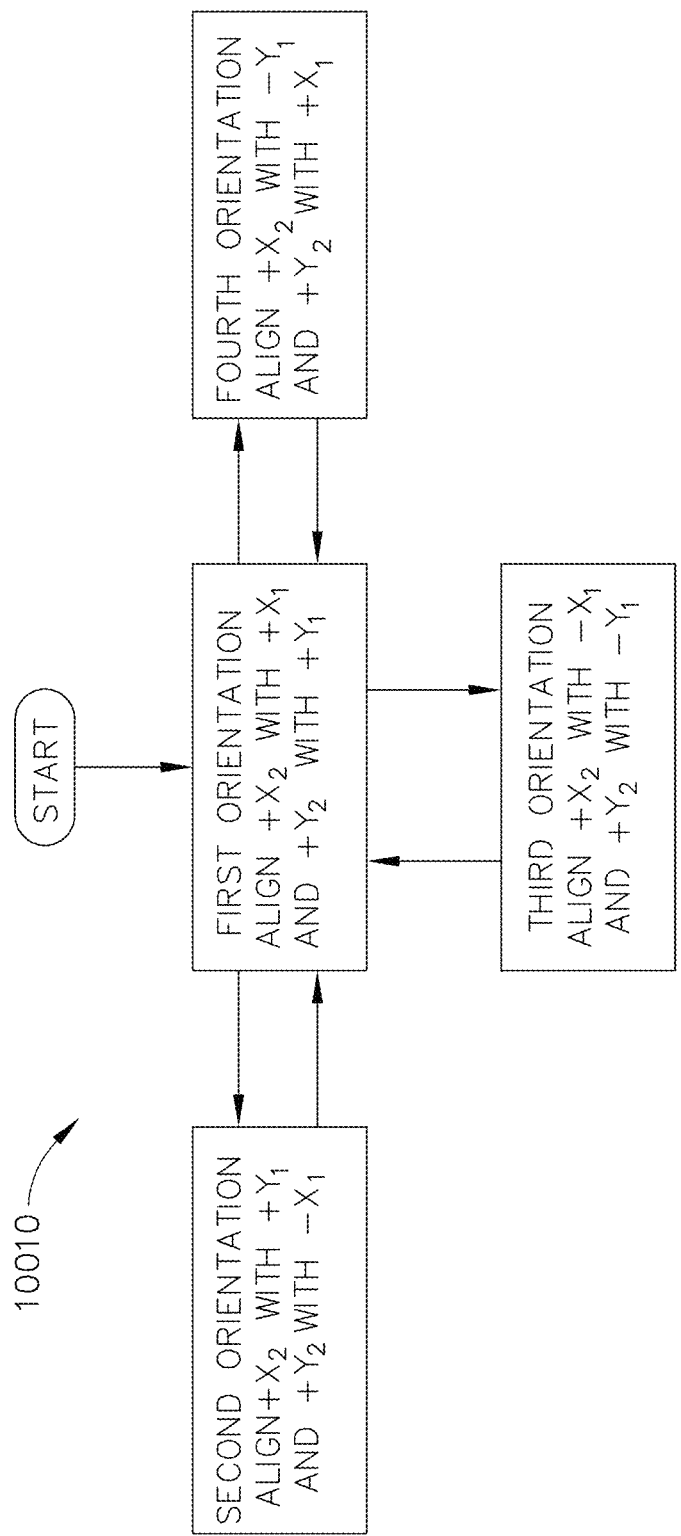
FIG. 11 depicts a module of the surgical instrument of FIG. 1.
Figure 12A:
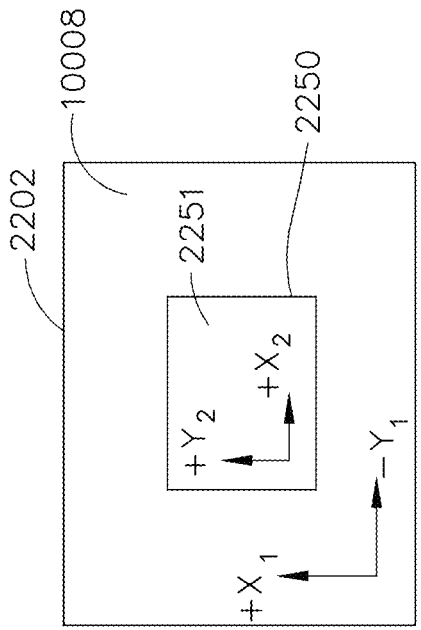
FIG. 12A is a schematic illustration of a screen orientation of the display of FIG. 10.
Figure 12C:
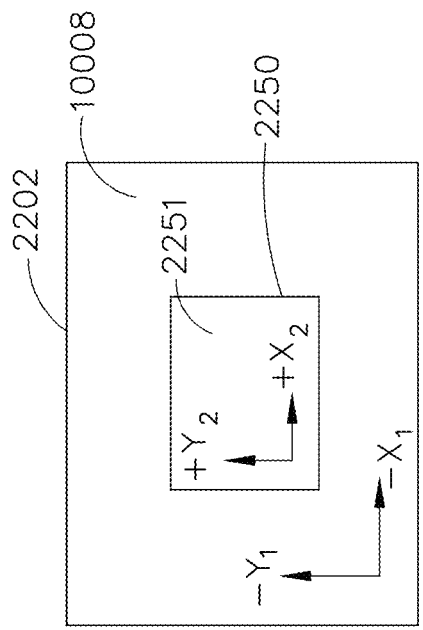
FIG. 12C is a schematic illustration of a screen orientation of the display of FIG. 10.
Figure 12B:
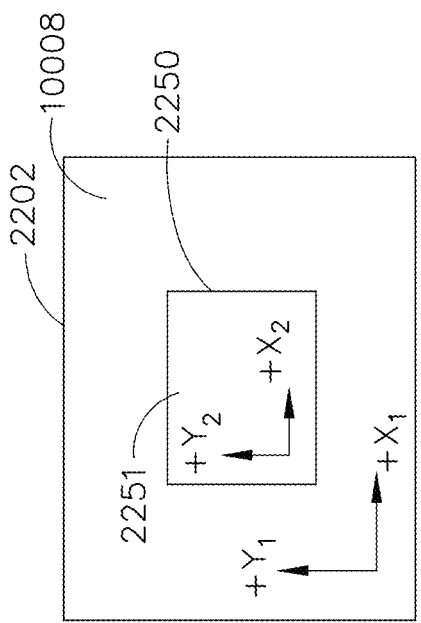
FIG. 12B is a schematic illustration of a screen orientation of the display of FIG. 10.
Figure 12D:
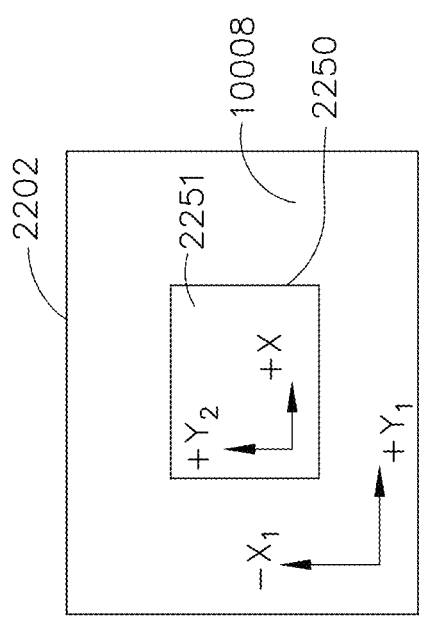
FIG. 12D is a schematic illustration of a screen orientation of the display of FIG. 10.

Referring to FIGS. 11-12D, a module 10010 can be configured to change or alter the orientation of the output display 2250 between a plurality of orientations in response to the changes in the position of the handle assembly 2202 which can be monitored through input from one or more accelerometers (not shown) that can be housed within the handle assembly 2202, for example. As discussed above, and as illustrated in FIG. 12A, the output display 2250 may adopt a first orientation wherein the +X2 and +Y2 vectors of the display set of Cartesian coordinates are aligned, or at least substantially aligned, with the +X1 and +Y1 vectors, respectively, of the screen set of Cartesian coordinates when the surgical instrument is in its neutral position. In certain instances, as illustrated in FIG. 12B, the output display 2250 may adopt a second orientation wherein the +Y2 and +X2 vectors of the display set of Cartesian coordinates are aligned, or at least substantially aligned, with the +Y1 and −X1 vectors, respectively, of the screen set of Cartesian coordinates, for example. In certain instances, as illustrated in FIG. 12C, the output display 2250 may adopt a third orientation wherein the +X2 and +Y2 vectors of the display set of Cartesian coordinates are aligned, or at least substantially aligned, with the −X1 and −Y1 vectors, respectively, of the screen set of Cartesian coordinates, for example. In certain instances, as illustrated in FIG. 12D, the output display 2250 may adopt a fourth orientation wherein the +X2 and +Y2 vectors of the second set of Cartesian coordinates are aligned, or at least substantially aligned, with the −Y1 and +X1 vectors, respectively, of the screen set of Cartesian coordinates, for example. Other orientations are possible.

Referring to FIGS. 11-12D, the processor 3008 can be configured to toggle the orientation of the output display 2250 between a plurality of orientations including the first orientation, the second orientation, the third orientation, and/or the fourth orientation, for example, to accommodate changes in the position of the handle assembly 2202, for example. In certain instances, the module 10010 may include a hysteresis control algorithm to prevent dithering of the orientation while toggling between the first, second, third, and/or fourth orientations, for example. A hysteresis control algorithm can produce a lag between an initial detection of an event that would result in a display orientation change and the processor command to change the display orientation. As such, the hysteresis control algorithm can ignore events which would result in a potentially transient orientation and optimally wait to reorient the display until a steady state, or sufficiently steady state, condition has been reached. In certain instances, the processor 3008 can be configured to orient the output display 2250 in the first orientation when an angle between the +Z1 vector of the Z1 axis and the −g vector of the gravity axis g is less than or equal to a maximum angle, for example. In certain instances, the processor 3008 can be configured to orient the output display 2250 in the second orientation when an angle between the +X1 vector of the X1 axis and the +g vector of the gravity axis g is less than or equal to a maximum angle, for example. In certain instances, the processor 3008 can be configured to orient the output display 2250 in the third orientation when an angle between the +Y1 vector of the Y1 axis and the +g vector of the gravity g axis is less than or equal to a maximum angle, for example. In certain instances, the processor 3008 can be configured to orient the output display 2250 in the fourth orientation when an angle between the +X1 vector of the X1 axis and the −g vector of the gravity axis g is less than or equal to a maximum angle, for example. In certain instances, the maximum angle can be any angle selected from a range of about 0 degrees, for example, to about 10 degrees, for example. In certain instances, the maximum angle can be any angle selected from a range of about 0 degrees, for example, to about 5 degrees, for example. In certain instances, the maximum angle can be about 5 degrees, for example. The maximum angles described above are exemplary and are not intended to limit the scope of the present disclosure.

Referring to FIGS. 11-12D, in certain instances, the processor 3008 can be configured to orient the output display 2250 in the first orientation when the +Z1 vector of the Z1 axis and the −g vector of the gravity axis g are aligned, or at least substantially aligned with each other, for example. In certain instances, the processor 3008 can be configured to orient the output display 2250 in the second orientation when the +X1 vector of the X1 axis and the +g vector of the gravity axis g are aligned, or at least substantially aligned with each other, for example. In certain instances, the processor 3008 can be configured to orient the output display 2250 in the third orientation when the +Y1 vector of the Y1 axis and the +g vector of the gravity g axis are aligned, or at least substantially aligned with each other, for example. In certain instances, the processor 3008 can be configured to orient the output display 2250 in the fourth orientation when the +X1 vector of the X1 axis and the −g vector of the gravity axis g are aligned, or at least substantially aligned with each other, for example.

Referring to FIGS. 11-12D, in certain instances, the processor 3008 can be configured to rotate the output display 2250 from the first orientation to the second orientation if the handle 2212 is rotated clockwise about the longitudinal axis LL (FIG. 1) by an angle selected from a range of about 80 degrees, for example, to about 100 degrees, for example. If the handle 2212 is rotated clockwise about the longitudinal axis LL by less than 80 degrees, the processor 3008 may not reorient the output display 2250, in this example. In certain instances, the processor 3008 can be configured to rotate the display 2250 from the first orientation to the fourth orientation if the handle 2212 is rotated counterclockwise about the longitudinal axis LL by an angle selected from a range of about 80 degrees, for example, to about 100 degrees, for example. If the handle 2212 is rotated counterclockwise about the longitudinal axis LL by less than 80 degrees, the processor 3008 may not reorient the output display 2250, in this example.

As described above, the operator may use the rocker 3012 to articulate the end effector 2208, for example. In certain instances, the operator may move their finger in a first direction to tilt the rocker 3012 to depress the dome switch 3004A to articulate the end effector 2208 in a clockwise direction to the right, for example; and the operator may move their finger in a second direction, opposite the first direction, to depress the dome switch 3004B to articulate the end effector 2208 in a counterclockwise direction to the left, for example.

Depending on the position and/or orientation of the rocker 3012 with respect to the interface 3001 and/or the handle assembly 2202, in certain instances, in a first or neutral position of the handle assembly 2202, the first direction can be an upward direction, for example, and the second direction can be a downward direction, for example, as illustrated in FIGS. 1 and 14A. In such instances, the operator of the surgical instrument 2200 may become accustomed to moving their finger up, for example, to articulate the end effector 2208 to the right, for example; and the operator may become accustomed to moving their finger down, for example, to articulate the end effector 2208 to the left, for example. In certain instances, however, the operator may change the position of the handle assembly 2202 to a second position such as an upside down position, for example, as illustrated in FIG. 14B. In such instances, if the operator does not remember to reverse the direction of movement of their finger, the operator may unintentionally articulate the end effector 2208 in an opposite direction to the direction the operator intended.

Figure 13:
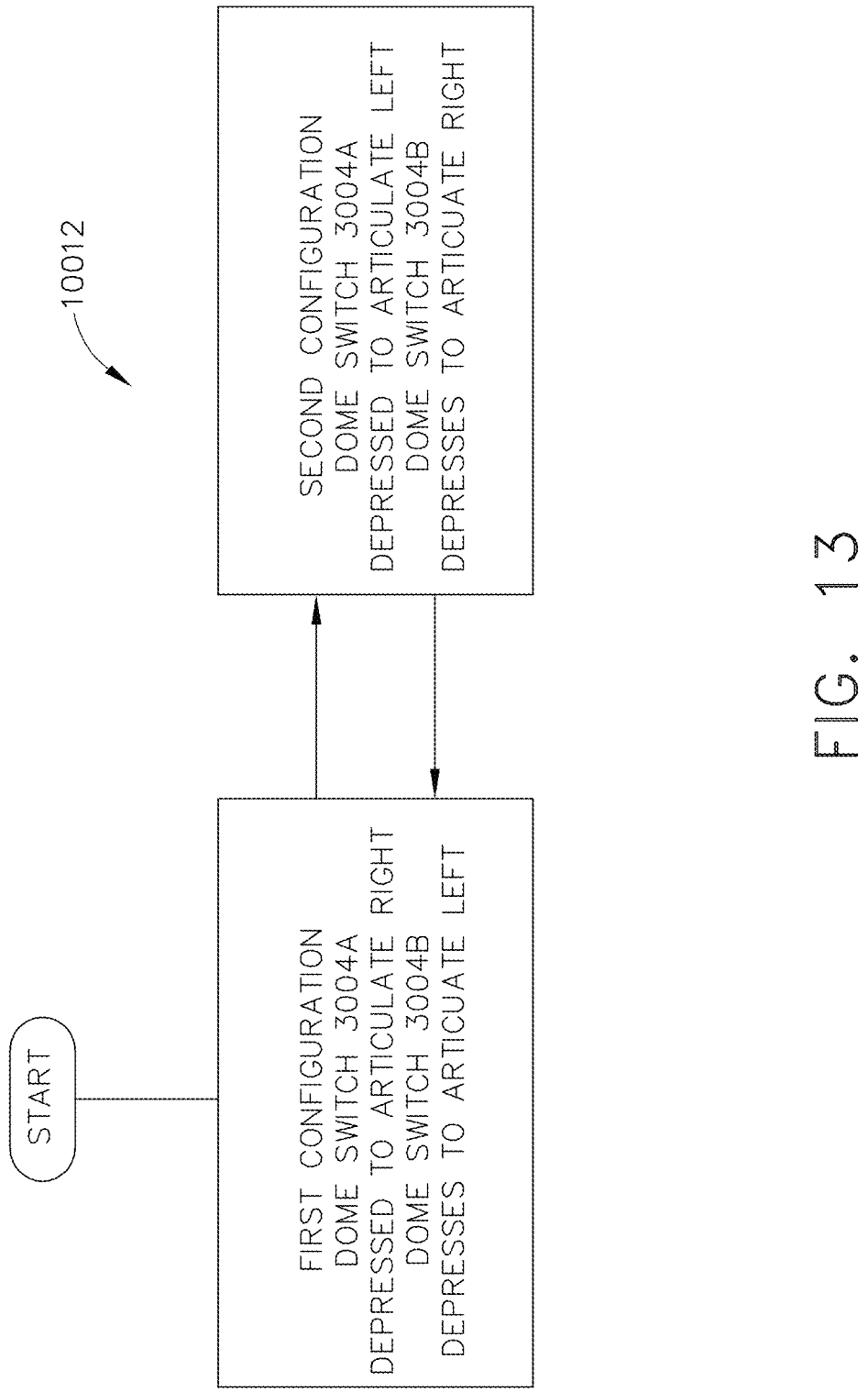
FIG. 13 depicts a module of the surgical instrument of FIG. 1.

Referring to FIG. 13, the surgical instrument 2200 may comprise a module 10012 which may allow the operator to maintain the directions of movement to which a surgeon may have become accustomed with respect to the operation of the surgical instrument 2200. As discussed above, the processor 3008 can be configured to toggle between a plurality of configurations in response to changes in the position and/or orientation of the handle assembly 2202, for example. In certain instances, as illustrated in FIG. 13, the processor 3008 can be configured to toggle between a first configuration of the interface 3001 associated with a first position and/or orientation of the handle assembly 2202, and a second configuration of the interface 3001 associated with a second position and/or orientation of the handle assembly 2202.

In certain instances, in the first configuration, the processor 3008 can be configured to command an articulation motor to articulate the end effector 2208 to the right when the dome switch 3004A is depressed, for example, and the processor 3008 can be configured to command an articulation motor to articulate the end effector 2208 to the left when the dome switch 3004B is depressed, for example. In the second configuration, the processor 3008 can command an articulation motor to articulate the end effector 2208 to the left when the dome switch 3004A is depressed, for example, and the processor 3008 can command an articulation motor to articulate the end effector 2208 to the right when the dome switch 3004B is depressed, for example. In various embodiments, a surgical instrument can comprise one motor to articulate the end effector 2208 in both directions while, in other embodiments, the surgical instrument can comprise a first motor configured to articulate the end effector 2208 in a first direction and a second motor configured to articulate the end effector 2208 in a second direction.

Referring to FIGS. 13-14B, the processor 3008 can be configured to adopt the first configuration while the handle assembly 2202 is in the first position and/or orientation, for example, and adopt the second configuration while the handle assembly 2202 is in the second position and/or orientation, for example. In certain instances, the processor 3008 can be configured to detect the orientation and/or position of the handle assembly 2202 through input from one or more accelerometers (not shown) which can be housed within the handle assembly 2202, for example. Such accelerometers, in various instances, can detect the orientation of the handle assembly 2202 with respect to gravity, i.e., up and/or down.

In certain instances, the processor 3008 can be configured to adopt the first configuration while an angle between a vector D (FIG. 1) extending through the handle assembly 2202 and the gravity vector g is any angle in the range of about 0 degrees, for example, to about 100 degrees, for example. In certain instances, the processor 3008 can be configured to adopt the first configuration while the angle between the vector D and the gravity vector g is any angle in the range of about 0 degrees, for example, to about 90 degrees, for example. In certain instances, the processor 3008 can be configured to adopt the first configuration while the angle between the vector D and the gravity vector g is less than or equal to about 80 degrees, for example.

In certain instances, the processor 3008 can be configured to adopt the second configuration while the angle between the vector D and the gravity vector g is greater than or equal to about 80 degrees, for example. In certain instances, the processor 3008 can be configured to adopt the second configuration while the angle between the vector D and the gravity vector g is greater than or equal to about 90 degrees, for example. In certain instances, the processor 3008 can be configured to adopt the second configuration while the angle between the vector D and the gravity vector g is greater than or equal to about 100 degrees, for example.

The reader will appreciate that the described orientations and/or positions of the handle assembly 2202 and their corresponding configurations which are adopted by the processor 3008 are exemplary in nature and are not intended to limit the scope of the present disclosure. The processor 3008 can be configured to adopt various other configurations in connection with various other orientations and/or positions of the handle assembly 2202.

Referring to FIG. 15, in certain instances, the surgical instrument 2200 can be controlled and/or operated, or at least partially controlled and/or operated, by input from an operator received through a display such as, for example, the display 2250; the display 2250 may comprise a touchscreen adapted to receive the input from the operator which can be in the form of one or more touch gestures. In various instances, the display 2250 may be coupled to a processor such as, for example, the processor 3008 which can be configured to cause the surgical instrument 2200 to perform various functions in response to the touch gestures provided by the operator. In certain instances, the display 2250 may comprise a capacitive touchscreen, a resistive touchscreen, or any suitable touchscreen, for example.

Referring again to FIG. 15, the display 2250 may comprise a plurality of icons which can be associated with a plurality of functions that can be performed by the surgical instrument 2200. In certain instances, the processor 3008 can be configured to cause the surgical instrument 2200 to perform a function when an icon representing such function is selected, touched, and/or pressed by the operator of the surgical instrument 2200. In certain instances, a memory such as, for example, the memory 3010 may comprise one or more modules for associating the plurality of icons with the plurality of functions.

In certain instances, as illustrated in FIG. 15, the display 2250 may include a firing icon 10014, for example. The processor 3008 can be configured to detect a firing input signal when the operator touches and/or presses the firing icon 10014. In response to the detection of the firing input signal, the processor 3008 can be configured to activate the motor 2216 to motivate a firing member of the surgical instrument 2200 to fire the staples from the staple cartridge 10006 and/or cut tissue captured between the anvil 10002 and the staple cartridge 10006, for example. In certain instances, as illustrated in FIG. 15, the display 2250 may include an articulation icon 10016 for articulating the end effector 2208 in a first direction such as, for example, a clockwise direction, for example; the display 2250 may also include an articulation icon 10018 for articulating the end effector 2208 in a second direction such as, for example, a counterclockwise direction. The reader will appreciate that the display 2250 may comprise various other icons associated with various other functions that the processor 3008 may cause the surgical instrument 2200 to perform when such icons are selected, touched, and/or pressed by the operator of the surgical instrument 2200, for example.

In certain instances, one or more of the icons of the display 2250 may comprise words, symbols, and/or images representing the function that can be performed by touching or pressing the icons, for example. In certain instances, the articulation icon 10016 may show an image of the end effector 2208 articulated in the clockwise direction. In certain instances, the articulation icon 10018 may show an image of the end effector 2208 articulated in the counterclockwise direction. In certain instances, the firing icon 10014 may show an image of the staples being fired from the staple cartridge 10006.

Figure 16:
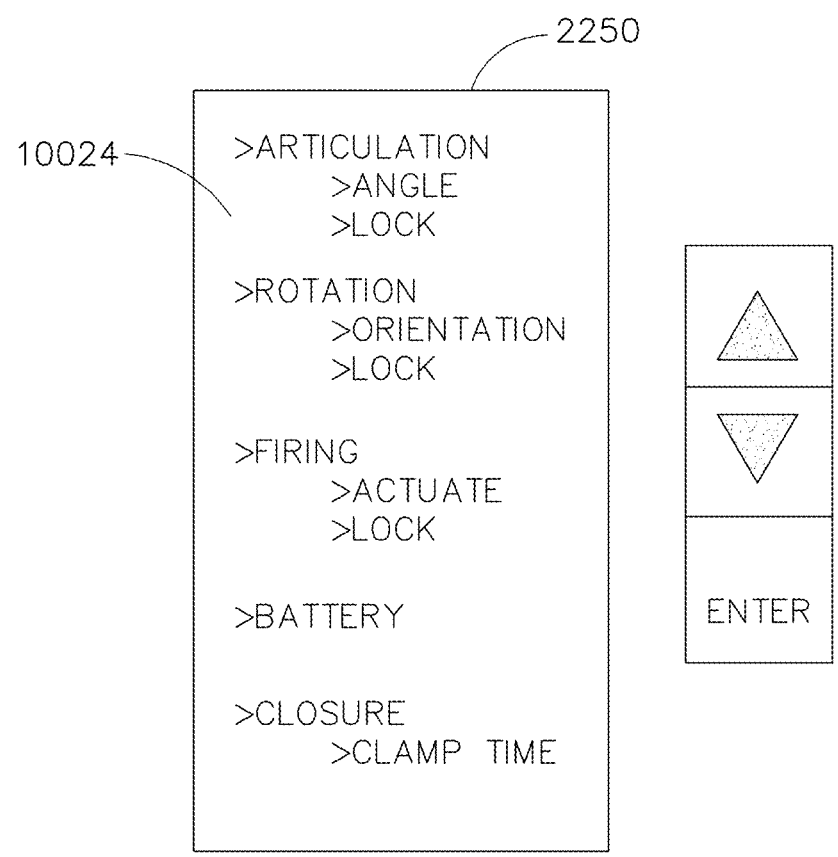
FIG. 16 is a schematic illustration of the display of FIG. 10 showing a navigational menu.
Figure 17:
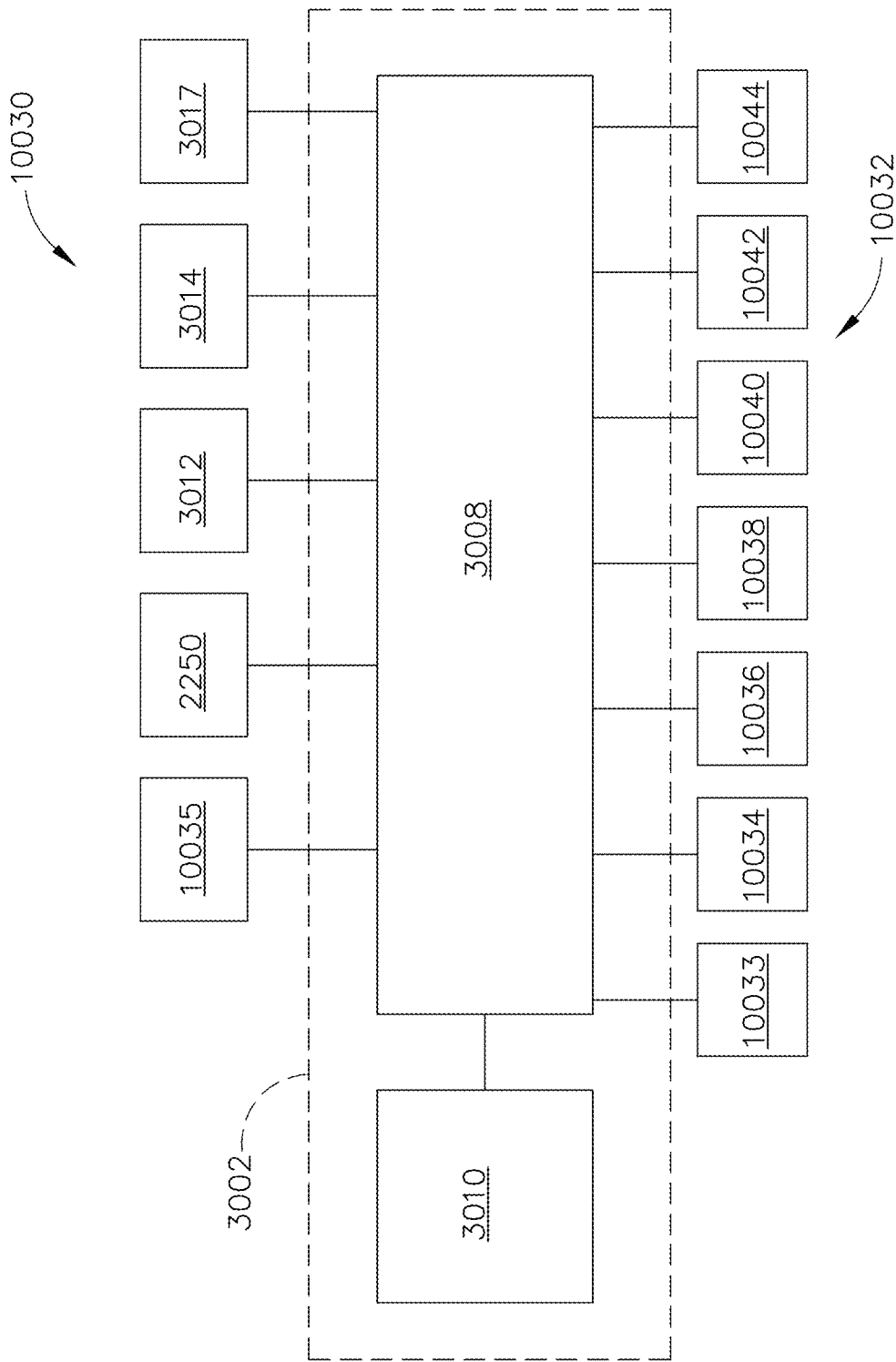
FIG. 17 is a schematic block diagram of an indicator system of the surgical instrument of FIG. 1.

Referring to FIGS. 1 and 16, the interface 3001 of the surgical instrument 2200 may comprise a plurality of operational controls such as, for example, a closure trigger 10020, a rotation knob 10022, the articulation rocker 3012, and/or a firing input 3017 (FIG. 17). In certain instances, various operational controls of the interface 3001 of the surgical instrument 2200 may serve, in addition to their operational functions, as navigational controls. In certain instances, the surgical instrument 2200 may comprise an operational mode and a navigational mode. In the operational mode, some or all of the controls of the surgical instrument 2200 may be configured to perform operational functions; and in the navigational mode, some or all of the controls of the surgical instrument 2200 may be configured to perform navigational functions. In various instances, the navigational functions performed by some or all of the controls of the surgical instrument 2200 can be related to, associated with, and/or connected to the operational functions performed by the controls. In other words, the operational functions performed by the controls of the surgical instrument 2200 may define the navigational functions performed by such controls.

Referring to FIGS. 1 and 16, in certain instances, a processor such as, for example, the processor 3008 can be configured to toggle between a primary interface configuration while the surgical instrument 2200 is in the operational mode and a secondary interface configuration while the surgical instrument 2200 is in the navigational mode; the processor 3008 can be configured to assign operational functions to some or all of the controls of the interface 3001 in the operational mode and assign navigational functions to such controls in the navigational mode, for example. In certain instances, the navigational functions of the controls in the secondary interface configuration are defined by the operational functions of the controls in the primary interface configuration, for example.

Referring to FIGS. 16, in certain instances, the operator of the surgical instrument 2200 may activate the navigational mode by opening or activating a navigational menu 10024 in the display 2250, for example. In certain instances, the surgical instrument 2200 may comprise a navigational mode button or a switch (not shown) for activating the navigational mode. In any event, the processor 3008 may switch the controls of the interface 3001 from the primary interface configuration to the secondary interface configuration upon receiving a navigational mode input signal.

As illustrated in FIG. 16, the navigational menu 10024 may comprise various selectable categories, menus, and/or folders and/or various subcategories, sub-menus, and/or subfolders. In certain instances, the navigational menu 10024 may comprise an articulation category, a firing category, a closure category, a battery category and/or, rotation category, for example.

In certain instances, the articulation rocker 3012 can be utilized to articulate the end effector 2208, in the operational mode, as described above, and can be utilized to select the articulation category, and/or launch and/or navigate an articulation menu in the navigational mode, for example. In certain instances, the firing input 3017 (FIG. 17) can be utilized to fire the staples, in the operational mode, as described above, and can be utilized to select the firing category, and/or launch and/or navigate a firing menu in the navigational mode, for example. In certain instances, the closure trigger 10020 can be utilized to transition the end effector 2208 between an open configuration and an approximated configuration in the operational mode, as described above, and can be utilized to select the closure category, and/or launch and/or navigate a closure menu in the navigational mode, for example. In certain instances, the rotation knob 10022 can be utilized to rotate the end effector 2208 relative to the elongate shaft 2204 in the operational mode, and can be utilized to select the rotation category, and/or launch and/or navigate a rotation menu in the navigational mode, for example.

Referring primarily to FIGS. 1 and 17, the operation of the surgical instrument 2200 may involve a series or a sequence of steps, actions, events, and/or combinations thereof. In various circumstances, as illustrated in FIG. 17, the surgical instrument 2200 may include an indicator system 10030 which can be configured to guide, alert, and/or provide feedback to the operator of the surgical instrument 2200 with respect to the various steps, actions, and/or events.

In various instances, the indicator system 10030 may include a plurality of indicators 10032. In certain instances, the indicators 10032 may comprise, for example, visual indicators such as a display screens, backlights, and/or LEDs, for example. In certain instances, the indicators 10032 may comprise audio indicators such as speakers and/or buzzers, for example. In certain instances, the indicators 10032 may comprise tactile indicators such as haptic actuators, for example. In certain instances, the indicators 10032 may comprise combinations of visual indicators, audio indicators, and/or tactile indicators, for example.

Referring to FIG. 17, the indicator system 10030 may include one or more microcontrollers such as, for example, the microcontroller 3002 which may comprise one or more processors such as, for example, the processor 3008 and/or one or more memory units such as, fore example, the memory 3010. In various instances, the processor 3008 may be coupled to various sensors 10035 and/or feedback systems which may be configured to provide feedback to the processor 3008 regarding the status of the surgical instrument 2200 and/or the progress of the steps, actions, and/or events pertaining to the operation of the surgical instrument 2200, for example.

In various instances, the operation of the surgical instrument 2200 may include various steps including an articulation step, a closure step, a firing step, a firing reset step, a closure reset step, an articulation reset step, and/or combinations thereof, for example. In various instances, the articulation step may involve articulating the end effector 2208 relative to the elongate shaft 2204 to an articulated position, for example; and the articulation reset step may involve returning the end effector 2208 to an articulation home state position, for example. In various instances, the closure step may involve transitioning the end effector 2208 to a closed configuration, for example; and the closure reset step may involve transitioning the end effector 2208 to an open configuration, for example. In various instances, the firing step may involve advancing a firing member to deploy staples from the staple cartridge 10006 and/or cut tissue captured by the end effector 2208, for example. In various instances, the firing reset step may involve retraction of the firing member to a firing home state position, for example.

Referring to FIG. 17, one or more of the indicators 10032 of the indicator system 10030 can be associated with one or more of the various steps performed in connection with the operation of the surgical instrument 2200. In various instances, as illustrated in FIG. 17, the indicators 10032 may include a bailout indicator 10033 associated with the bailout assembly 2228, an articulation indicator 10034 associated with the articulation step, a closure indicator 10036 associated with the closure step, a firing indicator 10038 associated with the firing step, an articulation reset indicator 10040 associated with the articulation reset step, a closure reset indicator 10042 associated with the closure reset step, and/or a firing reset indicator 10044 associated with the firing reset step, for example. The reader will appreciate that the above described steps and/or indicators are exemplary in nature and are not intended to limit the scope of the present disclosure. Various other steps and/or indicators are contemplated by the present disclosure.

Referring to FIG. 1, in various instances, one or more of the controls of the interface 3001 can be employed in one or more of the steps of operation of the surgical instrument 2200. In certain instances, the closure trigger 10020 can be employed in the closure step, for example. In certain instance, the firing input 3017 (FIG. 17) can be employed in the firing step, for example. In certain instances, the articulation rocker 3012 can be employed in the articulation step and/or the articulation reset step, for example. In certain instances, the home state input 3014 can be employed in the firing reset step, for example.

Referring to FIG. 17, in various instances, the indicators 10032 associated with one of the steps of operation of the surgical instrument 10030 may also be associated with the controls employed in such steps. For example, the articulation indicator 10034 can be associated with the articulation rocker 3012, the closure indicator 10036 can be associated with the closure trigger 10020, the firing indicator 10038 can be associated with the firing input 3017, and/or the firing reset indicator 10044 can be associated with the home state input 3014. In certain instances, associating an indicator with a control of the interface 3001 may include placing or positioning the indicator on, within, partially within, near, and/or in close proximity to the control, for example, to aid the operator in associating the indicator with the control. The reader will appreciate that the above described controls and/or the indicators associated with such controls are exemplary in nature and are not intended to limit the scope of the present disclosure. Various other controls and the indicators associated with such controls are contemplated by the present disclosure.

In various instances, the processor 3008 can be configured to activate the indicators 10032 in one or more sequences defined by the order of the steps associated with the indicators 10032. For example, the operator may need to operate the surgical instrument 2200 in a series of steps starting with the articulation step followed by the closure step, and further followed by the firing step. In such example, the processor 3008 can be configured to guide the operator through the sequence of steps by activating the corresponding articulation indicator 10034, closure indicator 10036, and firing indicator 10038 in the same order as the order of the steps. In other words, the processor 3008 can be configured to first activate the articulation indicator 10034 followed by the closure indicator 10036, and further followed by the firing indicator 10038, for example. In certain instances, the surgical instrument 2200 may comprise a bypass switch (not shown) which may be configured to allow the operator to bypass a step that is recommended but not required, for example. In such instances, pressing the bypass switch may signal the processor 3008 to activate the next indicator in the sequence.

In various instances, the processor 3008 can be configured to toggle the indicators 10032 between a plurality of indicator configurations to guide, alert, and/or provide feedback to the operator of the surgical instrument 2200. In various instances, the processor 3008 may provide visual cues to the operator of the surgical instrument 2200 by the toggling of the indicators 10032 between the plurality of indicator configurations which may include activated and/or deactivated configurations, for example. In certain instances, one or more of the indicators 10032 may comprise a light source which can be activated in a first indicator configuration, for example, to alert the operator to perform a step associated with the indicators 10032, for example; and the light source can be deactivated in a second indicator configuration, for example, to alert the operator when the step is completed, for example.

In certain instances, the light source can be a blinking light which can be transitioned by the processor 3008 between a blinking configuration and a non-blinking configuration. In certain instances, the blinking light, in the non-blinking configuration, may be transitioned to solid illumination or turned off, for example. In certain instances, the blinking light, in the blinking configuration, may represent a waiting period while a step is in progress, for example. In certain instances, the blinking frequency of the blinking light may be changed to provide various visual cues. For example, the blinking frequency of the blinking light that represents a waiting period may be increased or decreased as the waiting period approaches its completion. The reader will appreciate that the waiting period can be a forced waiting period and/or a recommended waiting period, for example. In certain instances, forced waiting periods can be represented by a blinking configuration different from recommended waiting periods. In certain instances, the blinking light may comprise a first color representing a forced waiting period and a second color representing a recommended waiting period, wherein the first color is different from the second color. In certain instances, the first color can be a red color, for example, and the second color can be a yellow color, for example.

In various instances, one or more of the indicators 10032 can be toggled by the processor 3008 between a first indicator configuration representing controls that are available for use in a standard next step of the steps of operation of the surgical instrument 2200, a second indicator configuration representing controls that are available for use in a non-standard next step of the steps of operation of the surgical instrument 2200, and/or a third indicator configuration representing controls that are not available for use in a next step of the steps of operation of the surgical instrument 2200, for example. For instance, when the end effector 2208 of the surgical instrument 2000 is in an open configuration, the articulation indicator 10034 and the closure indicator 10036 can be illuminated indicating to the operator of the surgical instrument 2200 that those two functions, i.e., end effector articulation and end effector closure, are available to the operator at that moment. In such a state, the firing indicator 10038 may not be illuminated indicating to the operator that the firing function is not available to the operator at that moment. Once the end effector 2208 has been placed in a closed and/or clamped configuration, the articulation indicator 10034 may be deilluminated indicating to the operator that the articulation function is no longer available at that moment. In such a state, the illumination of the closure indicator 10036 may be reduced indicating to the operator that the closing function can be reversed at that moment. Moreover, in such a state, the firing indicator 10038 can become illuminated indicating to the operator that the firing function is available to the operator at that moment. Once the firing member has been at least partially advanced, the closure indicator 10036 may be deilluminated indicating that the closing function cannot be reversed at that moment. When the firing member is retracted back to its unfired position, the illumination of the firing indicator 10038 may be reduced indicating to the operator that the firing member can be readvanced, if needed. Alternatively, once the firing member has been retracted, the firing indicator 10038 may be deilluminated indicating to the operator that the firing member cannot be readvanced at that moment. In either event, the closure indicator 10036 can be reilluminated after the firing member has been retracted back to its unfired position indicating to the operator that the closing function can be reversed at that moment. The articulation indicator 10034 may remain deilluminated indicating that the articulation function is not available at that moment. Once the end effector 2208 has been opened, the firing indicator 10038 can be deilluminated, if it hadn't been deilluminated already, indicating to the operator that the firing function is not available at that moment, the closing indicator 10036 can remain illuminated or its illumination can be reduced indicating to the operator that the closing function is still available at that moment, and the articulation indicator 10034 can be reilluminated indicating to the operator that the articulation function is available at that moment. The example provided above is exemplary and other embodiments are possible.

In certain instances, the one or more of the indicators 10032 may include a light source that can be toggled by the processor 3008 between a first color in the first indicator configuration, a second color in the second indicator configuration, and/or a third color in the third indicator configuration, for example. In certain instances, the indicators 10032 can be toggled by the processor 3008 between the first indicator configuration, the second indicator configuration, and/or the third indicator configuration by changing the light intensity of the light source or scanning through the color spectrum, for example. In certain instances, the first indicator configuration may comprise a first light intensity, for example, the second indicator configuration may comprise a second light intensity, for example, and/or the third indicator configuration may comprise a third indicator configuration, for example.

In various instances, in the firing step of operation of the surgical instrument 2200, the firing member can be motivated to deploy the plurality of staples from the staple cartridge 10006 into tissue captured between the anvil 10002 and the staple cartridge 10006, and advance a cutting member (not shown) to cut the captured tissue. The reader will appreciate that advancing the cutting member to cut the captured tissue in the absence of a staple cartridge or in the presence of a spent staple cartridge may be undesirable. Accordingly, in various instances, the surgical instrument 2200 may comprise a lockout mechanism (not shown) which can be activated to prevent advancement of the cutting member in the absence of a staple cartridge or in the presence of a spent staple cartridge, for example.

Figure 18:
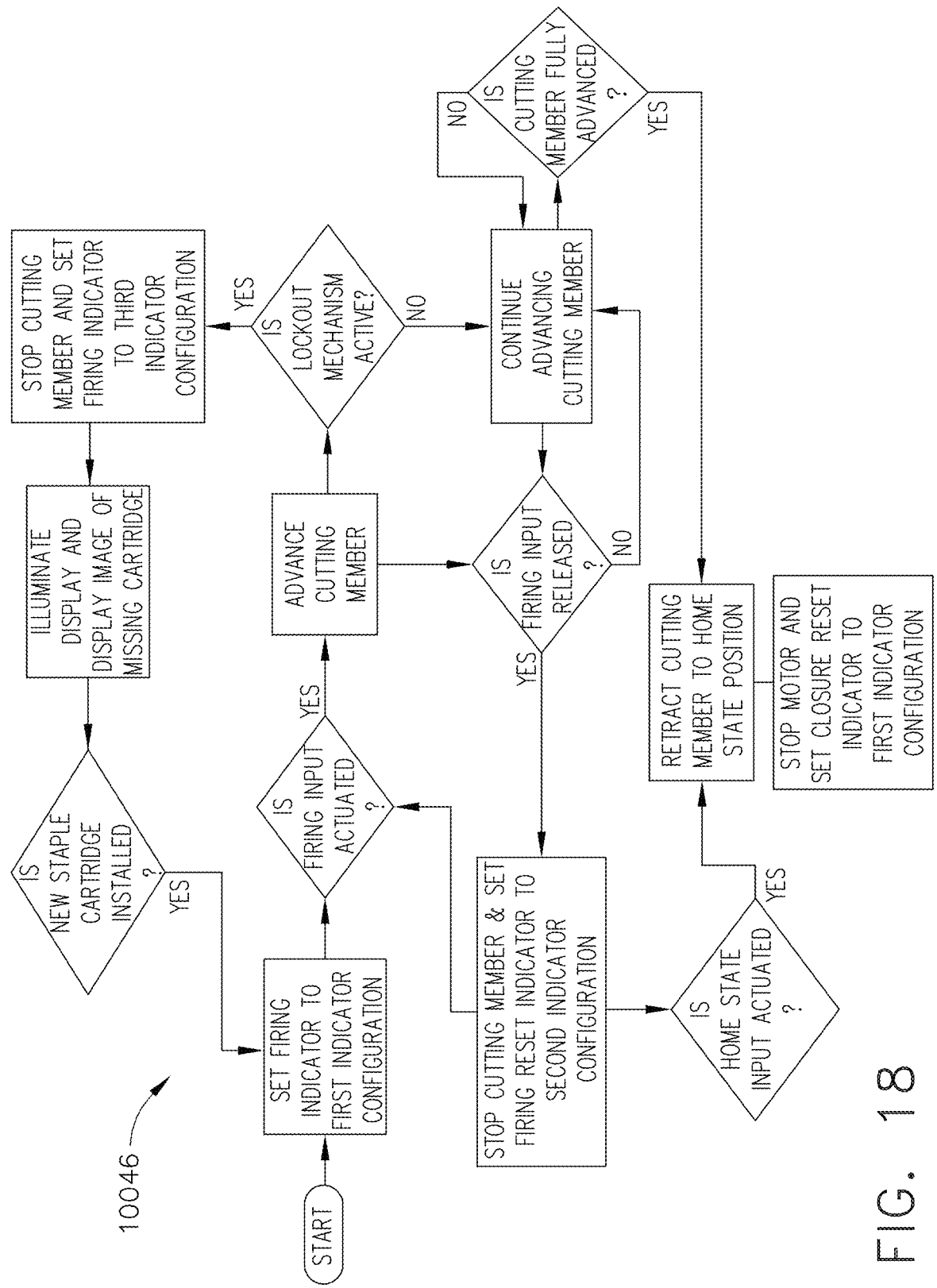
FIG. 18 is a module of the surgical instrument of FIG. 1.

Referring to FIG. 18, a module 10046 can be employed by an indicator system such as, for example, the indicator system 10030 (FIG. 17). In various instances, the module 10046 may comprise program instructions stored in one or more memory units such as, for example, the memory 3010, which when executed may cause the processor 3008 to employ the indicators 10032 to alert, guide, and/or provide feedback to the operator of the surgical instrument 2200 during the firing step of operation of the surgical instrument 2200, for example. In certain instances, one or more of the indicators 10032 such as the firing indicator 10038 and/or the firing reset indicator 10044, for example, can be toggled by the processor 3008 between the first indicator configuration, the second indicator configuration, and/or the third indicator configuration to alert, guide, and/or provide feedback to the operator of the surgical instrument 2200 during the firing step of operation of the surgical instrument 2200, for example.

Referring to FIGS. 17 and 18, the operator of the surgical instrument 2200 may actuate the firing input 3017 to cause the processor 3008 to activate the motor 2216, for example, to motivate the firing member to deploy the plurality of staples from the staple cartridge 10006 into the captured tissue and advance the cutting member to cut the captured tissue. In certain instances, the firing indicator 10038 can be set to the first indicator configuration to alert the operator that the firing input 3017 is available for use and/or is one of the standard control options available for completion of the firing step.

In certain instances, as illustrated in FIGS. 17 and 18, if the processor 3008 detects that the lockout mechanism is active, the processor 3008 may stop the advancement of the cutting member by stopping and/or deactivating the motor 2216, for example. In addition, the processor 3008 can be configured to transition the firing indicator 10038 from the first indicator configuration to the third indicator configuration to caution the operator that the firing input 3017 is not available for use. In certain instances, the processor 3008 may also be configured to illuminate the display 2250 and display an image of a missing staple cartridge, for example. In certain instances, the processor 3008 may also set the firing reset indicator 10044 to the first indicator configuration, for example, to inform the operator that home state input 3014 is available for use to motivate the firing member to retract the cutting member to the firing home state position, for example. In certain instances, the processor 3008 can be configured to detect the installation of a new staple cartridge, through the sensors 10035 for example, and in response, return the firing indicator 10038 to the first indicator configuration, for example.

In certain instances, as illustrated in FIG. 18, if the operator releases the firing input 3017 before completion of the firing step, the processor 3008 can be configured to stop the motor 2216. In certain instances, the processor 3008 may also maintain the firing indicator 10038 in the first indicator configuration, for example, to alert the operator that the firing input 3017 is available for use as the standard control option available for completion of the firing step of operation of the surgical instrument 2200, for example. In certain instances, the processor 3008 may also set the firing reset indicator 10044 to the second indicator configuration, for example, to inform the operator that home state input 3014 is available for use as a non-standard control option available for use to retract the cutting member to the firing home state position, for example, if the operator decides to abort the firing step of operation of the surgical instrument 2200, for example.

Further to the above, as illustrated in FIG. 18, if the firing input 3017 is re-actuated by the operator, the processor 3008 may, in response, reactivate the motor 2216 to continue advancing the cutting member until the cutting member is fully advanced. In certain instances, the processor 3008 may employ the sensors 10035 to detect when the cutting member is fully advanced; the processor 3008 may then reverse the direction of rotation of the motor 2216, for example, to motivate the firing member to retract the cutting member to the firing home state position, for example. In certain instances, the processor 3008 can be configured to stop the motor 2216, for example, and/or set the closure reset indicator 10042 to the first indicator configuration, for example, if the processor detects that the cutting member has reached the firing home state position, for example.

As described herein, a surgical instrument can enter into various operational states, modes, and/or configurations. In certain instances, the instrument may enter into an operational state, mode, and/or configuration that is undesired by the operator who may be unsure as to how to remove the instrument from that undesired state, mode, and/or configuration. In at least one instance, the surgical instrument can include a reset button which, when actuated, can place the instrument in a default state, mode, and/or configuration. For instance, the default state, mode, and/or configuration can comprise an operational mode, and not a navigational mode. In at least one instance, the default state and/or configuration can comprise a certain orientation of the display output 2250, for example. The reset button can be in signal communication with the processor 3008 which can place the surgical instrument in the default state, mode, and/or configuration. In certain instances, the processor 3008 can be configured to hold the surgical instrument in the default state, mode, and/or configuration. In at least one instance, the surgical instrument can include a lock button which, when actuated, can lock the surgical instrument in its default state, mode, and/or configuration. In certain instance, a lock button can lock the surgical instrument in its current state, mode, and/or configuration. The operational state, mode, and/or configuration can be unlocked by actuating the lock button once again. In various embodiments, the surgical instrument can include at least one accelerometer in signal communication with the processor 3008 which can determine when the instrument handle is being shaken or being moved back and forth quickly. When such shaking is sensed, the processor 3008 can place the surgical instrument into a default operation state, mode, and/or configuration.

Figure 19:
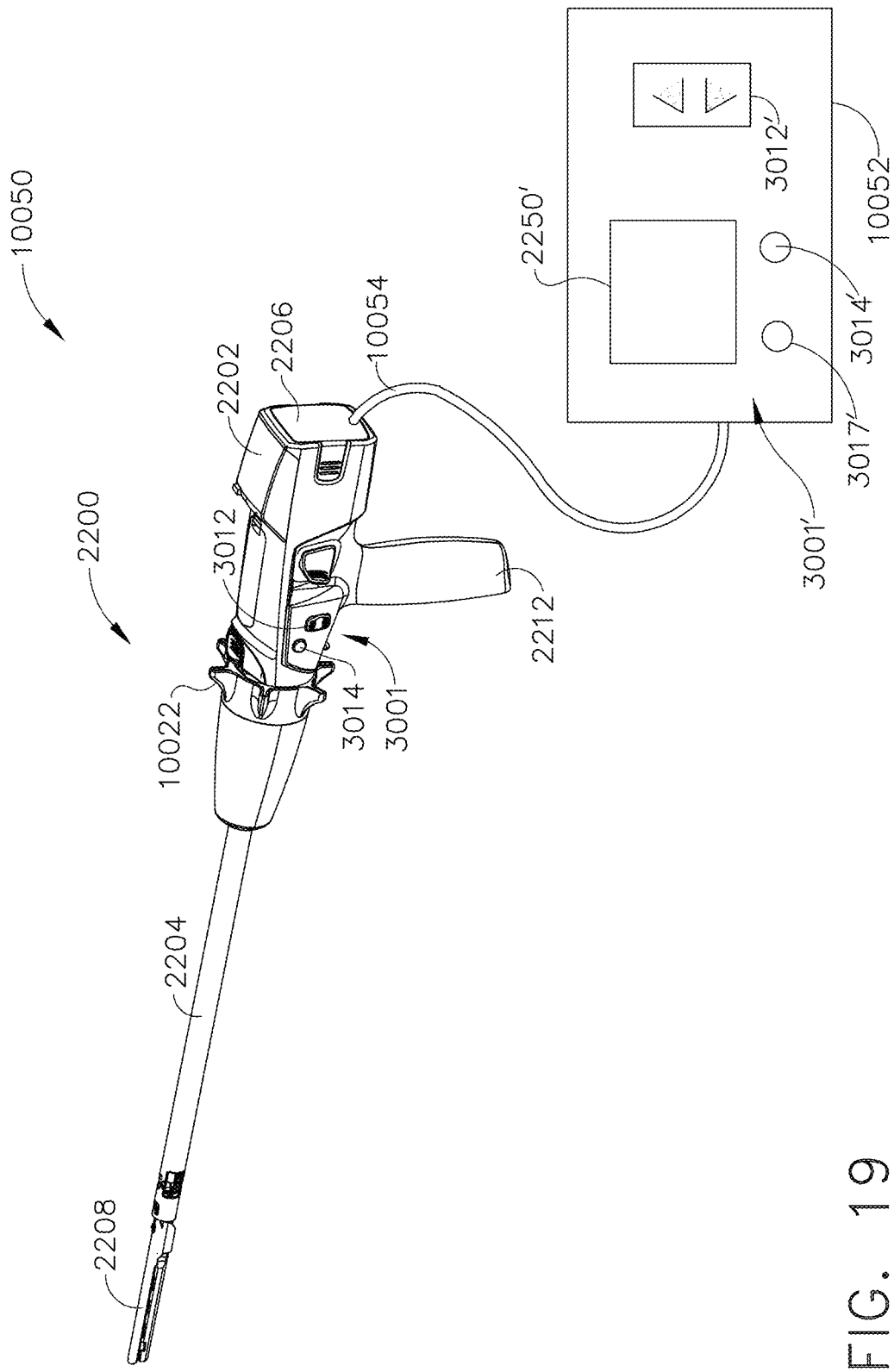
FIG. 19 is a perspective view of the surgical instrument of FIG. 1 coupled to a remote operating unit.

Referring to FIG. 19, in various instances, a surgical assembly 10050 may include a surgical instrument such as, for example, the surgical instrument 2200 and a remote operating unit 10052. In certain instances, the surgical instrument 2200 may comprise a primary interface such as, for example, the interface 3001 which may reside in the handle assembly 2202, as illustrated in FIG. 1. In certain instances, the interface 3001 may include a plurality of primary controls such as, for example, the closure trigger 10020 (FIG. 1), the rotation knob 10022, the articulation rocker 3012, the home state input 3014, and/or the firing input 3017 (FIG. 17).

In various instances, an operator of the surgical instrument 2200 may manually operate the primary controls of the interface 3001 to perform a surgical procedure, for example. As described above, the operator may actuate the articulation rocker 3012 to activate the motor 2216 to articulate the end effector 2208 between an unarticulated position and an articulated position, for example. In certain instances, the operator may actuate the closure trigger 10020 to transition the end effector 2208 between an open configuration and a closed configuration, for example. In certain instances, the operator may actuate the firing input 3017 to activate the motor 2216 to motivate the firing member of the surgical instrument 2200 to fire the staples from the staple cartridge 10006 and/or cut tissue captured between the anvil 10002 and the staple cartridge 10006, for example.

In various instances, the operator of the surgical instrument 2200 may not be sufficiently close in proximity to the handle assembly 2202 to be able to manually operate the interface 3001. For example, the operator may operate the surgical instrument 2200 together with a robotically-controlled surgical system, which may be controlled from a remote location. In such instances, the operator may need to operate the surgical instrument 2200 from the remote location where the operator operates the robotically-controlled surgical system, for example; the operator may employ the remote operating unit 10052 to operate the surgical instrument 2200 remotely, for example. Various robotic systems, instruments, components, and methods are disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, which is incorporated by reference herein in its entirety.

Figure 20:
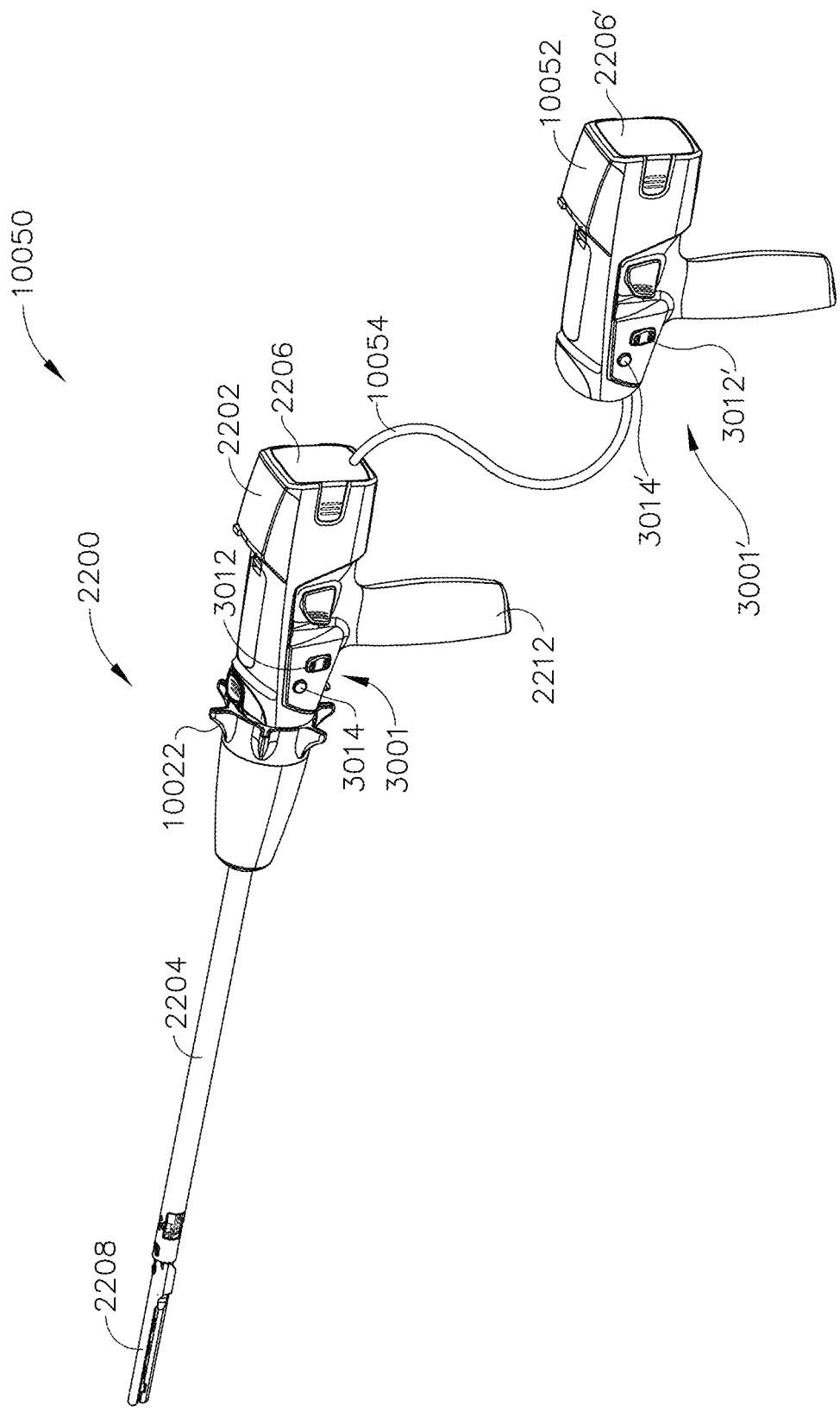
FIG. 20 is a perspective view of the surgical instrument of FIG. 1 coupled to a remote operating unit.

Referring to FIGS. 19 and 20, the remote operating unit 10052 may include a secondary interface 3001', a display 2250', and/or a power assembly 2206' (or "power source" or "power pack"), for example. In various instances, the secondary interface 3001' may include a plurality of secondary controls which may correspond to the primary controls of the primary interface 3001'. In certain instances, the remote operating unit 10052 may include a remote articulation rocker 3012' corresponding to the articulation rocker 3012, for example. In certain instances, the remote operating unit 10052 may include a remote firing input 3017' corresponding to the firing input 3017 of the surgical instrument 2200, for example. In certain instances, the remote operating unit 10052 may include a remote home state input 3014' corresponding to the home state input 3014 of the surgical instrument 2200, for example.

In certain instances, as illustrated in FIG. 19, the remote operating unit 10052, the interface 3001', and/or the plurality of secondary controls may comprise a different shape and/or design from the handle assembly 2202, the interface 3001, and/or the plurality of primary controls, respectively. In certain instances, as illustrated in FIG. 20, the remote operating unit 10052, the interface 3001', and/or the plurality of secondary controls may comprise the same, or at least substantially the same, shape and/or design to the handle assembly 2202, the interface 3001, and/or the plurality of primary controls, respectively.

Figure 21:
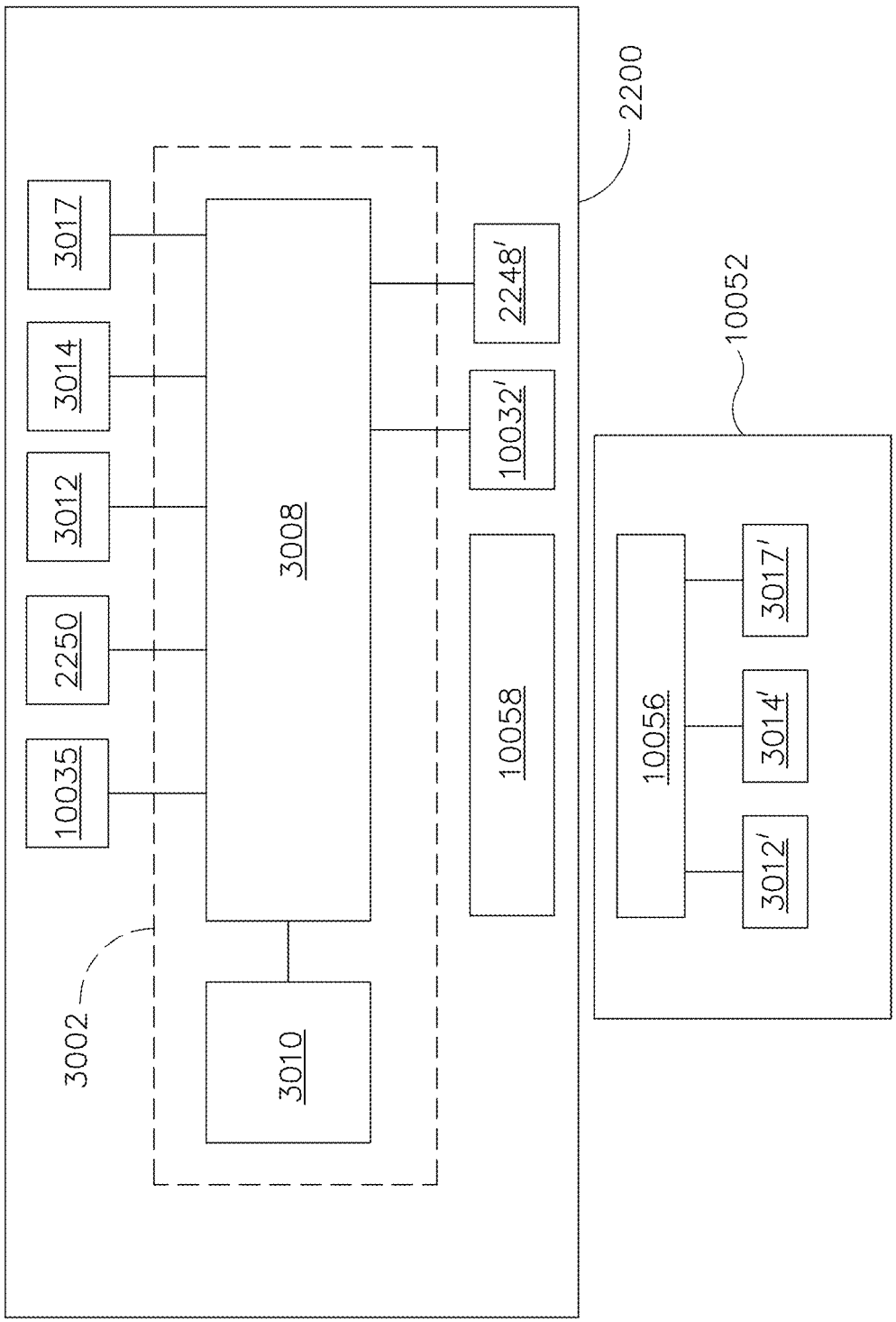
FIG. 21 is a schematic block diagram of the surgical instrument of FIG. 1 in wireless communication with a remote operating unit.

In various instances, as illustrated in FIGS. 19 and 20, the remote operating unit 10052 can be coupled to the handle assembly 2202 of the surgical instrument 2200 via an elongate flexible cable 10054, for example, which can be configured to transmit various actuation signals to the processor 3008 of the surgical instrument 2200, for example; the various actuation signals can be generated by actuating the plurality of secondary controls of the interface 3001', for example. In certain instances, as illustrated in FIG. 21, the remote operating unit 10052 may comprise a transmitter 10056 which can be configured to wirelessly transmit the actuation signals generated by the secondary controls of the secondary interface 3001' from the remote operating unit 10052 to the processor 3001, for example, through a receiver 10058 which can be located in the handle assembly 2202, for example.

In various instances, the surgical instrument 2200 and/or the remote operating unit 10052 may include communication activation inputs (not shown). In certain instances, actuating the communication activation inputs may be a precursory step to establishing communication between the surgical instrument 2200 and the remote operating unit 10052, for example; once communication is established, the operator may employ the remote operating unit 10052 to remotely control the surgical instrument 2200, for example.

In various instances, the memory 3010 may include program instructions for a puppet mode, which when executed may cause the processor 3008 to respond to the actuation signals generated by the plurality of secondary controls of the secondary interface 3001' in the same, or at least similar, manner to the response of the processor 3008 to the actuation signals generated by the plurality of primary controls of the primary interface 3001. In other words, the responses of the processor 3008 to the actuation signals generated by the plurality of secondary controls can be configured to mimic the responses of the processor 3008 to the actuation signals generated by the plurality of primary controls, for example.

In certain instances, actuation of the remote firing input 3017' may solicit the same, or at least a similar, response from the processor 3008 as the actuation of the firing input 3017; the solicited response may include activation of the motor 2216 to motivate the firing member to fire the staples from the staple cartridge 10006 and/or cut tissue captured between the anvil 10002 and the staple cartridge 10006, for example. In certain instances, actuation of the remote articulation rocker 3012' may solicit the same, or at least a similar, response from the processor 3008 as the actuation of the articulation rocker 3012; the solicited response may include activation of the motor 2216 to articulate the end effector 2208 relative to the elongate shaft 2204, for example.

In certain instances, the processor 3008 can be configured to require input actuation signals from both of the primary controls of the primary interface 3001 and the corresponding secondary controls of the secondary interface 3001' to perform the function solicited by such controls. In such instances, the remote operator of the remote operating unit 10052 may need the assistance of an additional operator who can be employed to manually actuate the primary controls of the primary interface 3001 while the remote operator actuates the secondary controls of the secondary interface 3001', for example.

In various instances, as described above, an operator may operate the surgical instrument 2200 together with a robotically-controlled surgical system, which may be controlled by a robotic control system from a remote location. In certain instances, the remote operating unit 10052 can be configured to work in tandem with the robotic control system. In certain instances, the robotic control system may include one or more control ports; and the remote operating unit 10052 may comprise connection means for coupling engagement with the control ports of the robotic control system. In such instances, the operator may operate the surgical instrument 2200 through an interface of the robotic control system, for example. In various instances, the control ports may comprise unique mechanical and/or electrical configurations which may require the use of original equipment manufacturer components to ensure consistent product quality and performance, for example.

In various instances, the remote operating unit 10052 may include various indicators 10032' which can be similar in many respects to the indicators 10032 of the handle assembly 2202. In certain instances, the indicators 10032' of the remote operating unit 10052 can be employed by the processor 3008 in the same, or at least substantially the same, manner as the indicators 10032 to guide, alert, and/or provide feedback to the operator with respect to the various steps of operation of the surgical instrument 2200.

In various instances, the remote operating unit 10052 may include various feedback devices 2248' which can be similar in many respects to the feedback devices 2248 of the handle assembly 2202. In certain instances, the feedback devices 2248' of the remote operating unit 10052 can be employed by the processor 3008 in the same, or at least substantially the same, manner as the feedback devices 2248 to provide sensory feedback to the operator with respect to the various steps of operation of the surgical instrument 2200. Similar to the feedback devices 2248, the feedback devices 2248' may include, for example, visual feedback devices, audio feedback devices, tactile feedback devices, and/or combinations thereof.

Figure 22:
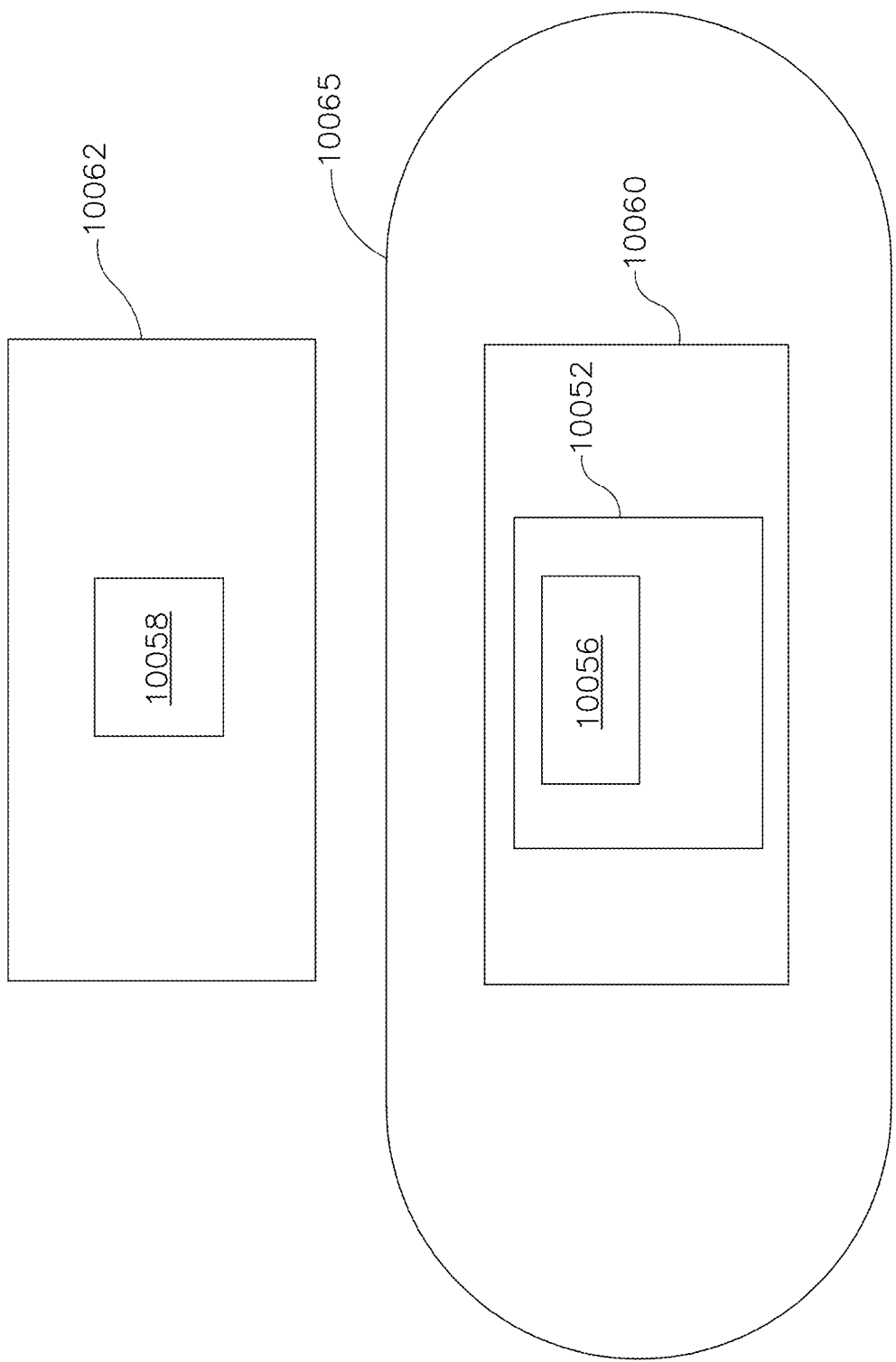
FIG. 22 is a schematic illustration of a first surgical instrument including a remote operating unit for controlling a second surgical instrument.

In various instances, as illustrated in FIG. 22, the remote operating unit 10052 can be included or integrated with a first surgical instrument 10060 and can be utilized to operate a second surgical instrument 10062, for example. In certain instances, the first surgical instrument 10060 can reside in a surgical field 10065 and can be manually operated by the operator from within the surgical field 10065, for example; and the second surgical instrument 10062 can reside outside the surgical field 10065. In certain instances, to avoid exiting the surgical field 10065, the operator may use the remote operating unit 10052 to remotely operate the second surgical instrument 10062 from within the surgical field 10065, for example. In certain instances, the second surgical instrument 10062 may be a circular stapler, for example. The entire disclosure of U.S. Pat. No. 8,360,297, entitled SURGICAL CUTTING AND STAPLING INSTRUMENT WITH SELF ADJUSTING ANVIL, which issued on Jan. 29, 2013, is incorporated by reference herein.

In various instances, the first surgical instrument 10060 and/or the second surgical instrument 10062 may include communication activation inputs (not shown). In such instances, actuating the communication activation inputs may be a precursory step to establishing communication between the first surgical instrument 10060 and the second surgical instrument 10062, for example; once communication is established, the operator may employ the remote operating unit 10052 to remotely control the second surgical instrument 10062, for example.

In various instances, a surgical system can include modular components that can be attached and/or combined together to form a surgical instrument. In certain instances, the modular components can be designed, manufactured, programmed, and/or updated at different times and/or in accordance with different software and/or firmware revisions and updates. For example, referring primarily to FIGS. 23 and 24, a surgical instrument 100 can include a first modular component 110, such as a handle, for example, and a second modular component 120, such as a shaft 122 and an end effector 124, for example, which are described in greater detail herein. In various circumstances, the first modular component 110 and the second modular component 120 can be assembled together to form the modular surgical instrument 100 or at least a portion thereof. Optionally, a different modular component may be coupled to the first modular component 110, such as shaft having different dimensions and/or features than those of the second modular component 120, for example. In various instances, the surgical instrument can include additional modular components, such as a modular battery, for example. Components of the modular surgical instrument 100 can include a control system that is designed and configured to control various elements and/or functions of the surgical instrument 100. For example, the first modular component 110 and the second modular component 120 can each comprise a control system, and the control systems of each modular component 110, 120 can communicate and/or cooperate. In various instances, the first modular component 110 may have been designed, manufactured, programmed, and/or updated at a different time and/or with different software and/or firmware than the second modular component 120, for example.

Figure 25:
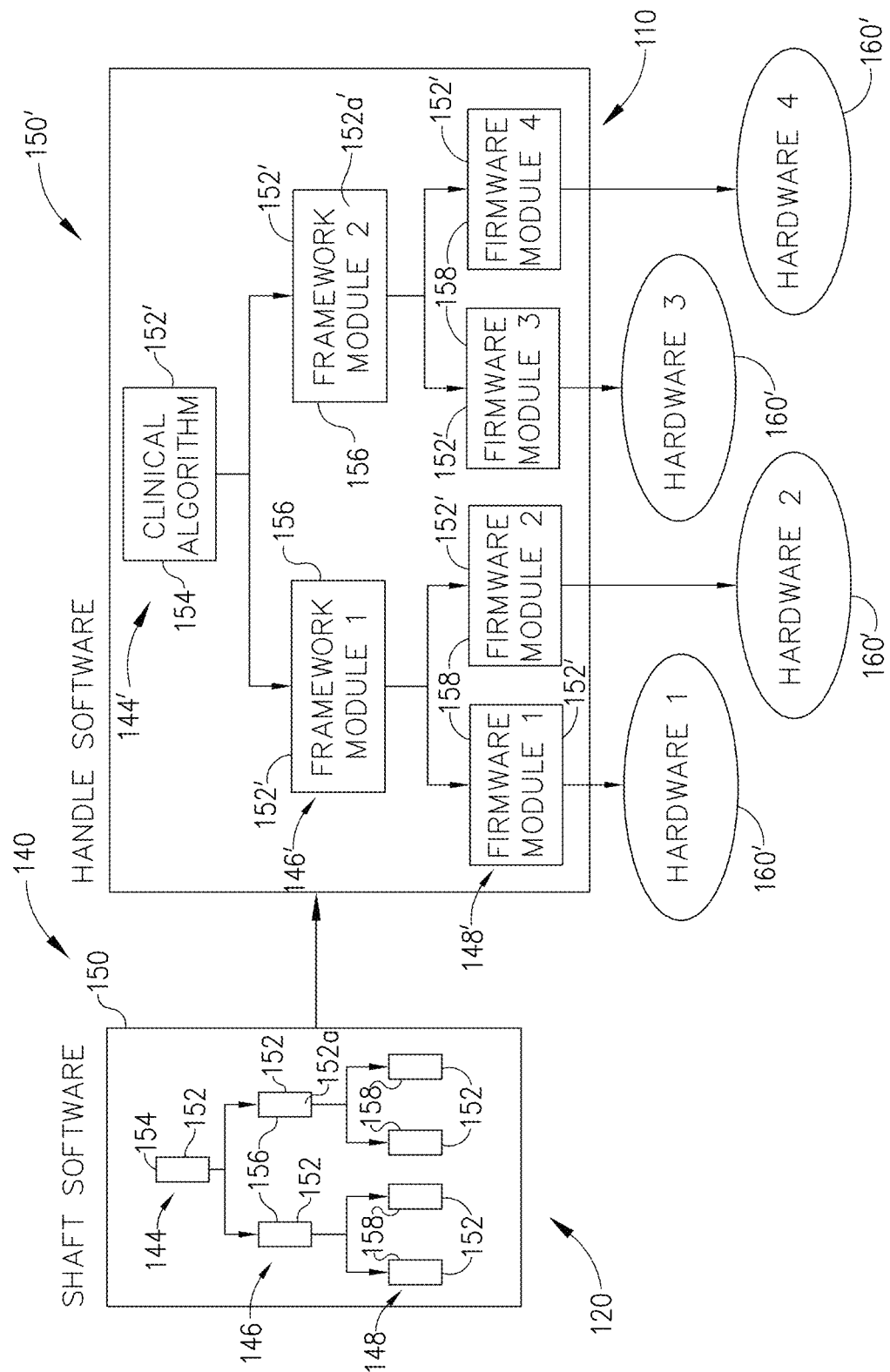
FIG. 25 is a schematic depicting the control systems of a modular surgical system according to various embodiments of the present disclosure.

Referring now to FIG. 25, the assembled surgical system can include a first control system 150' and a second control system 150. The control systems 150', 150 can be in signal communication, for example. In various instances, the second modular component 120 can comprise the control system 150, for example, which can include a plurality of control modules 152. The control modules 152 can affect a surgical function with and/or by an element or subsystem of the surgical instrument 100, for example. The control modules 152 can affect a surgical function based on a pre-programmed routine, operator input, and/or system feedback, for example. In various instances, the first modular component 110 can also comprise a control system 150', for example, which can include a plurality of control modules 152'. The control r, system 150' and/or one of the control modules 152' of the first modular component 110 may be different than the control system 150 and/or one of the control modules 152 of the second modular component 120. Though the control systems 150 and 150' can be different, the control systems 150 and 150' can be configured to control corresponding functions. For example, the control module 152(*a*) and the control module 152(*a*)' can both issue commands to firmware modules 158 to implement a firing stroke, for example. In various instances, one of the control systems 150, 150' and/or a control module 152, 152' thereof may include updated software and/or firmware and/or can have a more-recent effective date, as described in greater detail herein.

A control module 152, 152' can comprise software, firmware, a program, a module, and/or a routine, for example, and/or can include multiple software, firmware, programs, control modules, and/or routines, for example. In various circumstances, the control systems 150, 150' can include multiple tiers and/or levels of command. For example, the control system 150 can include a first tier 144 of control modules 152, a second tier 146 of control modules 152, and/or a third tier 148 of control modules 152. Control modules 152 of the first tier 144 can be configured to issue commands to the control modules 152 of the second tier 146, for example, and the control modules 152 of the second tier 146 can be configured to issue commands to the control modules 152 of the third tier 148. In various instances, the control systems 150, 150' can include less than three tiers and/or more than three tiers, for example.

Referring still to FIG. 25, the control module(s) 152 in the first tier 144 can comprise high-level software, or a clinical algorithm 154. The clinical algorithm 154 can control the high-level functions of the surgical instrument 100, for example. In certain instances, the control module(s) 152 in the second tier 146 can comprise intermediate software, or framework module(s) 156, which can control the intermediate-level functions of the surgical instrument 100, for example. In certain instances, the clinical algorithm 154 of the first tier 144 can issue abstract commands to the framework module(s) 156 of the second tier 146 to control the surgical instrument 100. Furthermore, the control modules 152 in the third tier 148 can comprise firmware modules 158, for example, which can be specific to a particular hardware component 160, or components, of the surgical instrument 100. For example, the firmware modules 158 can correspond to a particular cutting element, firing bar, trigger, sensor, and/or motor of the surgical instrument 100, and/or can correspond to a particular subsystem of the surgical instrument 100, for example. In various instances, a framework module 156 can issue commands to a firmware module 158 to implement a surgical function with the corresponding hardware component 160. Accordingly, the various control modules 152 of the surgical system 100 can communicate and/or cooperate during a surgical procedure.

Referring still to FIG. 25, the control system 150 of the second component 120 can correspond to the control system 150' of the first component 110, and the various control modules 152 of the second component 120 can correspond to the control modules 152' of the first component 110. Stated differently, each control module 152 can include a parallel, or corresponding control module 152', and both control modules 152 and 152' can be configured to perform identical, similar and/or related functions and/or to provide identical, similar and/or related commands. Referring still to FIG. 25, the control module 152*a* can correspond to the control module 152*a*'. For example, the control modules 152*a* and 152*a*' can both control the firing stroke of a cutting element; however, control module 152*a* can be configured to control a first cutting element design or model number and control module 152*a*' can be configured to control a different cutting element design or model number, for example. In other instances, the control module 152*a*' can comprise a software program and control module 152*a* can comprise an updated or revised version of the software program, for example.

In various instances, the first component 110 of the surgical instrument 100 can include a clinical algorithm 154' that is different than the clinical algorithm 154 of the second component 120. Additionally and/or alternatively, the first component 110 can include a framework module 156' that is different than a corresponding framework module 156 of the second component 120, and/or the first component 110 can include a firmware module 158' that is different than a corresponding firmware module 158 of the second component 120.

In various instances, corresponding control modules 152, 152' can comprise different effective dates. A person having ordinary skill in the art will appreciate that the effective date of a control module 152, 152' can correspond to a date that the control module 152, 152' was designed, created, programmed, and/or updated, for example. The effective date of a control module can be recorded or stored in the program code of the control module, for example. In certain instances, a control module of the surgical instrument 100 can be outdated. Furthermore, an out-of-date, or less-recently updated, control module may be incompatible with, disjointed from, and/or disconnected from an up-to-date and/or more-recently updated, control module. Accordingly, in certain instances, it may be desirable to update out-of-date control modules to ensure proper and effective operation of the surgical instrument 100.

In various instances, a modular component of the surgical system can include a predetermined default, or master, control system. In such instances, if the control systems of the assembled modular components are different, the default control system can update, overwrite, revise, and/or replace the non-default control systems. In other words, if corresponding control modules are different, incompatible, or inconsistent, for example, the non-default control module can be updated and the default control module can be preserved. For example, if the handle 110 comprises the control system 150', which is the non-default control system, and the shaft 120 comprises the control system 150, which is the master control system, the control system 150' of the handle 110 can be updated based on the control system 150 of the shaft 120.

It may be desirable to program a shaft component 120 of the surgical instrument to include the default control system in circumstances where shaft components are more frequently updated and/or modified than handle components. For example, if new generations and/or iterations of shaft components 120 are introduced more frequently than new generations and/or iterations of handle components 110, it may be advantageous to include a default, or master, control system in the shaft component 120 of the modular surgical instrument 100. Various circumstances described throughout the present disclosure relate to updating control modules of a handle component based on control modules of the shaft component; however, a person of skill in the art will readily appreciate that, in other contemplated circumstances, the control modules of the shaft component and/or a different modular component may be updated instead of or in addition to the control modules of the handle component.

Figure 26:
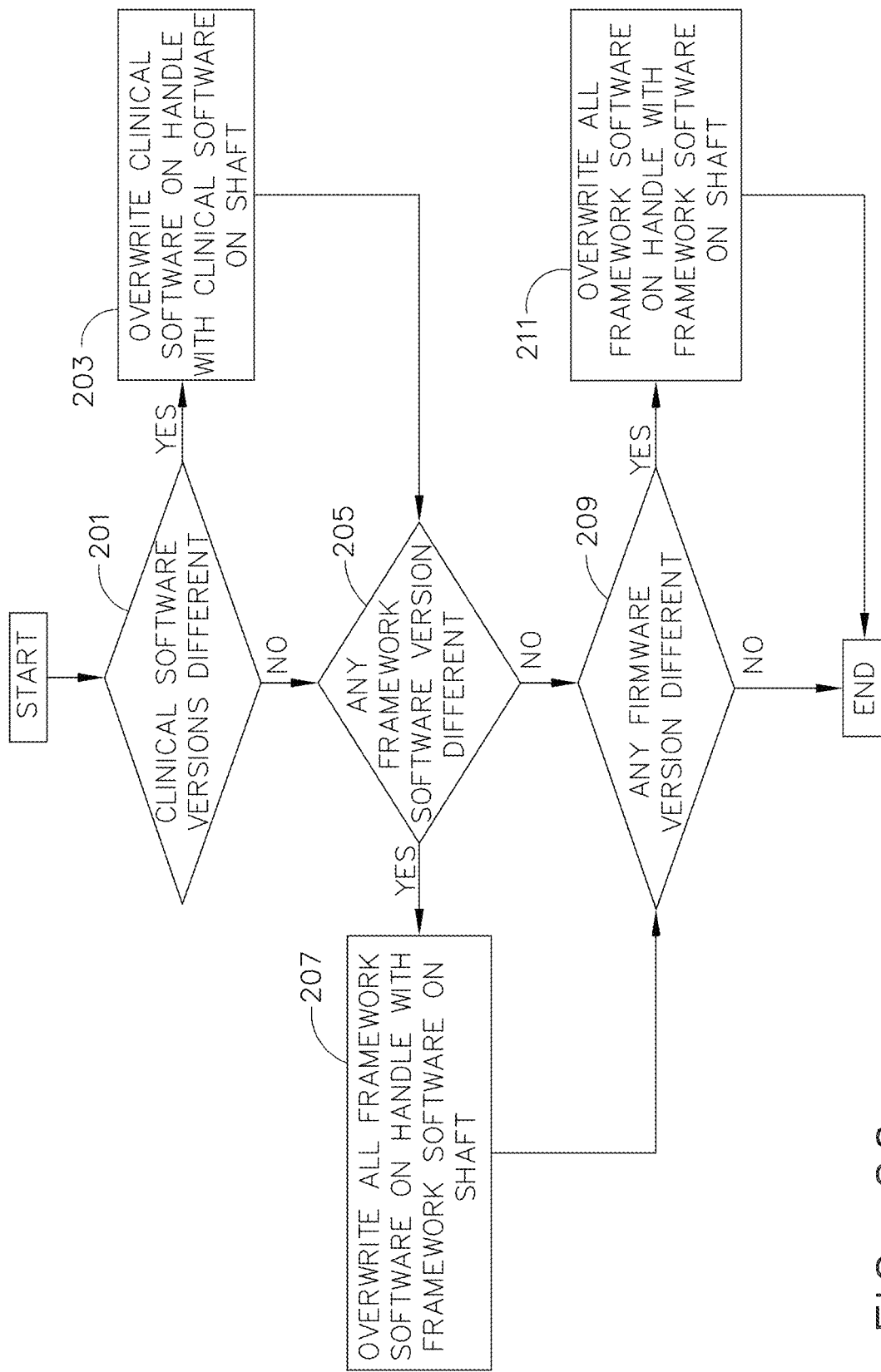
FIG. 26 is a flowchart depicting a method for updating a component of a modular surgical system according to various embodiments of the present disclosure.

In various instances, the surgical instrument 100 (FIGS. 23 and 24) can compare the control module(s) 152' at each tier or level in the control system 150' to the control module(s) 152 at each corresponding tier or level in the control system 150. If the control modules 152 and 152' in corresponding tiers are different, a control system 150, 150' can update the non-default control module(s), for example. Referring to FIG. 26, at step 201, the control system 150 and/or the control system 150' can compare the control module(s) 152' of the first tier 144' of the first component 110 to the control module(s) 152 of the first tier 144 of the second component 120. Where the first tiers 144, 144' comprise high-level clinical algorithms 154, 154', respectively, the control system 150 and/or the control system 150' can compare the clinical algorithms 154 and 154', for example. Furthermore, at step 203, if the control modules 152, 152' in the first tiers 144, 144' are different, the control system 150 and/or the control system 150' can update the module(s) 152' of the first tier 144' with the default module(s) 152 of the first tier 144, for example. In various instances, the control system 150 can compare and/or update a control system and/or control modules and, in other circumstances, the control system 150' can compare and update a control system and/or control modules, for example. In various instances, one of the control systems 150, 150' can be configured to compare and/or update a control system and/or control modules and, in other instances, both control systems 150, 150' can be configured to compare and/or update a control system and/or control modules.

At step 205, the control system 150 and/or the control system 150' can compare the control modules 152' of the second tier 146' of the first component 110 to the control modules 152 of the second tier 146 of the second component 120. For example, where the second tiers 146, 146' comprise mid-level framework algorithms 156, 156', the control systems 150, 150' can compare the framework algorithms 156 and 156', for example. At step 207, if the modules 152, 152' in the second tiers 146, 146' are different, the control systems 150, 150' can update the control modules 152' of the second tier 146' with the default control modules 152 of the second tier 146. In various instances, though one or more of the control modules 152' in the second tier 146' can be the same as a corresponding module 152 in the second tier 146, all control modules 152' of the second tier 146' can be updated if any corresponding second tier modules 152, 152' are different. In other instances, as described in greater detail herein, only the control module(s) 152' that is/are different than the corresponding module(s) 152 may be updated.

At step 209, the control systems 150 and/or the control system 150' can compare the control modules 152' of the third tier 148' of the first component 110 to the control modules 152 of the third tier 148 of the second component 120. For example, where the third tiers 148, 148' comprise firmware modules 158, 158', the control system 150 and/or the control system 150' can compare the firmware modules 158 and 158', for example. If the modules 152, 152' in the third tiers 148, 148' are different, the control system 150 and/or the control system 150' can update the control modules 152' of the third tier 148' with the default control modules 152 of the third tier 148 at step 211. In various instances, though one or more of the control modules 152' in the third tier 148' can be the same as a corresponding control module 152 in the third tier 148, all modules 152' of the third tier 148' can be updated if any corresponding third tier modules 152, 152' are different. In other instances, only the control module(s) 152' that is/are different than the corresponding control module(s) 152 may be updated, as described in greater detail herein. Referring still to FIG. 26, the first tier control modules 154, 154' can be updated prior to the second tier control modules 156, 156', for example, and the second tier control modules 156, 156' can be updated prior to the third tier control modules 158, 158', for example. In other instances, as described in greater detail herein, the third tier control modules 158, 158' can be updated prior to the second tier control modules 156, 156', for example, and the second tier control modules 156, 156' can be updated before the first tier control modules 154, 154', for example.

As described above, the control system 150 and/or the control system 150' may compare the control system 150, 150' and/or the control modules 152, 152' thereof prior to updating, replacing and/or overwriting an outdated control module 152, 152' and/or control systems 150, 150'. A reader will appreciate that this step can reduce the instrument startup time when software updates and/or upgrades are unnecessary or unmerited. Alternatively, the comparison steps 201, 205, and 209 could be eliminated, and the control systems 150, 150' may automatically update, replace, revise and/or overwrite the control module(s) 152' of the first modular component 110 and/or specific, predetermined control module(s) 152 of the first modular component 110, for example.

In various instances, the control modules 152, 152' can be compared and updated on a tier-by-tier basis and, in other instances, the control systems 150, 150' can be compared and updated on a system-by-system basis. In still other instances, the control modules 152, 152' can be updated on a module-by-module basis. For example, referring now to FIG. 27, at step 221, a third tier module 158' of the first control system 150' can be compared to a corresponding third tier module 158 of the second control system 150. In various instances, the effective date of the third tier module 158' can be compared to the effective date of the corresponding third tier module 158. Moreover, the control system 150 and/or the control system 150' can determine if the effective date of the third tier module 158' postdates the effective date of the third tier module 158. If the third tier module 158' is newer than the third tier module 158, for example, the third tier module 158' can be preserved at step 225. Conversely, if the third tier module 158' is not newer than the third tier module 158, i.e., the third tier module 158 predates the corresponding third tier module 158 or the third tier module 158 and the corresponding third tier module 158' have the same effective date, the third tier module 158' can be updated, replaced, revised, and/or overwritten by the corresponding third tier module 158, for example. Furthermore, in various instances, steps 221 and either 223 or 225 can be repeated for each module 158, 158' in the third tier of the control systems 150, 150'. Accordingly, the modules 158' in the third tier 148' may be updated on a module-bymodule basis, and in various instances, only outdated modules 158' can be updated and/or overwritten, for example.

Figure 27:
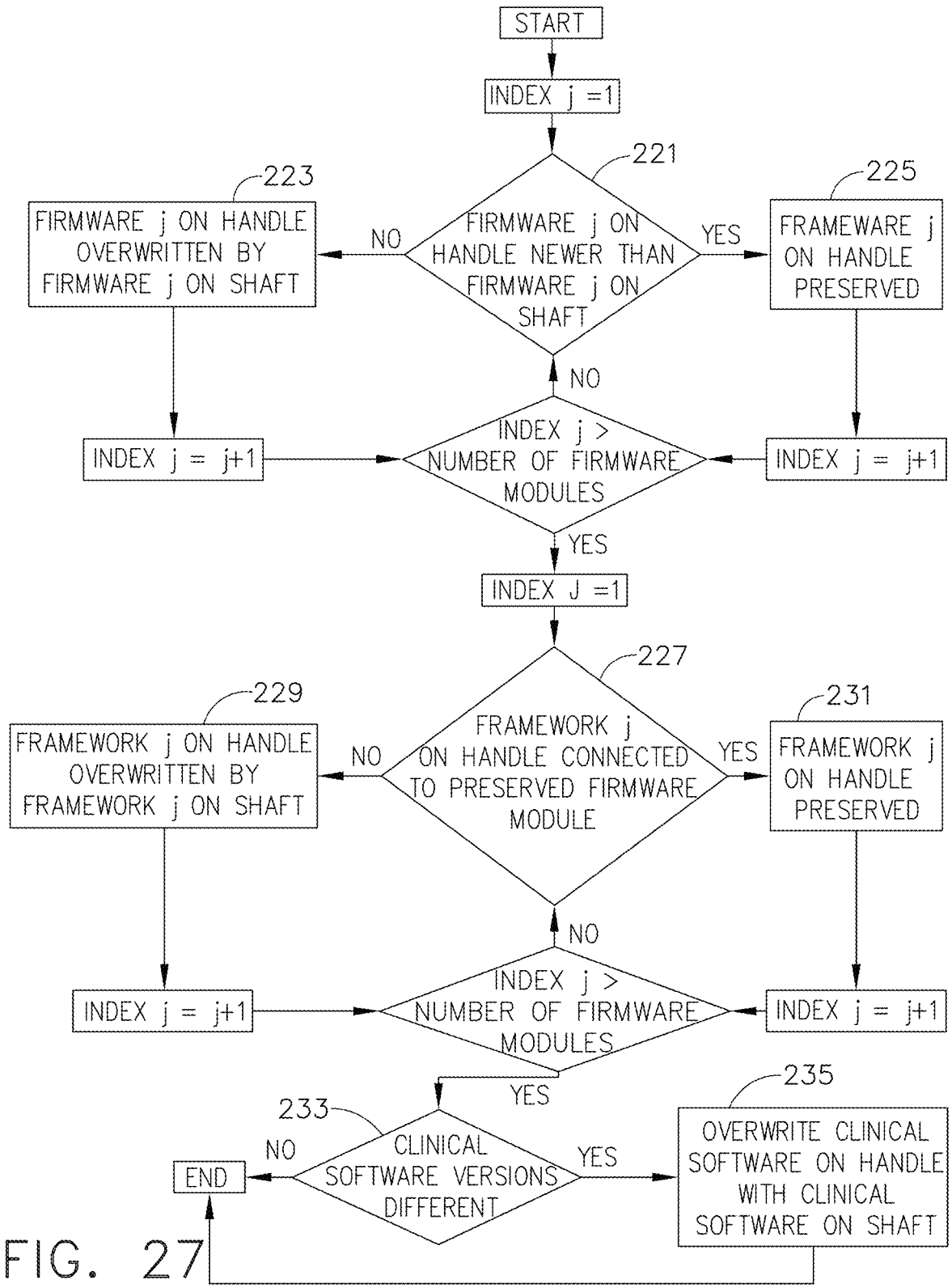
FIG. 27 is a flowchart depicting a method for updating a component of a modular surgical system according to various embodiments of the present disclosure.

Referring still to FIG. 27, after all third tier modules 158, 158' have been compared and possibly updated, the control systems 150, 150' can progress to step 227. At step 227, the control system 150 and/or the control system 150' can confirm that a third tier module 158' of the first control system 150' is connected and/or in proper communication with a second tier module 156' of the control system 150'. For example, in circumstances where the third tier module 158' was updated at step 223, the second tier module 156' may be disconnected from the updated third tier module 158'. If the third tier module 158' is disconnected from the second tier module 156', for example, the second tier module 156' can be updated, replaced, revised, and/or overwritten at step 229. The second tier module 156' can be replaced by the corresponding second tier module 156 of the second control system 150, for example. Conversely, if the third tier module 158' is properly connected and/or in communication with the second tier module 156', the second tier module 156' can be preserved. Furthermore, in various instances, steps 227 and either 229 or 231 can be repeated for each module 158, 158' in the third tier of the control systems 150, 150'. Accordingly, the modules 156' in the second tier 146' may be updated on a module-by-module basis, and in various instances, only disconnected modules 156' can be updated or overwritten, for example.

After updating any outdated third tier modules 158' (steps 221 and 223) and ensuring all updated third tier modules 158', if any, are connected to the appropriate second tier module 156' on the first modular component 110 (steps 227, 229, and 231), the control systems 150, 150' can progress to step 233, wherein the first tier module 154' of the first control system 150' can be compared to a corresponding first tier module 154 of the second control system 150. If the first tier modules 154, 154' are the same, the updating and/or revising process can be complete. Conversely, if the first tier modules 154, 154' are different, the first tier module 154' of the first control system 150' can be updated, replaced, revised, and/or overwritten by the first tier module 154 of the second control system 150.

As described herein, the software and/or firmware modules of the modular components 110, 120 can be updated, revised, and/or replaced on a module-by-module, tier-by-tier, and/or system-by-system basis. In certain instances, the updating and/or revision process can be automatic when the modular components are attached and/or operably coupled. In other circumstances, an operator of the surgical instrument 100 can initiate or trigger the updating and/or revision process described herein.

Figure 23:
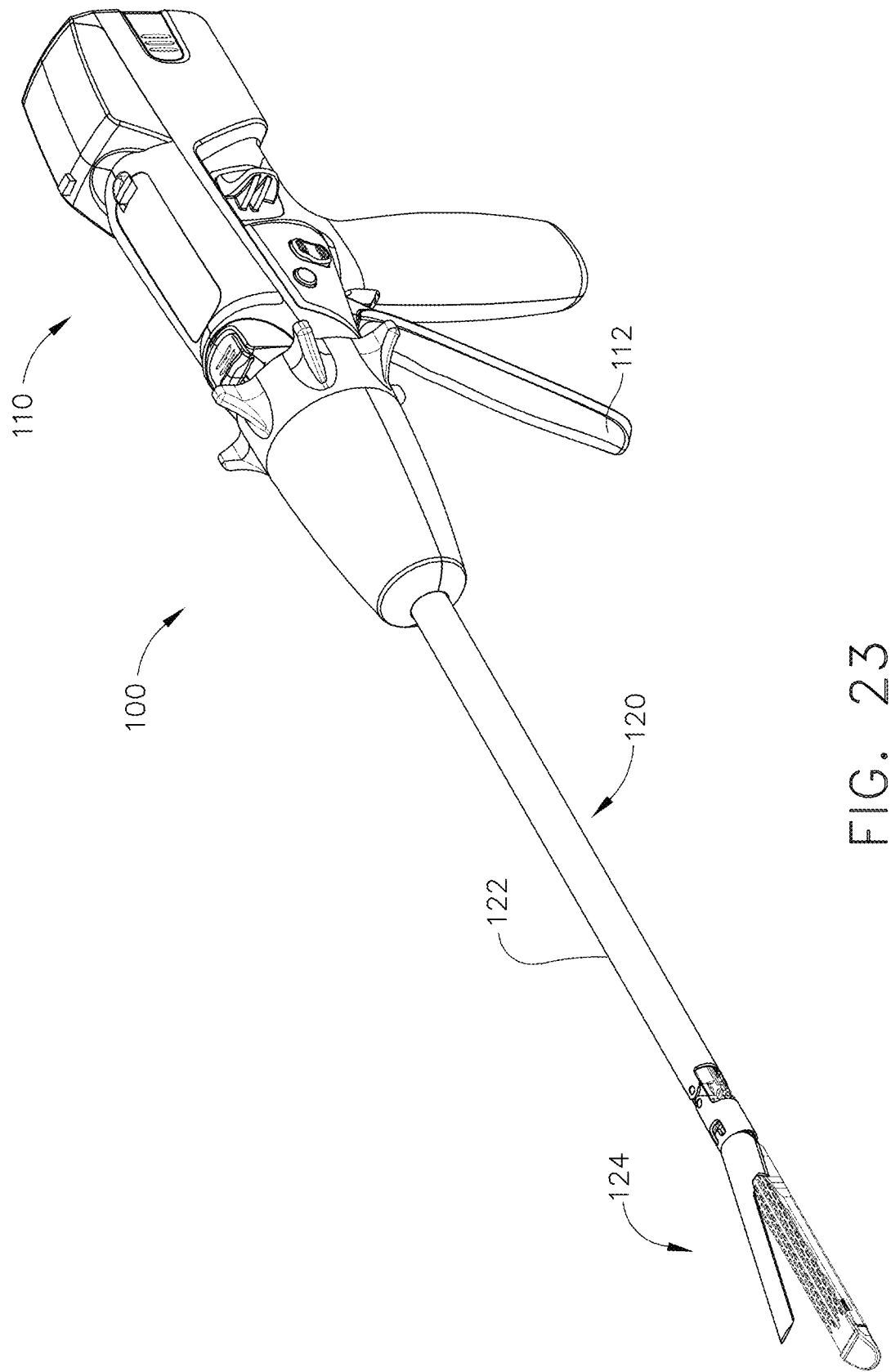
FIG. 23 is a perspective view of a modular surgical instrument according to various embodiments of the present disclosure.
Figure 24:
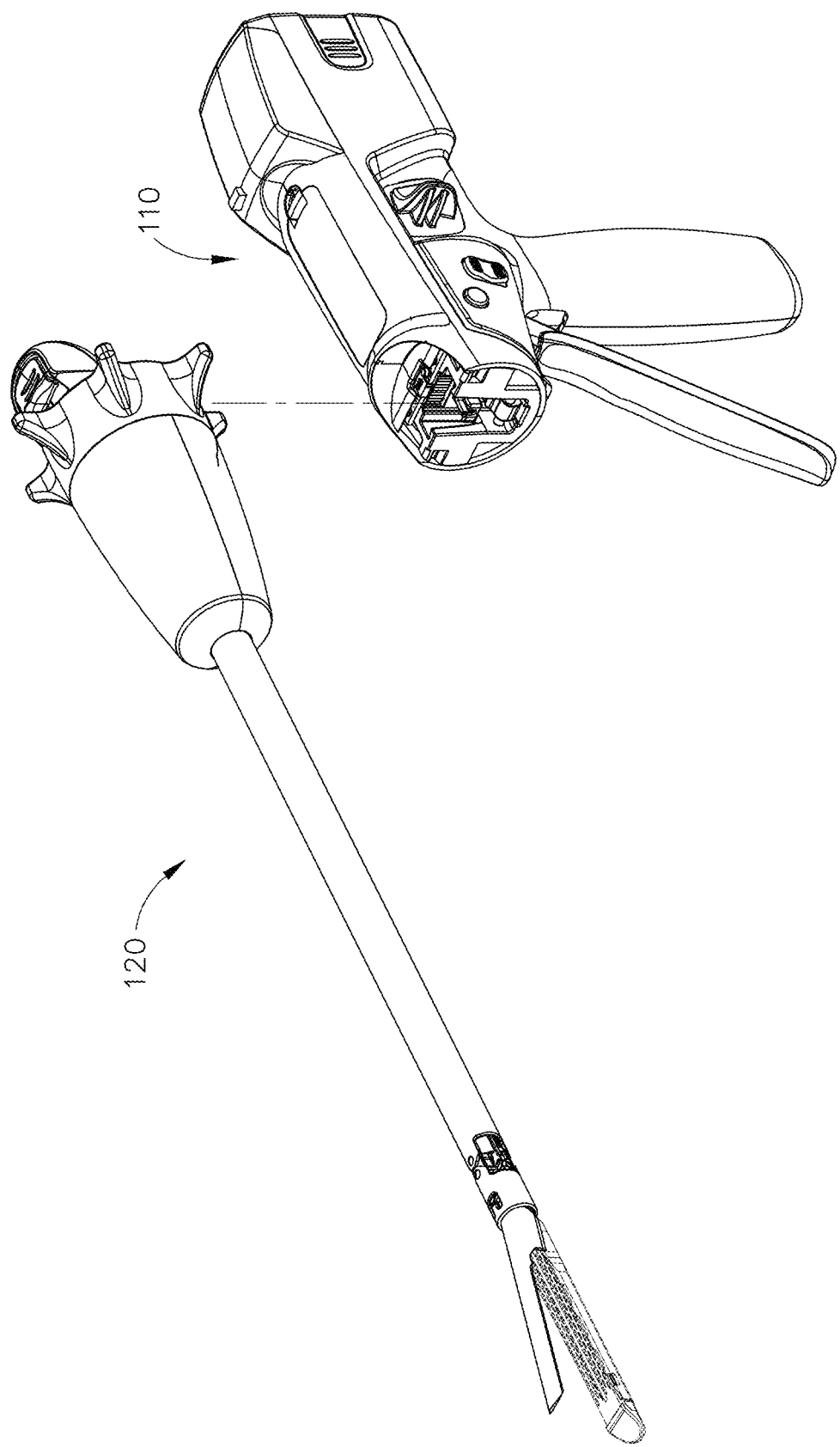
FIG. 24 is an exploded, perspective view of the modular surgical instrument of FIG. 23.

In various instances, a modular surgical instrument, such as the modular surgical instrument 100 (FIGS. 23 and 24), for example, can include a microcontroller in signal communication with an engagement sensor and a display. In various instances, the engagement sensor can detect the relative positioning of modular components of the surgical system. Referring again to FIGS. 23 and 24, where the first modular component 110 comprises a handle and the second modular component 120 comprises a shaft, for example, an engagement sensor can detect whether the shaft 120 is engaged with and/or operably coupled to the handle 110. In various instances, the shaft 120 can be moveable between engagement with the handle 110 (FIG. 23) and disengagement from the handle 110 (FIG. 24).

Figure 28A:
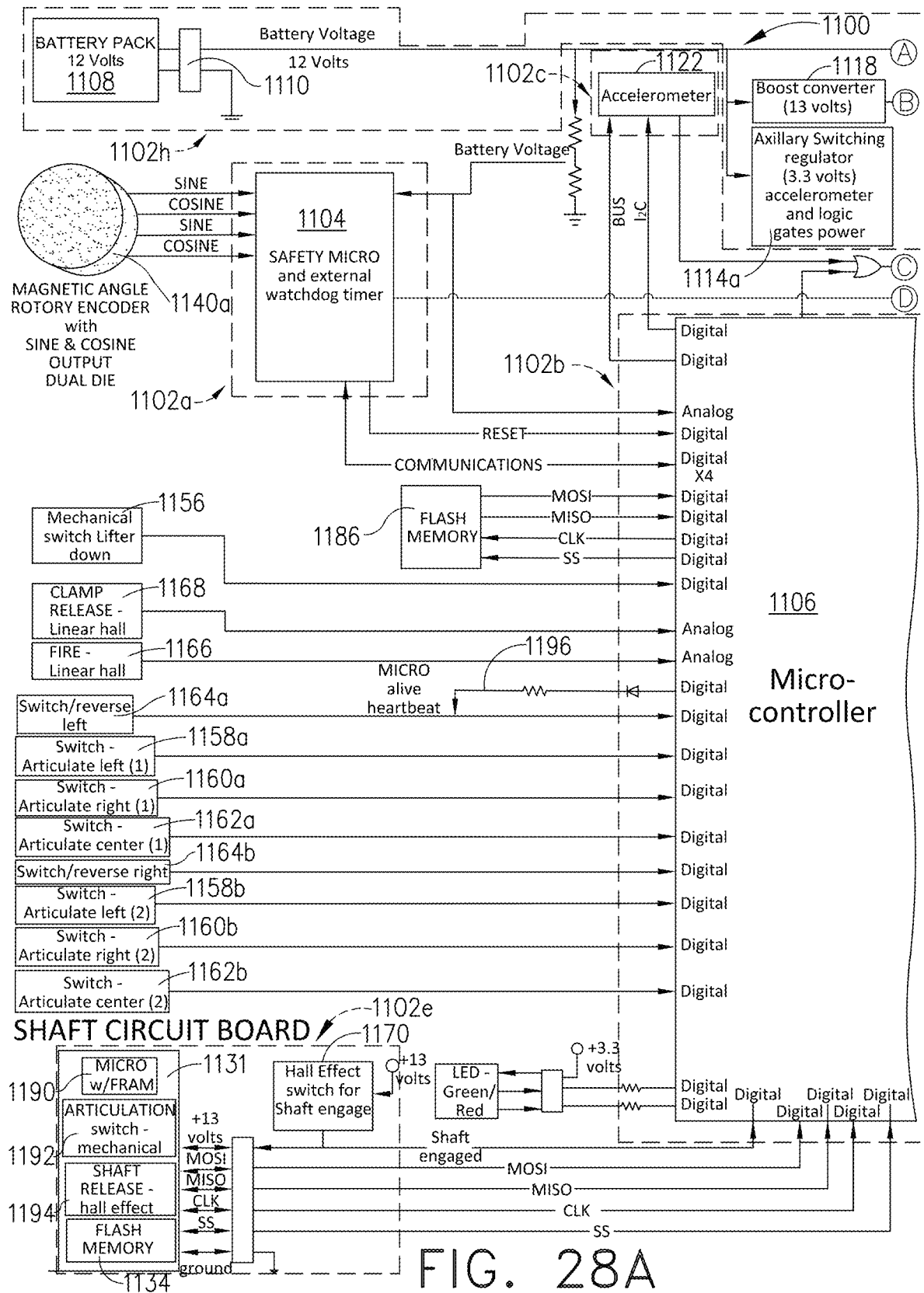
FIGS. 28(A) and 28(B) are schematics depicting a control circuit according to various embodiments of the present disclosure.
Figure 28B:
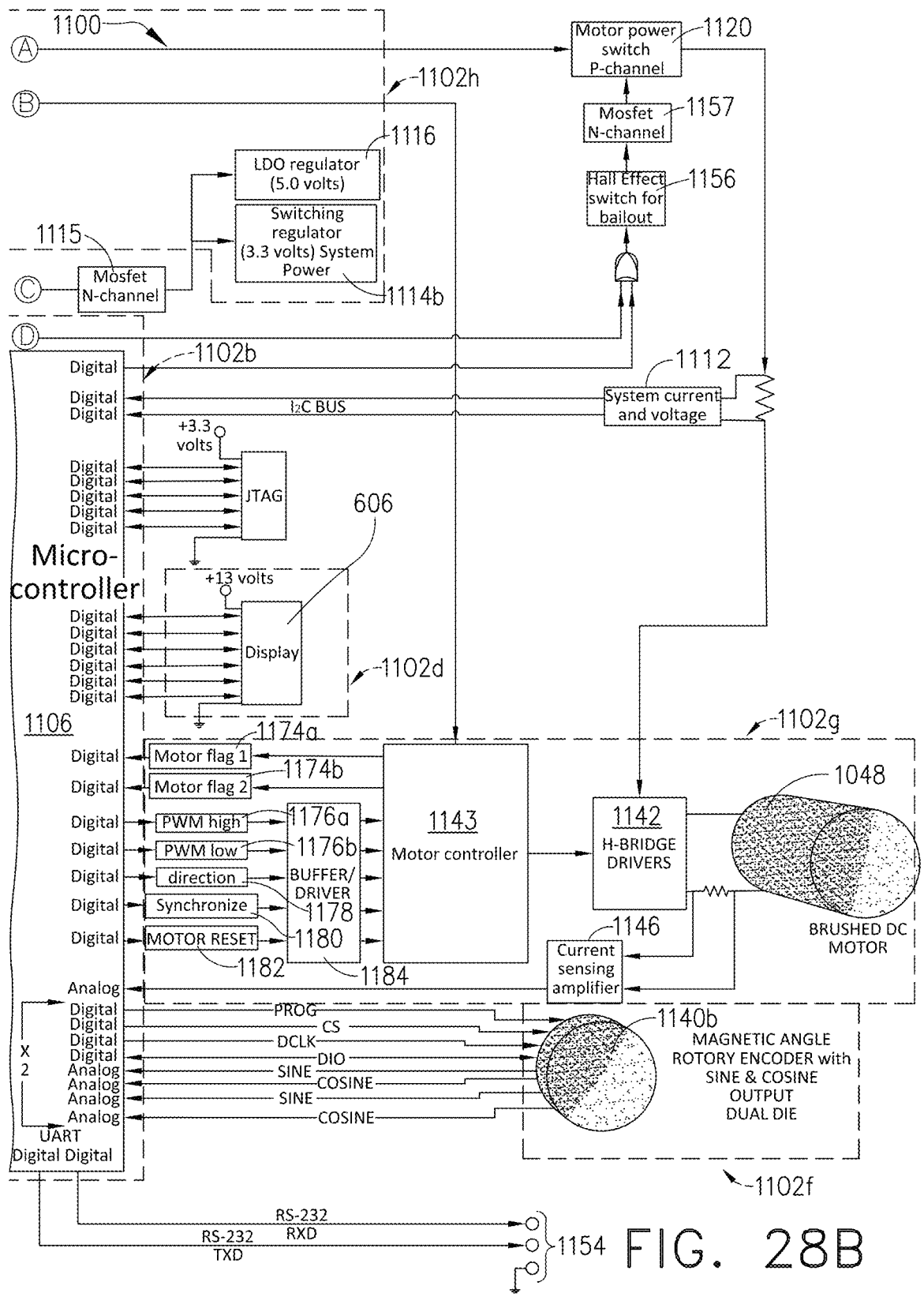

Referring primarily to FIGS. 28(A) and 28(B), an engagement sensor, such as the engagement sensor 1170, for example, can be in signal communication with a microcontroller, such as the microcontroller 1106, for example, of a surgical system. In various instances, the engagement sensor 1170 can detect whether the modular components 110, 120 are engaged or disengaged, for example, and can communicate the engagement or lack thereof to the microcontroller 1106, for example. When the engagement sensor 1170 indicates that the shaft 120 is engaged with the handle 110, for example, the microcontroller 1106 can permit a surgical function by the modular surgical instrument 100 (FIG. 23). If the modular components 110, 120 are operably coupled, for example, an actuation of the firing trigger 112 (FIG. 23) on the handle 110 can affect, or at least attempt to affect, a firing motion in the shaft 120, for example. Conversely, if the engagement sensor 1170 indicates that the shaft 120 is disengaged from the handle 110, the microcontroller 1106 can prevent a surgical function. For example, if the modular components 110, 120 are disconnected, an actuation of the firing trigger may not affect, or not attempt to affect, a firing motion in the shaft 120.

In various instances, the modular surgical instrument 100 can include a display, such as the display 606 (FIG. 28(B)), for example. The display 606 can be integrated into one of the modular components 110, 120 of the surgical instrument 100 and/or can be external to the modular components 110, 120 and in signal communication with the microcontroller 1106 of the surgical instrument 100. In various instances, the microcontroller 1106 can communicate the information detected by the engagement sensor 1170 to the display 606. For example, the display 606 can depict engagement and/or non-engagement of the modular components 110, 120. Moreover, in various instances, the display 606 can provide instructions and/or guidance regarding how to (a) properly attach, couple, and/or engage the disengaged components 110, 120 of the surgical instrument 100, and/or how to (b) properly un-attach, decouple, and/or disengage the engaged components 110, 120 of the surgical instrument 100. Referring again to FIG. 28(A), in various instances, the engagement sensor 1170 can comprise a Hall Effect switch, and in other instances, the engagement sensor can comprise a different and/or additional sensor and/or switch, for example.

In certain circumstances, the engagement sensor 1170 can detect the degree of engagement between modular components of a surgical instrument. In instances where the first component comprises the handle 110, for example, and the second component comprises the shaft 120, for example, the handle 110 and the shaft 120 can move between a disengaged position, a partially-engaged position, and an engaged position. The partially-engaged position can be intermediate the disengaged position and the engaged position, for example, and there may be multiple partially-engaged positions intermediate the engaged position and the disengaged position, for example. In various instances, the engagement sensor 1170 can include a plurality of sensors, which can detect the partially-engaged position(s) of the components 110, 120. For example, the engagement sensor 1170 can comprise a plurality of sensors and/or electrical contacts, for example, which can be staggered along an attachment portion of at least one of the modular components 110, 120, for example. In certain instances, the engagement sensor(s) 1170 can comprise a Hall Effect sensor, for example.

Figure 29A:
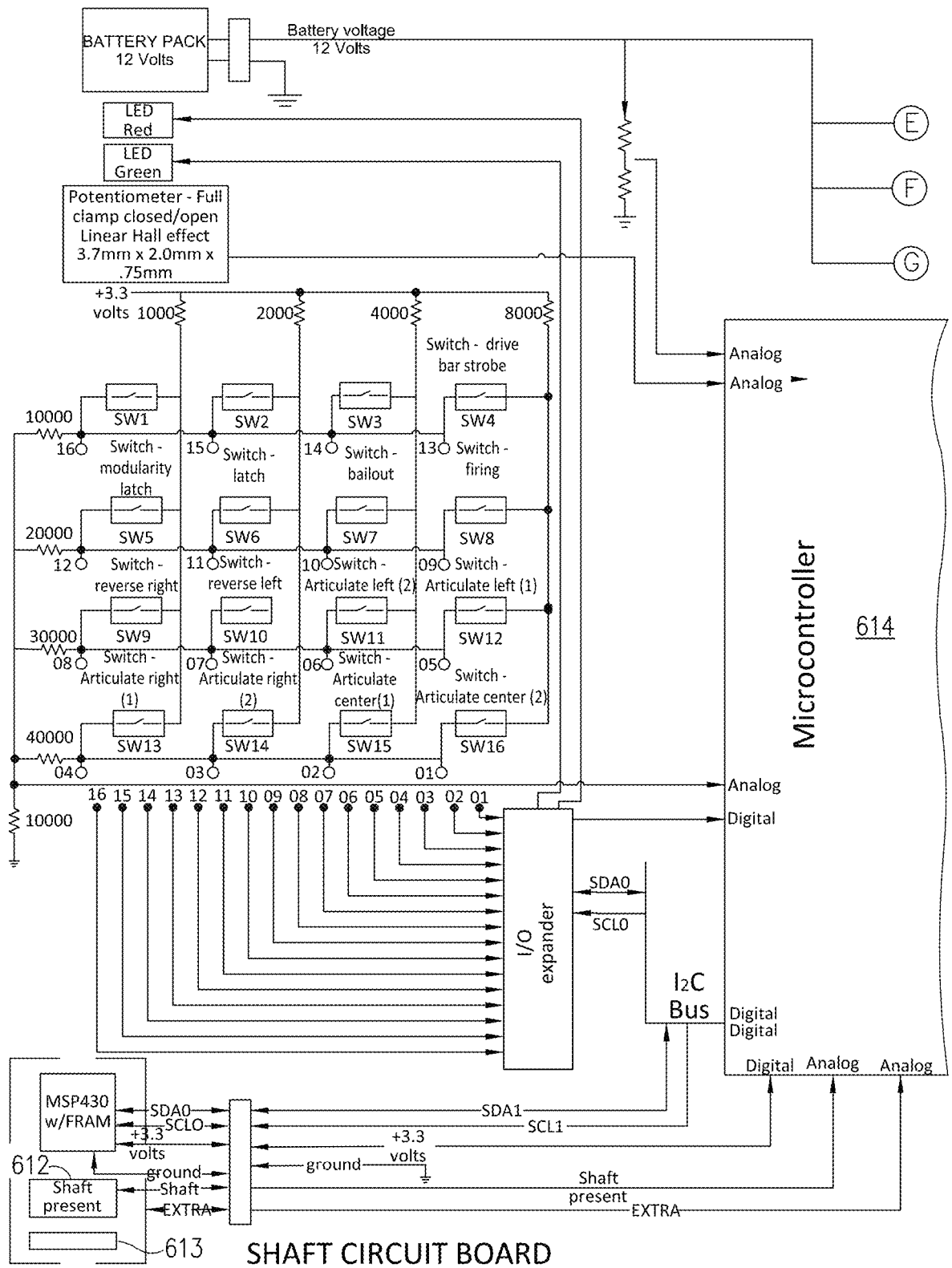
FIGS. 29(A) and 29(B) are schematics depicting a control circuit according to various embodiments of the present disclosure.
Figure 29B:
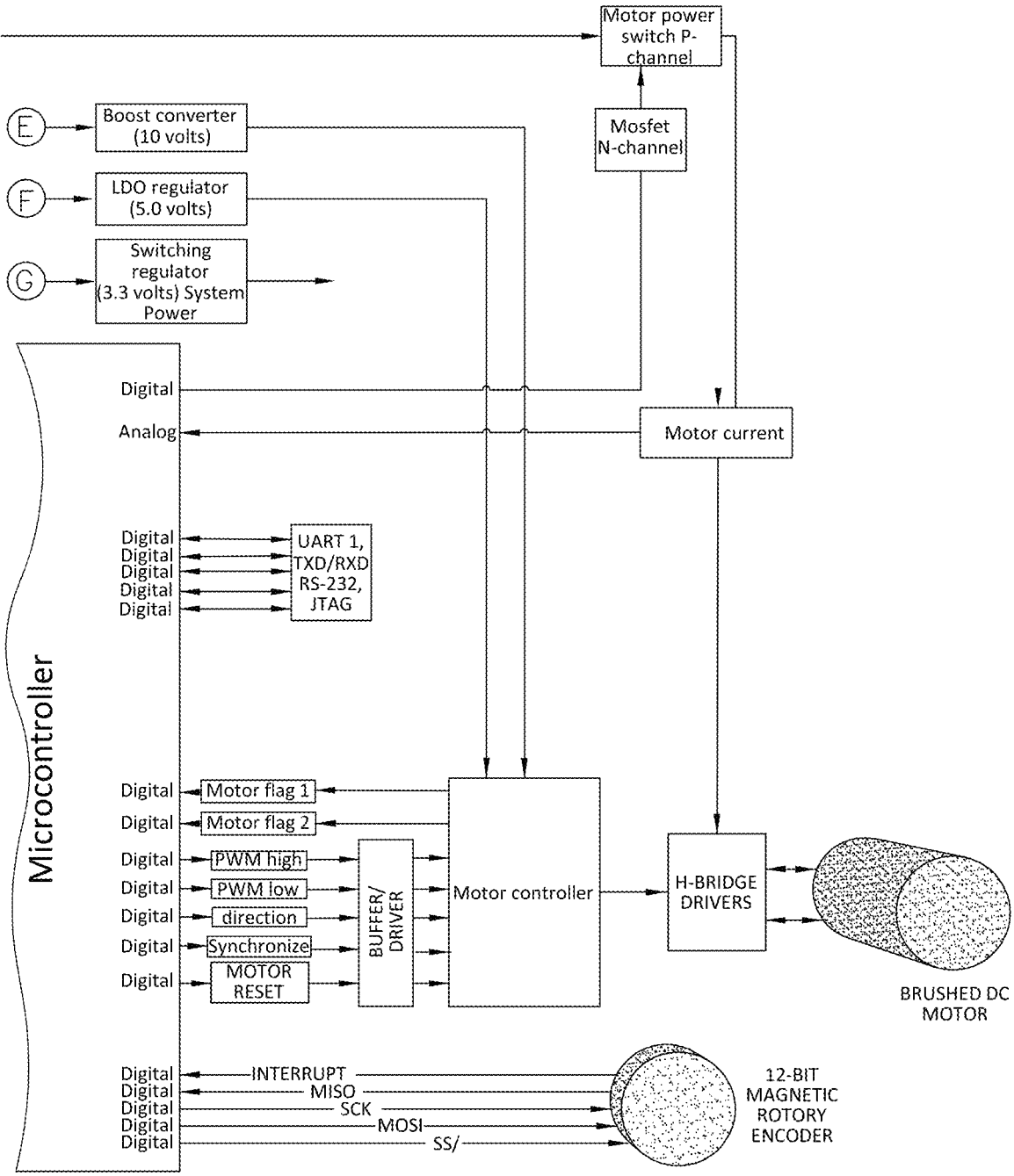

In certain instances, referring primarily to FIGS. 29(A) and 29(B), the surgical system 100 can include multiple sensors in signal communication with a microcontroller, such as the microcontroller 614, for example. The multiple sensors can include a first sensor 612 (FIG. 29(A)), which can detect the presence of the first component 120, and can communicate the presence of the first component 120 to the microcontroller 614, for example. In various instances, the first sensor 612 may not detect and/or communicate the degree of engagement between the first component 110 and the second component 120, for example. In various instances, a second sensor 613 (FIG. 29(A)) can also be in signal communication with the microcontroller 614. The second sensor 613 can detect the degree of engagement between the modular components 110, 120, for example.

Similar to the control system depicted in FIGS. 28(A) and 28(B), the microcontroller 614 can issue commands based on the feedback received from the sensors 612 and 613, and/or can be in signal communication with a display to display the feedback and/or otherwise communicate with an operator of the surgical system. For example, the microcontroller 614 can prevent a surgical function until the modular components 110, 120 are in the engaged position, and can prevent a surgical function when the modular components 110, 120 are partially-engaged, for example. Furthermore, the microcontroller 614 can communicate the information detected by the engagement sensor to a display. For example, the display can depict engagement, partial-engagement and/or non-engagement of the modular components 110, 120. Moreover, in various instances, the display can provide instructions and/or guidance regarding how to properly attach, couple, and/or engage disengaged and/or partially-engaged components 110, 120 of the surgical instrument, for example.

In various instances, a surgical instrument can include a microprocessor such as the microprocessor 604 (FIGS. 28(A) and 28(B)) or 614 (FIGS. 29(A) and 29(B)), for example, which can be in signal communication with a memory chip or memory unit. The microprocessor can communicate data and/or feedback detected and/or calculated by the various sensors, programs, and/or circuits of the surgical instrument to the memory chip, for example. In various instances, recorded data can relate to the time and/or duration of the surgical procedure, as well as the time and/or duration of various functions and/or portions of the surgical procedure, for example. Additionally or alternatively, recorded data can relate to conditions at the treatment site and/or conditions within the surgical instrument, for example. In certain instances, recordation of data can be automatic and, in other instances, the microprocessor may not record data unless and/or until instructed to record data. For example, it may be preferable to record data during a surgical procedure, maintain or store the recorded data in the memory chip, and/or transfer the recorded data to a secure site. In other circumstances, it may be preferable to record data during a surgical procedure and delete the recorded data thereafter, for example.

A surgical instrument and/or microcontroller thereof can comprise a data storage protocol. The data storage protocol can provide rules for recording, processing, storing, transferring, and/or deleting data, for example. In various instances, the data storage protocol can be preprogrammed and/or updated during the lifecycle of the surgical instrument. In various instances, the data storage protocol can mandate deletion of the recorded data after completion of a surgical function and/or surgical operation and, in other instances, the data storage protocol can mandate deletion of the recorded data after the elapse of a predefined period of time. For example, recorded data can be deleted, in accordance with the data storage protocol, one minute, one hour, one day, one week, one month or one year after the surgical function. The predefined period of time can be any suitable and appropriate period permitted by the circumstances.

Figure 31:
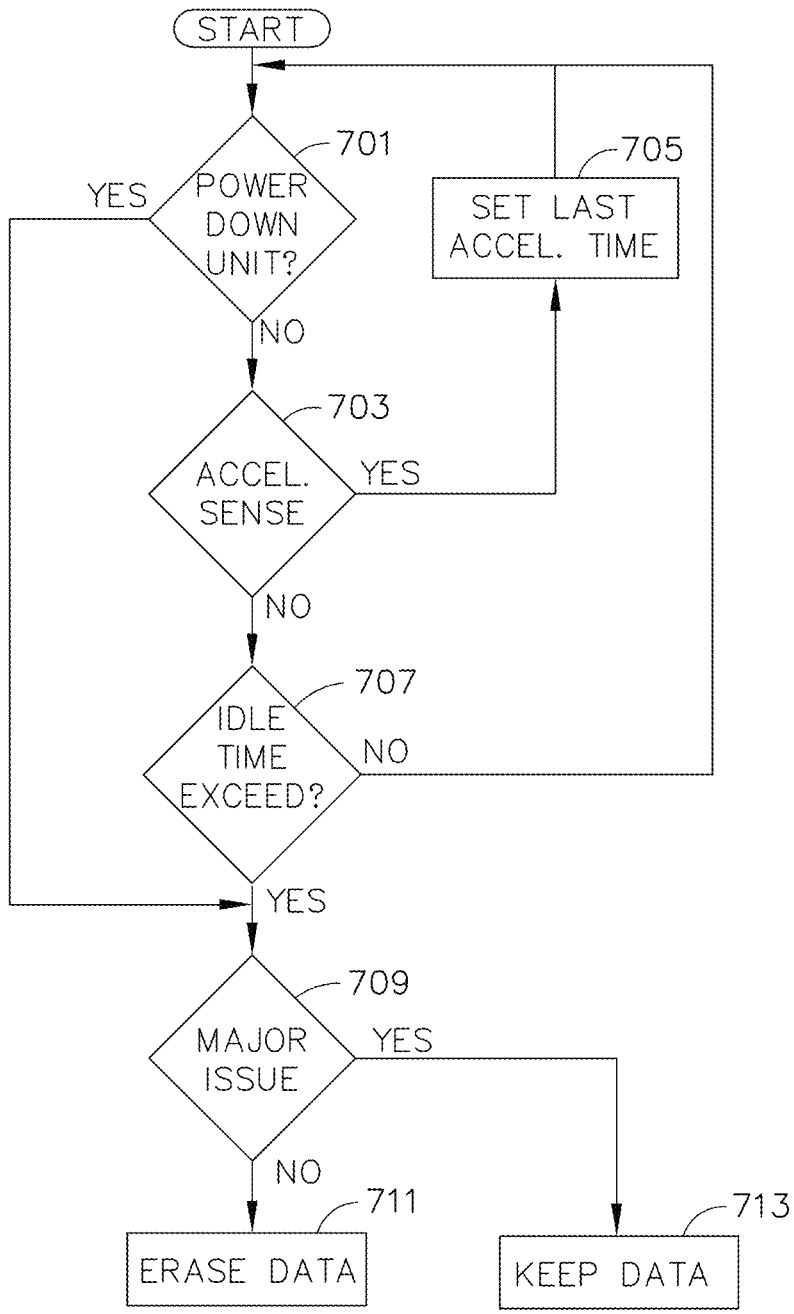
FIG. 31 is a flow chart depicting a method for processing data recorded by a surgical instrument according to various embodiments of the present disclosure.

In certain circumstances, the data storage protocol can mandate deletion of the recorded data after a predefined number of surgical functions, such as firing strokes, for example. In still other instances, the data storage protocol can mandate deletion of the recorded data when the surgical instrument is powered off. For example, referring to FIG. 31, if the surgical instrument is powered off, the microcontroller can proceed to step 709, wherein the microcontroller can determine if an error or major issue, such as an instrument, component or subsystem failure, for example, occurred during the surgical procedure. In various instances, if an error is detected, the microcontroller can proceed to step 713, wherein the data can be stored in the memory chip, for example. Moreover, in certain instances, if an error is not detected, the microcontroller can proceed to step 711, wherein the data can be deleted, for example. In other instances, the data storage protocol may not comprise the step 709, and the data storage protocol can continue without checking for a major error or failure, for example.

In still other instances, the data storage protocol can mandate deletion of the recorded data after a predefined period of inactivity or stillness of the surgical instrument. For example, if the surgical instrument is set down and/or put into storage, the data storage protocol can mandate deletion of the recorded data after the surgical instrument has been still or idle for a predefined period of time. The requisite period of stillness can be one minute, one hour, one day, one week, one month, or one year, for example. The predefined period of stillness can be any suitable and appropriate period permitted by the circumstances. In various instances, the surgical instrument can include an accelerometer, for example, which can detect movement and stillness of the surgical instrument. Referring again to FIG. 31, when the surgical instrument has not been powered off at step 701, the accelerometer can be set to detect movement of the surgical instrument. If movement is detected at step 703, prior to lapsing of the predefined idle period at step 707, the predefined idle time count can be restarted at step 705. Conversely, if movement is not detected by the accelerometer prior to lapsing of the predefined idle period at step 707, the microprocessor can proceed to step 709, for example. In other circumstances, the microprocessor can proceed directly to step 711 or 713, depending on the data storage protocol, without checking for an instrument error or failure, for example.

As described herein, the data storage protocol can include one of more default rules for deleting recorded data. In certain instances, however, it may be desirable to override the default rule or procedure. For example, for research and/or development purposes, it may be desirable to store recorded data for a longer period of time. Additionally or alternatively, it may be desirable to store recorded data for teaching and/or investigative purposes. Moreover, in various instances, the data storage protocol may not include an error-checking step and, in such instances, it may be desirable to override the data storage protocol and ensure storage of data when the operator detects or suspects an error and/or anomaly during a surgical procedure, for example. The recovered data can facilitate review of the procedure and/or a determination of the cause of the error, for example. In various instances, a key or input may be required to overcome or override the standard data storage protocol. In various instances, the key can be entered into the surgical instrument and/or a remote storage device, and can be entered by an operator and/or user of the surgical instrument, for example.

In various instances, a surgical system may prompt the user or instrument operator to select either data deletion or data storage for each surgical procedure or function. For example, the data storage protocol may mandate solicitation of instructions from the user, and may command subsequent action in accordance with the user's instructions. The surgical system may solicit instructions from the user upon the occurrence of a particular trigger event, such as powering down of the instrument, the elapse of a predefined period of time, or the completion of a particular surgical function, for example.

In certain instances, the surgical system can request input from a user when the surgical instrument is powered down, for example. Referring to FIG. 30, when a user initiates powering off of a surgical instrument at step 801, for example, the surgical system can request data storage instructions from the user. For example, at step 803, a display of the surgical system can ask, "KEEP DATA Y/N?" In various instances, the microcontroller of the surgical system can read the user input at step 805. If the user requests storage of the data, the microcontroller can proceed to step 809, wherein the data is stored in a memory unit or memory chip of the surgical system. If the user requests deletion of the data, the microcontroller can proceed to step 811, wherein the data is erased. In various instances, the user may not enter input. In such instances, the data storage protocol can mandate a particular process at step 813. For example, the data storage protocol may mandate "Process I", "Process II", or an alternative process, for example. In certain instances, "Process I" can command the deletion of data at step 813(*a*), and "Process II" can command the storage of data at step 813(*b*), for example. In various circumstances, the user can provide instructions to the surgical instrument before instruction have been solicited, for example. Additionally or alternatively, a display associated with the surgical system can request instruction from the user prior to initiating the surgical function and/or at different time(s) during instrument use, for example.

If data is stored in the memory of the surgical instrument, the data can be securely stored. For example, a code or key may be required to access the stored data. In certain instances, the access key can comprise an identification code. For example, the identification code can be specific to the operator, user, or owner of the surgical instrument. In such instances, only an authorized person can obtain a licensed identification code, and thus, only authorized personnel can access the stored data. Additionally or alternatively, the access key can be specific to the instrument and/or can be a manufacturer's code, for example. In certain instances, the access key can comprise a secure server, and data can be transferred and/or accessed by an approved Bluetooth and/or radio frequency (RF) transmission, for example. In still other circumstances, the access key can comprise a physical key, such as memory key and/or a data exchange port connector, which can be physically coupled to a data exchange port of the surgical instrument. In such instances, the access key can be preprogrammed to obtain access to the secure data, and to securely store and/or transfer the data, for example. In various circumstances, an access key can correspond to a specific surgical instrument, for example.

In various instances, data extraction from the memory device of a surgical instrument can be restricted by various security measures. In certain instances, the memory device of the surgical instrument can comprise a secure data connection or data exchange port. For example, the data exchange port can have a proprietary geometry or shape, and only authorized personnel can obtain a corresponding port key designed and structured to fit the proprietary geometry or shape, for example. In various instances, the data exchange port can comprise a mechanical lock, which can comprise a plug, a plurality of pins, and/or a plurality of springs, for example. In various instances, a physical key or extraction device can unlock the mechanical lock of the data exchange port. For example, the physical key can contact the plurality of pins, deform the plurality of springs, and/or bias the plug from a locked orientation to an unlocked orientation to unlock the data exchange port, for example.

In various instances, the data exchange port can comprise at least one connection pin, which can be biased and/or held in a first position. When a physical key is inserted into and/or engages the data exchange port, the physical key can bias the connection pin from the first position to a second position, for example. In various instances, the first position can comprise a retracted position, for example, and the second position can comprise an extended position, for example. Moreover, when the connection pin is moved to the second position, the connection pin can operably interface with a data connection port in the physical key, for example. Accordingly, the data exchange port of the memory device can move into signal communication with the data exchange port of the physical key via the connection pin, for example, such that data can be exchanged and/or transferred therebetween. In various instances, the physical key can comprise a modular component, for example, which can be configured to removably attach to the modular surgical instrument. In certain instances, the physical key can replace or mimic a modular component 110, 120 of a surgical instrument 100 (FIGS. 23 and 24). For example, the physical key can attach to an attachment portion of the handle 110 in lieu of a shaft attachment 120, for example, for the transfer of data from a memory device in the handle 120.

Additionally or alternatively, the key or extraction device can comprise a security token. In various instances, the data exchange port can be encrypted, for example, and/or the key can provide information or codes to the data exchange port to verify that the key is authorized and/or approved to extract data from the data exchange port. In certain circumstances, the key can comprise a specialized data reader, for example, and data can be transferred via an optical data transmission arrangement, for example.

Figures 32A, 32B, 32C:
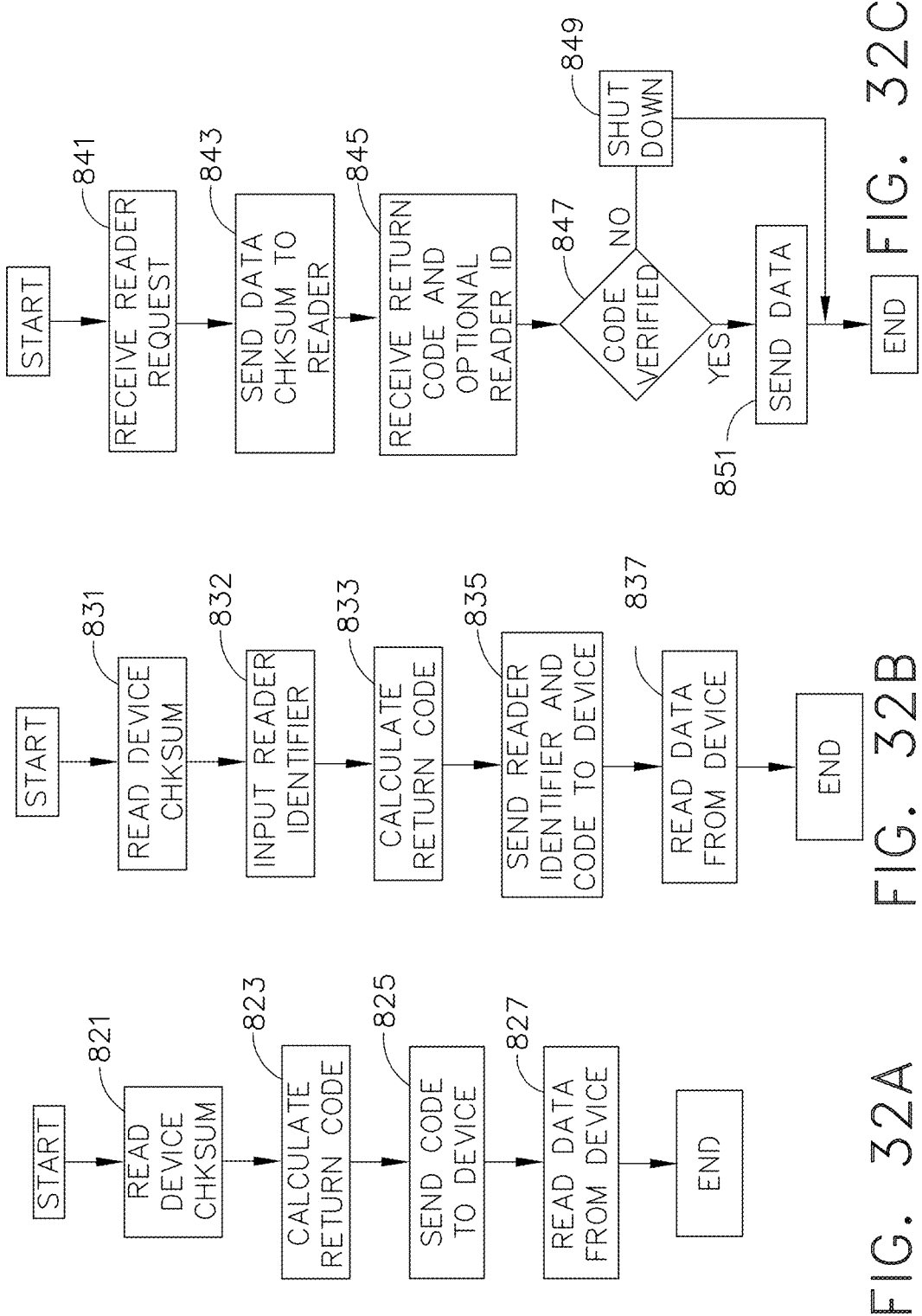
FIGS. 32(A)-32(C) are flow charts depicting various methods for processing data recorded by a surgical instrument according to various embodiments of the present disclosure.

Referring now to FIGS. 32(A)-32(C), before data access is granted to a proposed data reader, the data reader may need to be verified and/or confirmed by the surgical instrument. For example, the proposed data reader can request and read a checksum value of the surgical instrument at step 821. As depicted in the surgical instrument flowchart depicted in FIG. 32(C), the surgical instrument can first receive the proposed data reader request at step 841, and can then send the checksum value to the proposed data reader at step 843. Referring again to FIG. 32(A), at step 823, the proposed data reader can calculate or determine an appropriate return code based on the checksum value provided by the surgical instrument. The proposed data reader can have access to a code table, for example, and, if the proposed data reader is appropriately attempting to access the data, the appropriate return code can be available in the code table. In such instances, the proposed data reader can pull or calculate the return code at step 823 and can send the return code to the surgical instrument at step 825. Referring again to FIG. 32(C), upon receiving the return code from the proposed data reader at step 845, the surgical instrument can verify that the return code is correct at step 847. If the code is incorrect, the microprocessor of the surgical instrument can proceed to step 849, for example, and the surgical instrument can be shut down, or access to the stored data can be otherwise denied. However, if the code is correct, the microprocessor can proceed to step 851, for example, and the surgical instrument can provide data access to the proposed data reader. For example, the data can be securely transferred to the data reader at step 851. Thereafter, at step 827 (FIG. 32(A)), the proposed data reader can read the data from the surgical instrument, for example. In various instances, the transferred data can be encrypted, for example, and the data reader may need to decrypt the unintelligible data prior to reading it, for example.

Referring primarily to FIG. 32(B), an alternate data extraction security method can be similar to the method depicted in FIG. 32(A), for example, and can also require the consideration of a reader-specific code. Although the reader can read the checksum of the device at step 831 and the return code can be based on the checksum, in various circumstances, the proposed data reader can have a reader-specific code, and the appropriate return code from the code table can be based on the reader-specific code. For example, the proposed data reader can consider the reader-specific code at step 832, and can determine the appropriate return code at step 833 based on the reader-specific code and the code table, for example. The proposed data reader can provide the reader-specific code and the return code to the surgical instrument at step 835, for example. In such instances, referring again to FIG. 32(C), the microcontroller of the surgical instrument can verify the return code and reader-specific code, at step 845. Moreover, if these codes are correct, the surgical instrument can provide access to the proposed data reader. Thereafter, at step 827, the proposed data reader can read the data from the surgical instrument, for example. If one or both of the codes are incorrect, the surgical instrument can prevent the reader from reading the data. For example, the surgical instrument can shut down or otherwise restrict the transfer of data to the reader.

Figure 33:
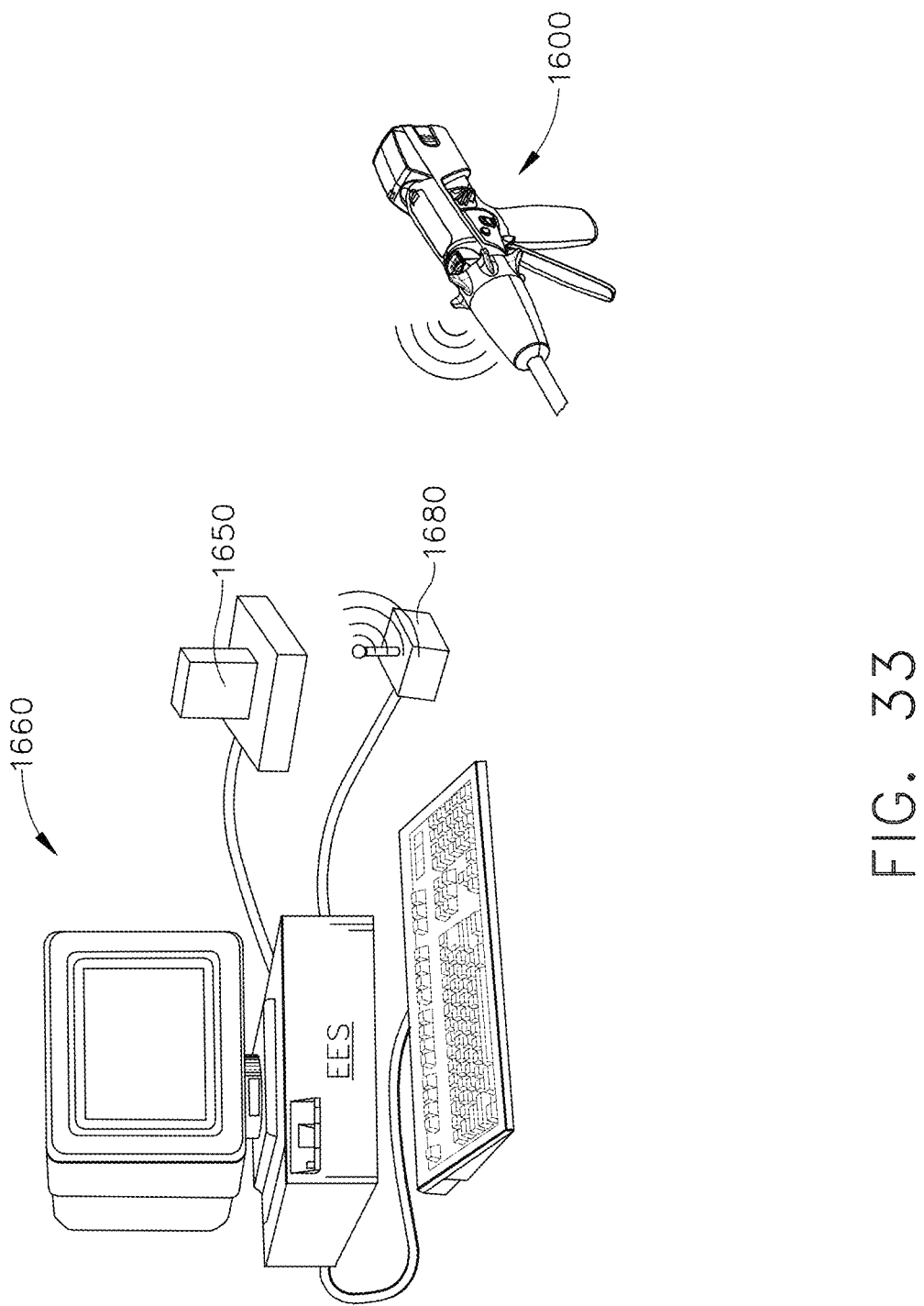
FIG. 33 is a schematic depicting a surgical system having wireless communication capabilities according to various embodiments of the present disclosure.

Referring now to FIG. 33, in various instances, a surgical system can comprise a surgical instrument 1600, which can be formed from a plurality of modular components. As described in greater detail herein, a handle component can be compatible with a plurality of different shaft components, for example, and the handle component and/or the shaft components can be reusable, for example. Moreover, a microcontroller of the surgical instrument 1600 can include a locking circuit, for example. In various instances, the locking circuit can prevent actuation of the surgical instrument until the locking circuit has been unlocked, for example. In various circumstances, the operator can enter a temporary access code into the surgical system to unlock the locking circuit of the microcontroller, for example.

In various circumstances, the operator can purchase or otherwise obtain the temporary access code for entering into the surgical system. For example, the instrument manufacturer or distributor can offer access codes for sale, and such access codes can be required in order to unlock, and thus use, the surgical instrument 1660. In various instances, the access code can unlock the locking circuit for a predefined period of time. The instrument manufacturer or distributor can offer different durations of use for purchase, and the user can select and purchase or acquire, a desired or preferable duration of use. For example, the user may acquire ten minutes of use, one hour of use, or one day of use. In other instances, additional and/or different suitable periods of use can be offered for sale or authorization. In various instances, after the acquired period of use expires, the locking circuit can be relocked. In other instances, an access code can unlock the locking circuit for a predefined number of surgical functions. For example, a user may purchase or otherwise obtain a single instrument firing or multiple firings, for example. Moreover, after the user has fired the instrument the purchased or authorized number of times, the locking circuit can be relocked. In still other instances, an access code can permanently unlock the locking circuit, for example.

In various instances, the operator can enter the temporary access code directly into the surgical system via a keypad or other suitable input arrangement. In other instances, the locking circuit can be unlocked by coupling a nonvolatile memory unit to the surgical instrument 1600, wherein the nonvolatile memory unit comprises a preprogrammed access code. In various instances, the nonvolatile memory unit can be loaded into a battery 1650 of the surgical instrument 1660, for example. Moreover, the nonvolatile memory unit can be reloaded and/or replaced. For example, the user can purchase replacement nonvolatile memory units. Additionally or alternatively, new codes can be purchased and uploaded to the nonvolatile memory unit, for example, after the previously-obtained access codes expire or lapse. In various instances, new codes can be loaded onto the nonvolatile memory unit when the battery 1650 is coupled to a power source and/or external computer 1670, for example.

In other instances, the temporary access code can be entered into an external or remote access code input, such as a display screen, computer, and/or heads up display. For example, a temporary access code can be purchased via a computer 1660, and can be transmitted to a radio frequency (RF) device 1680 coupled to the computer 1660. In various instances, the surgical instrument 1600 can comprise a receiver or antenna, which can be in signal communication with the radio frequency device 1680, for example. In such instances, the radio frequency device 1680 can transmit the acquired temporary access code(s) to the surgical instrument 1600 receiver, for example. Accordingly, the locking circuit can be unlocked, and the operator can use the surgical instrument 1600 for the purchased time period and/or number of surgical functions, for example.

In various instances, a modular surgical instrument may be compatible with an external display for depicting data and/or feedback from the surgical instrument. For example, the surgical instrument can comprise an instrument display for displaying feedback from the surgical procedure. In various instances, the instrument display can be positioned on the handle of the instrument, for example. In certain instances, the instrument display can depict a video feed viewed from an endoscope, for example. Additionally or alternatively, the display can detect sensed, measured, approximated, and/or calculated characteristics of the surgical instrument, surgical operation, and/or surgical site, for example. In various instances, it may be desirable to transmit the feedback to an external display. The external display can provide an enlarged view of the duplicated and/or reproduced feedback, for example, which can allow multiple operators and/or assistants to simultaneously view the feedback. In various instances, it may be desirable to select the surgical instrument for connection to the external display, for example, and, in other instances, the selection of a surgical instrument may be automatic.

Referring back to FIGS. 28A and 28B, the segmented circuit 1100 comprises an acceleration segment 1102 *c*. The acceleration segment comprises an accelerometer 1122. The accelerometer 1122 may be coupled to the safety processor 1104 and/or the primary processor 1106. The accelerometer 1122 is configured to monitor movement of the surgical instrument 2000. The accelerometer 1122 is configured to generate one or more signals indicative of movement in one or more directions. For example, in some embodiments, the accelerometer 1122 is configured to monitor movement of the surgical instrument 2000 in three directions. In other embodiments, the acceleration segment 1102 *c* comprises a plurality of accelerometers 1122, each configured to monitor movement in a signal direction.

In some embodiments, the accelerometer 1122 is configured to initiate a transition to and/or from a sleep mode, e.g., between sleep-mode and wake-up mode and vice versa. Sleep mode may comprise a low-power mode in which one or more of the circuit segments 1102 *a*-1102 *g* are deactivated or placed in a low-power state. For example, in one embodiment, the accelerometer 1122 remains active in sleep mode and the safety processor 1104 is placed into a low-power mode in which the safety processor 1104 monitors the accelerometer 1122, but otherwise does not perform any functions. The remaining circuit segments 1102 *b*-1102 *g* are powered off. In various embodiments, the primary processor 1104 and/or the safety processor 1106 are configured to monitor the accelerometer 1122 and transition the segmented circuit 1100 to sleep mode, for example, when no movement is detected within a predetermined time period. Although described in connection with the safety processor 1104 monitoring the accelerometer 1122, the sleep-mode/wake-up mode may be implemented by the safety processor 1104 monitoring any of the sensors, switches, or other indicators associated with the surgical instrument 2000 as described herein. For example, the safety processor 1104 may monitor an inertial sensor, or a one or more switches.

In some embodiments, the segmented circuit 1100 transitions to sleep mode after a predetermined period of inactivity. A timer is in signal communication with the safety processor 1104 and/or the primary processor 1106. The timer may be integral with the safety processor 1104, the primary processor 1106, and/or may be a separate circuit component. The timer is configured to monitor a time period since a last movement of the surgical instrument 2000 was detected by the accelerometer 1122. When the counter exceeds a predetermined threshold, the safety processor 1104 and/or the primary processor 1106 transitions the segmented circuit 1100 into sleep mode. In some embodiments, the timer is reset each time the accelerometer 1122 detects movement.

In some embodiments, all circuit segments except the accelerometer 1122, or other designated sensors and/or switches, and the safety processor 1104 are deactivated when in sleep mode. The safety processor 1104 monitors the accelerometer 1122, or other designated sensors and/or switches. When the accelerometer 1122 indicates movement of the surgical instrument 2000, the safety processor 1104 initiates a transition from sleep mode to operational mode. In operational mode, all of the circuit segments 1102 *a*-1102 *h* are fully energized and the surgical instrument 2000 is ready for use. In some embodiments, the safety processor 1104 transitions the segmented circuit 1100 to the operational mode by providing a signal to the primary processor 1106 to transition the primary processor 1106 from sleep mode to a full power mode. The primary processor 1106, then transitions each of the remaining circuit segments 1102 *d*-1102 *h* to operational mode.

The transition to and/or from sleep mode may comprise a plurality of stages. For example, in one embodiment, the segmented circuit 1100 transitions from the operational mode to the sleep mode in four stages. The first stage is initiated after the accelerometer 1122 has not detected movement of the surgical instrument for a first predetermined time period. After the first predetermined time period the segmented circuit 1100 dims a backlight of the display segment 1102 *d*. When no movement is detected within a second predetermined period, the safety processor 1104 transitions to a second stage, in which the backlight of the display segment 1102 *d* is turned off. When no movement is detected within a third predetermined time period, the safety processor 1104 transitions to a third stage, in which the polling rate of the accelerometer 1122 is reduced. When no movement is detected within a fourth predetermined time period, the display segment 1102 *d* is deactivated and the segmented circuit 1100 enters sleep mode. In sleep mode, all of the circuit segments except the accelerometer 1122 and the safety processor 1104 are deactivated. The safety processor 1104 enters a low-power mode in which the safety processor 1104 only polls the accelerometer 1122. The safety processor 1104 monitors the accelerometer 1122 until the accelerometer 1122 detects movement, at which point the safety processor 1104 transitions the segmented circuit 1100 from sleep mode to the operational mode.

In some embodiments, the safety processor 1104 transitions the segmented circuit 1100 to the operational mode only when the accelerometer 1122 detects movement of the surgical instrument 2000 above a predetermined threshold. By responding only to movement above a predetermined threshold, the safety processor 1104 prevents inadvertent transition of the segmented circuit 1100 to operational mode when the surgical instrument 2000 is bumped or moved while stored. In some embodiments, the accelerometer 1122 is configured to monitor movement in a plurality of directions. For example, the accelerometer 1122 may be configured to detect movement in a first direction and a second direction. The safety processor 1104 monitors the accelerometer 1122 and transitions the segmented circuit 1100 from sleep mode to operational mode when movement above a predetermined threshold is detected in both the first direction and the second direction. By requiring movement above a predetermined threshold in at least two directions, the safety processor 1104 is configured to prevent inadvertent transition of the segmented circuit 1100 from sleep mode due to incidental movement during storage.

In some embodiments, the accelerometer 1122 is configured to detect movement in a first direction, a second direction, and a third direction. The safety processor 1104 monitors the accelerometer 1122 and is configured to transition the segmented circuit 1100 from sleep mode only when the accelerometer 1122 detects oscillating movement in each of the first direction, second direction, and third direction. In some embodiments, oscillating movement in each of a first direction, a second direction, and a third direction correspond to movement of the surgical instrument 2000 by an operator and therefore transition to the operational mode is desirable when the accelerometer 1122 detects oscillating movement in three directions.

In some embodiments, as the time since the last movement detected increases, the predetermined threshold of movement required to transition the segmented circuit 1100 from sleep mode also increases. For example, in some embodiments, the timer continues to operate during sleep mode. As the timer count increases, the safety processor 1104 increases the predetermined threshold of movement required to transition the segmented circuit 1100 to operational mode. The safety processor 1104 may increase the predetermined threshold to an upper limit. For example, in some embodiments, the safety processor 1104 transitions the segmented circuit 1100 to sleep mode and resets the timer.

The predetermined threshold of movement is initially set to a low value, requiring only a minor movement of the surgical instrument 2000 to transition the segmented circuit 1100 from sleep mode. As the time since the transition to sleep mode, as measured by the timer, increases, the safety processor 1104 increases the predetermined threshold of movement. At a time T, the safety processor 1104 has increased the predetermined threshold to an upper limit. For all times T+, the predetermined threshold maintains a constant value of the upper limit.

In some embodiments, one or more additional and/or alternative sensors are used to transition the segmented circuit 1100 between sleep mode and operational mode. For example, in one embodiment, a touch sensor is located on the surgical instrument 2000. The touch sensor is coupled to the safety processor 1104 and/or the primary processor 1106. The touch sensor is configured to detect user contact with the surgical instrument 2000. For example, the touch sensor may be located on the handle of the surgical instrument 2000 to detect when an operator picks up the surgical instrument 2000. The safety processor 1104 transitions the segmented circuit 1100 to sleep mode after a predetermined period has passed without the accelerometer 1122 detecting movement. The safety processor 1104 monitors the touch sensor and transitions the segmented circuit 1100 to operational mode when the touch sensor detects user contact with the surgical instrument 2000. The touch sensor may comprise, for example, a capacitive touch sensor, a temperature sensor, and/or any other suitable touch sensor. In some embodiments, the touch sensor and the accelerometer 1122 may be used to transition the device between sleep mode and operation mode. For example, the safety processor 1104 may only transition the device to sleep mode when the accelerometer 1122 has not detected movement within a predetermined period and the touch sensor does not indicate a user is in contact with the surgical instrument 2000. Those skilled in the art will recognize that one or more additional sensors may be used to transition the segmented circuit 1100 between sleep mode and operational mode. In some embodiments, the touch sensor is only monitored by the safety processor 1104 when the segmented circuit 1100 is in sleep mode.

In some embodiments, the safety processor 1104 is configured to transition the segmented circuit 1100 from sleep mode to the operational mode when one or more handle controls are actuated. After transitioning to sleep mode, such as, for example, after the accelerometer 1122 has not detected movement for a predetermined period, the safety processor 1104 monitors one or more handle controls, such as, for example, the plurality of articulation switches 1158 a-1164 b. In other embodiments, the one or more handle controls comprise, for example, a clamp control 1166, a release button 1168, and/or any other suitable handle control. An operator of the surgical instrument 2000 may actuate one or more of the handle controls to transition the segmented circuit 1100 to operational mode. When the safety processor 1104 detects the actuation of a handle control, the safety processor 1104 initiates the transition of the segmented circuit 1100 to operational mode. Because the primary processor 1106 is in not active when the handle control is actuated, the operator can actuate the handle control without causing a corresponding action of the surgical instrument 2000.

Figure 38:
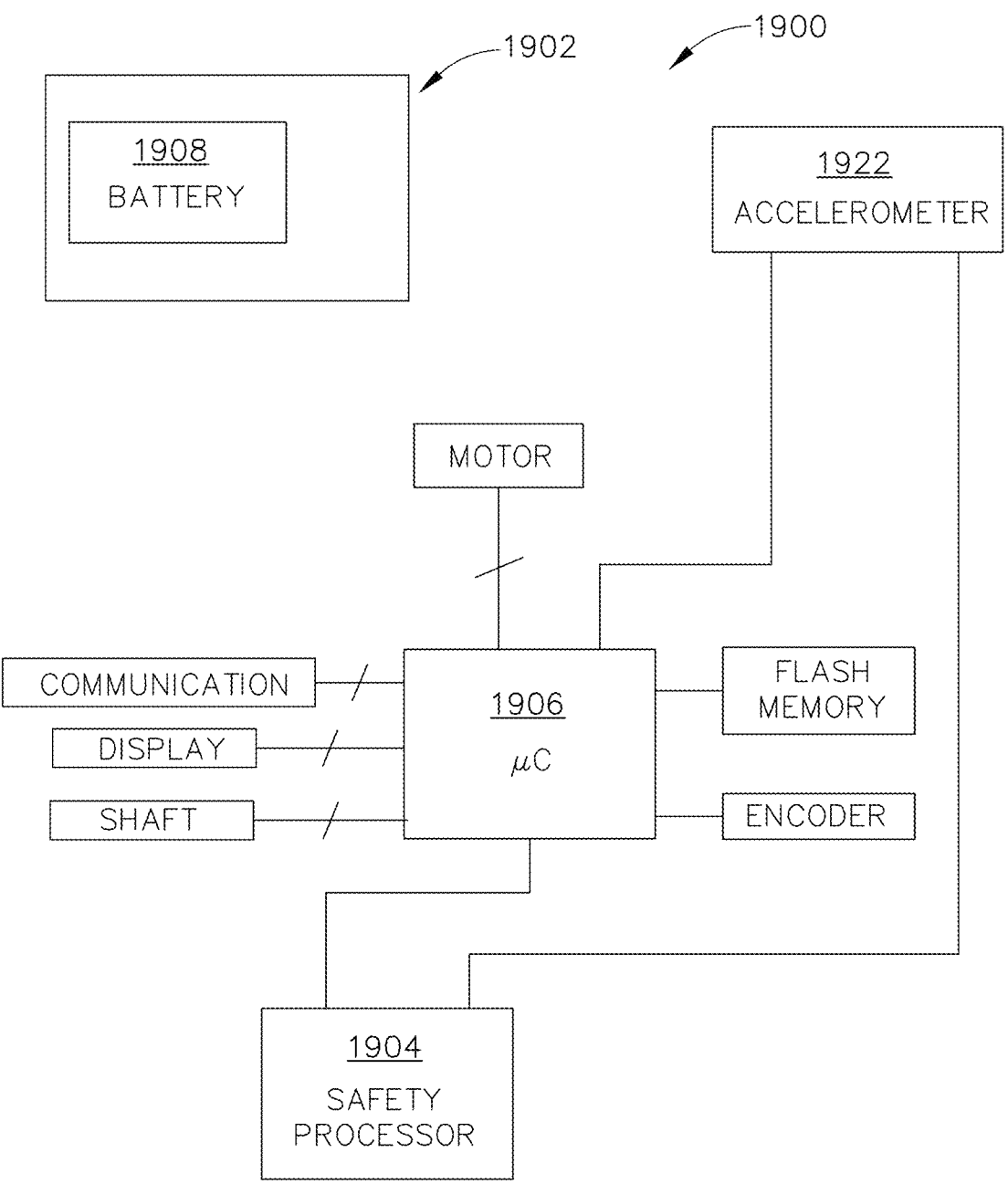
FIG. 38 illustrates one embodiment of a segmented circuit comprising an accelerometer.

FIG. 38 illustrates one embodiment of a segmented circuit 1900 comprising an accelerometer 1922 configured to monitor movement of a surgical instrument, such as, for example, the surgical instrument 2000 illustrated in FIGS. 1-3B. A power segment 1902 provides power from a battery 1908 to one or more circuit segments, such as, for example, the accelerometer 1922. The accelerometer 1922 is coupled to a processor 1906. The accelerometer 1922 is configured to monitor movement the surgical instrument 2000. The accelerometer 1922 is configured to generate one or more signals indicative of movement in one or more directions. For example, in some embodiments, the accelerometer 1922 is configured to monitor movement of the surgical instrument 2000 in three directions.

In certain instances, the processor 1906 may be an LM 4F230H5QR, available from Texas Instruments, for example. The processor 1906 is configured to monitor the accelerometer 1922 and transition the segmented circuit 1900 to sleep mode, for example, when no movement is detected within a predetermined time period. In some embodiments, the segmented circuit 1900 transitions to sleep mode after a predetermined period of inactivity. For example, a safety processor 1904 may transitions the segmented circuit 1900 to sleep mode after a predetermined period has passed without the accelerometer 1922 detecting movement. In certain instances, the accelerometer 1922 may be an LIS331DLM, available from STMicroelectronics, for example. A timer is in signal communication with the processor 1906. The timer may be integral with the processor 1906 and/or may be a separate circuit component. The timer is configured to count time since a last movement of the surgical instrument 2000 was detected by the accelerometer 1922. When the counter exceeds a predetermined threshold, the processor 1906 transitions the segmented circuit 1900 into sleep mode. In some embodiments, the timer is reset each time the accelerometer 1922 detects movement.

In some embodiments, the accelerometer 1922 is configured to detect an impact event. For example, when a surgical instrument 2000 is dropped, the accelerometer 1922 will detect acceleration due to gravity in a first direction and then a change in acceleration in a second direction (caused by impact with a floor and/or other surface). As another example, when the surgical instrument 2000 impacts a wall, the accelerometer 1922 will detect a spike in acceleration in one or more directions. When the accelerometer 1922 detects an impact event, the processor 1906 may prevent operation of the surgical instrument 2000, as impact events can loosen mechanical and/or electrical components. In some embodiments, only impacts above a predetermined threshold prevent operation. In other embodiments, all impacts are monitored and cumulative impacts above a predetermined threshold may prevent operation of the surgical instrument 2000.

With reference back to FIGS. 28A and 28B, in one embodiment, the segmented circuit 1100 comprises a power segment 1102 h. The power segment 1102 h is configured to provide a segment voltage to each of the circuit segments 1102 a-1102 g. The power segment 1102 h comprises a battery 1108. The battery 1108 is configured to provide a predetermined voltage, such as, for example, 12 volts through battery connector 1110. One or more power converters 1114 a, 1114 b, 1116 are coupled to the battery 1108 to provide a specific voltage. For example, in the illustrated embodiments, the power segment 1102 h comprises an axillary switching converter 1114 a, a switching converter 1114 b, and a low-drop out (LDO) converter 1116. The switch converters 1114 a, 1114 b are configured to provide 3.3 volts to one or more circuit components. The LDO converter 1116 is configured to provide 5.0 volts to one or more circuit components. In some embodiments, the power segment 1102 *h* comprises a boost converter 1118. A transistor switch (e.g., N-Channel MOSFET) 1115 is coupled to the power converters 1114 *b*, 1116. The boost converter 1118 is configured to provide an increased voltage above the voltage provided by the battery 1108, such as, for example, 13 volts. The boost converter 1118 may comprise, for example, a capacitor, an inductor, a battery, a rechargeable battery, and/or any other suitable boost converter for providing an increased voltage. The boost converter 1118 provides a boosted voltage to prevent brownouts and/or low-power conditions of one or more circuit segments 1102 *a*-1102 *g* during power-intensive operations of the surgical instrument 2000. The embodiments, however, are not limited to the voltage range(s) described in the context of this specification.

Figure 37:
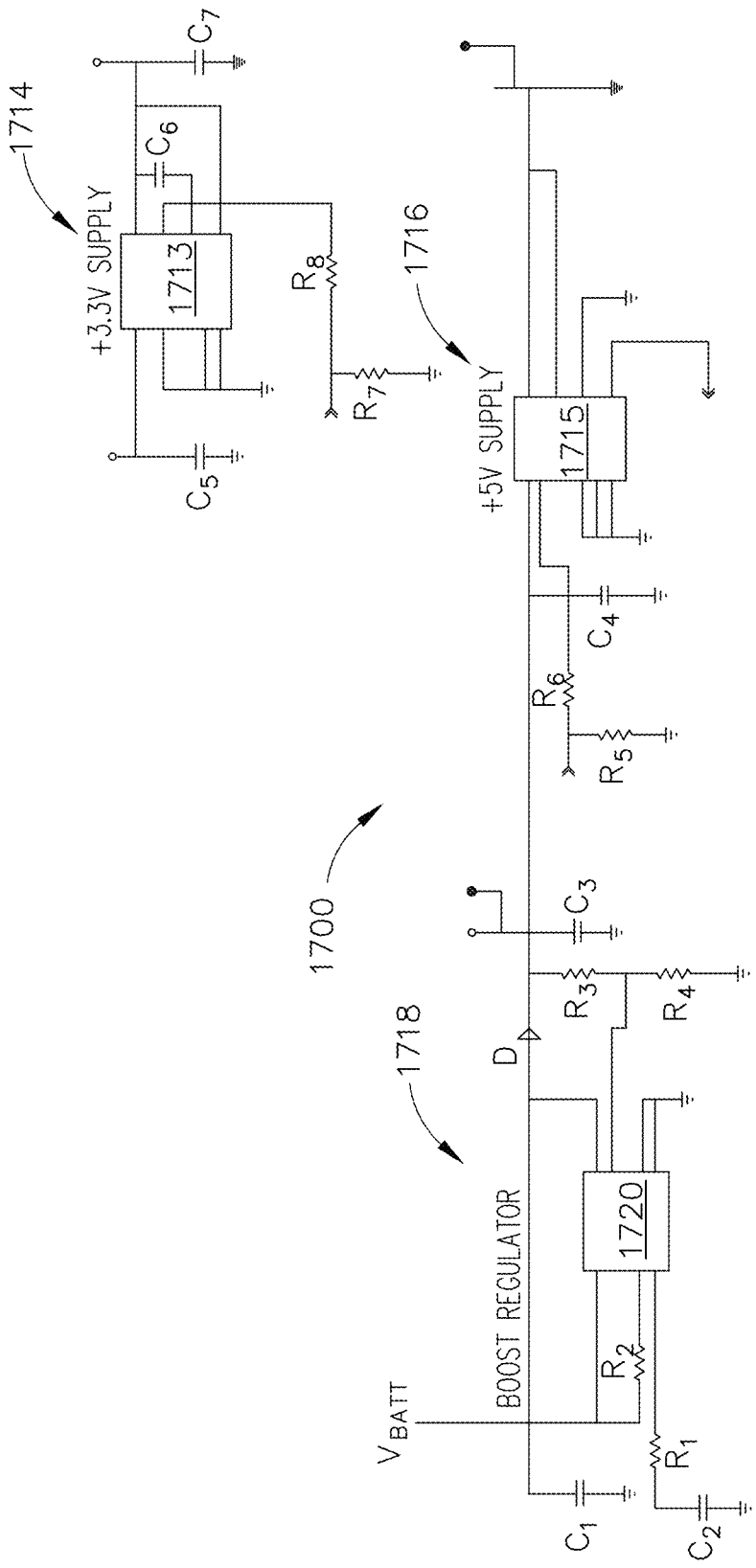
FIG. 37 illustrates one embodiment of a power system comprising a plurality of daisy chained power converters configured to be sequentially energized.

FIG. 37 illustrates one embodiment of a power system 1700 comprising a plurality of daisy chained power converters 1714, 1716, 1718 configured to be sequentially energized. The plurality of daisy chained power converters 1714, 1716, 1718 may be sequentially activated by, for example, a safety processor during initial power-up and/or transition from sleep mode. The safety processor may be powered by an independent power converter (not shown). For example, in one embodiment, when a battery voltage VBATT is coupled to the power system 1700 and/or an accelerometer detects movement in sleep mode, the safety processor initiates a sequential start-up of the daisy chained power converters 1714, 1716, 1718. The safety processor activates the 13V boost section 1718. The boost section 1718 is energized and performs a self-check. In some embodiments, the boost section 1718 comprises an integrated circuit 1720 configured to boost the source voltage and to perform a self check. A diode D prevents power-up of a 5V supply section 1716 until the boost section 1718 has completed a self-check and provided a signal to the diode D indicating that the boost section 1718 did not identify any errors. In some embodiments, this signal is provided by the safety processor. The embodiments, however, are not limited to the particular voltage range(s) described in the context of this specification.

The 5V supply section 1716 is sequentially powered-up after the boost section 1718. The 5V supply section 1716 performs a self-check during power-up to identify any errors in the 5V supply section 1716. The 5V supply section 1716 comprises an integrated circuit 1715 configured to provide a step-down voltage from the boost voltage and to perform an error check. When no errors are detected, the 5V supply section 1716 completes sequential power-up and provides an activation signal to the 3.3V supply section 1714. In some embodiments, the safety processor provides an activation signal to the 3.3V supply section 1714. The 3.3V supply section comprises an integrated circuit 1713 configured to provide a step-down voltage from the 5V supply section 1716 and perform a self-error check during power-up. When no errors are detected during the self-check, the 3.3V supply section 1714 provides power to the primary processor. The primary processor is configured to sequentially energize each of the remaining circuit segments. By sequentially energizing the power system 1700 and/or the remainder of a segmented circuit, the power system 1700 reduces error risks, allows for stabilization of voltage levels before loads are applied, and prevents large current draws from all hardware being turned on simultaneously in an uncontrolled manner. The embodiments, however, are not limited to the particular voltage range(s) described in the context of this specification.

In one embodiment, the power system 1700 comprises an over voltage identification and mitigation circuit. The over voltage identification and mitigation circuit is configured to detect a monopolar return current in the surgical instrument and interrupt power from the power segment when the monopolar return current is detected. The over voltage identification and mitigation circuit is configured to identify ground floatation of the power system. The over voltage identification and mitigation circuit comprises a metal oxide varistor. The over voltage identification and mitigation circuit comprises at least one transient voltage suppression diode.

Figure 39:
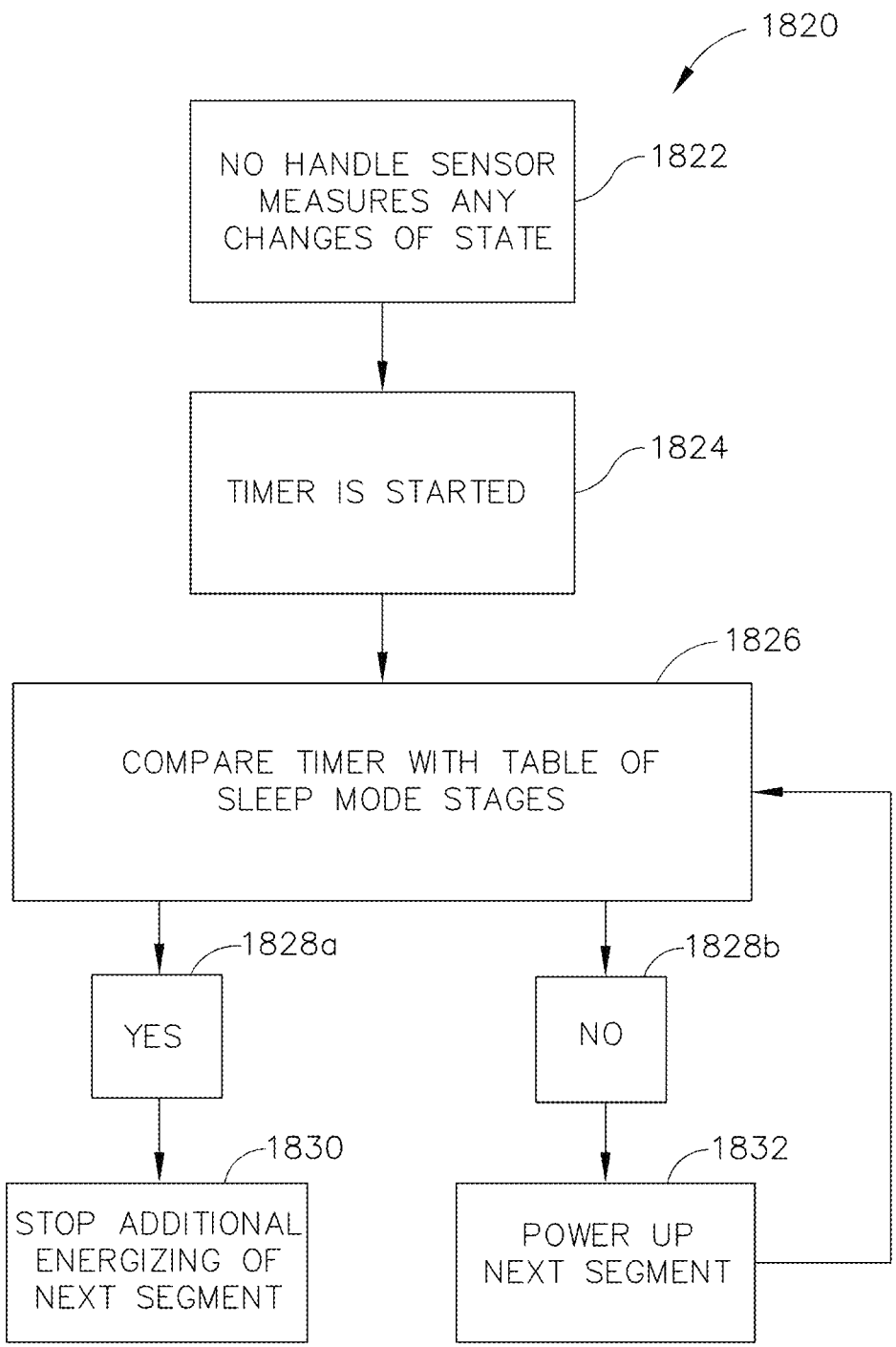
FIG. 39 illustrates one embodiment of a process for sequential start-up of a segmented circuit.

FIG. 39 illustrates one embodiment of a process for sequential start-up of a segmented circuit, such as, for example, the segmented circuit 1100 illustrated in FIGS. 5A and 5B. The sequential start-up process 1820 begins when one or more sensors initiate a transition from sleep mode to operational mode. When the one or more sensors stop detecting state changes 1822, a timer is started 1824. The timer counts the time since the last movement/interaction with the surgical instrument 2000 was detected by the one or more sensors. The timer count is compared 1826 to a table of sleep mode stages by, for example, the safety processor 1104. When the timer count exceeds one or more counts for transition to a sleep mode stage 1828 *a*, the safety processor 1104 stops energizing 1830 the segmented circuit 1100 and transitions the segmented circuit 1100 to the corresponding sleep mode stage. When the timer count is below the threshold for any of the sleep mode stages 1828 *b*, the segmented circuit 1100 continues to sequentially energize the next circuit segment 1832.

Figure 34:
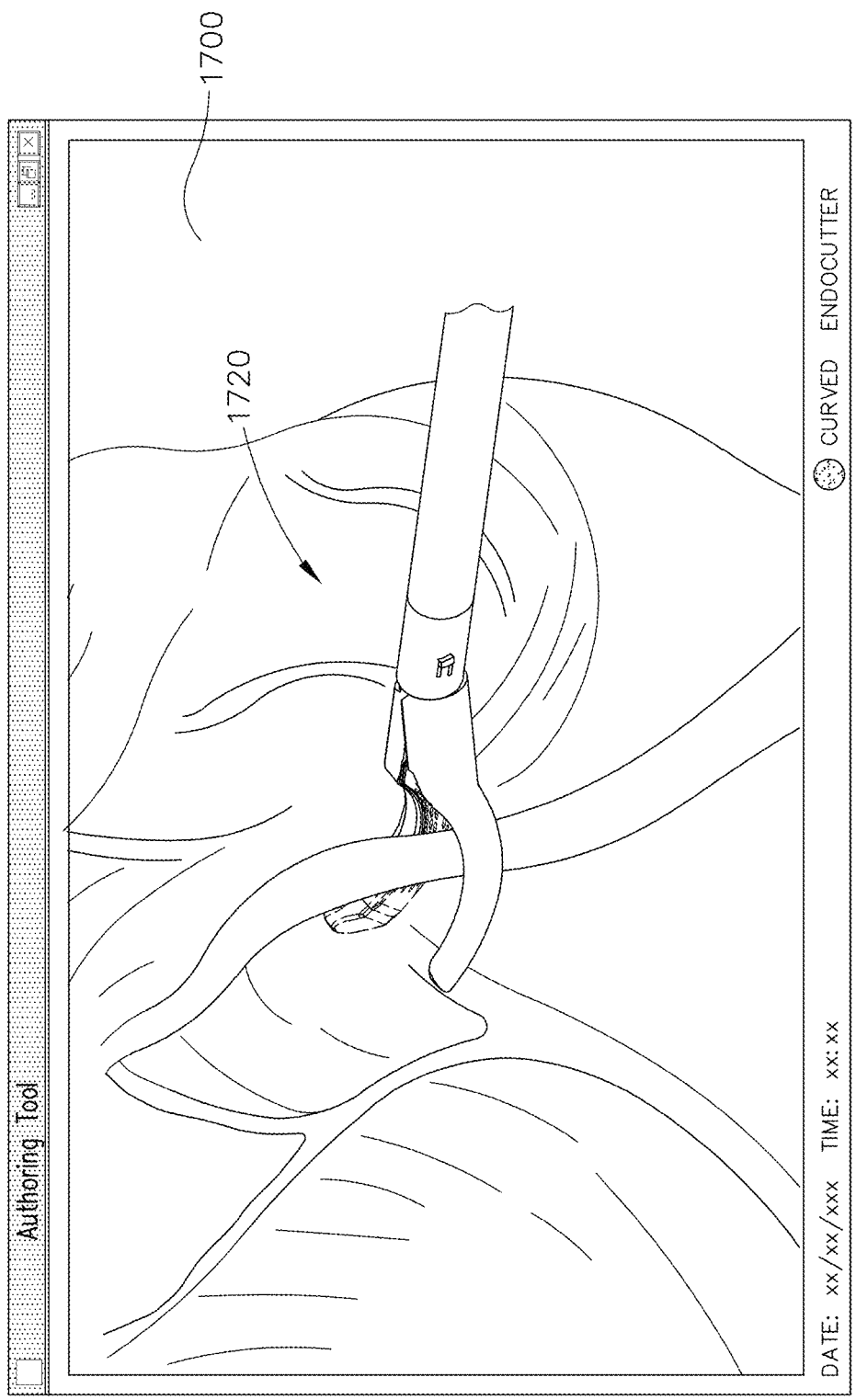
FIG. 34 is an elevation view of an external screen depicting an end effector at a surgical site according to various embodiments of the present disclosure.

Referring to FIG. 34, an external display 1700 can depict an end effector 1720 of a surgical instrument and/or the surgical site, for example. The external display 1700 can also depict feedback and/or data sensed and/or measured by the surgical instrument, for example. In various instances, the external display 1700 can duplicate feedback provided on the display of the surgical instrument. In certain circumstances, the surgical instrument can automatically connect with the external display 1700 and/or a wireless receiver in signal communication with the external, or operating room, display 1700, for example. In such instances, an operator can be notified if multiple surgical instruments are attempting to connect to the external display 1700. As described herein, the operator can select the desired surgical instrument(s) from a menu on the external display 1700, for example. In still other instances, the operator can select the desired surgical instrument by providing an input to the surgical instrument. For example, the operator can issue a command, control sequence, or input a code to select the surgical instrument. In various instances, the operator may complete a specific control sequence with the surgical instrument to select that surgical instrument. For example, the operator may power on the surgical instrument and, within a predefined period of time, hold down the reverse button for a predefined period of time, for example, to select the surgical instrument. When an instrument is selected, the feedback on the selected instrument display can be rebroadcast or duplicated on the external display 1700, for example.

Figure 35:
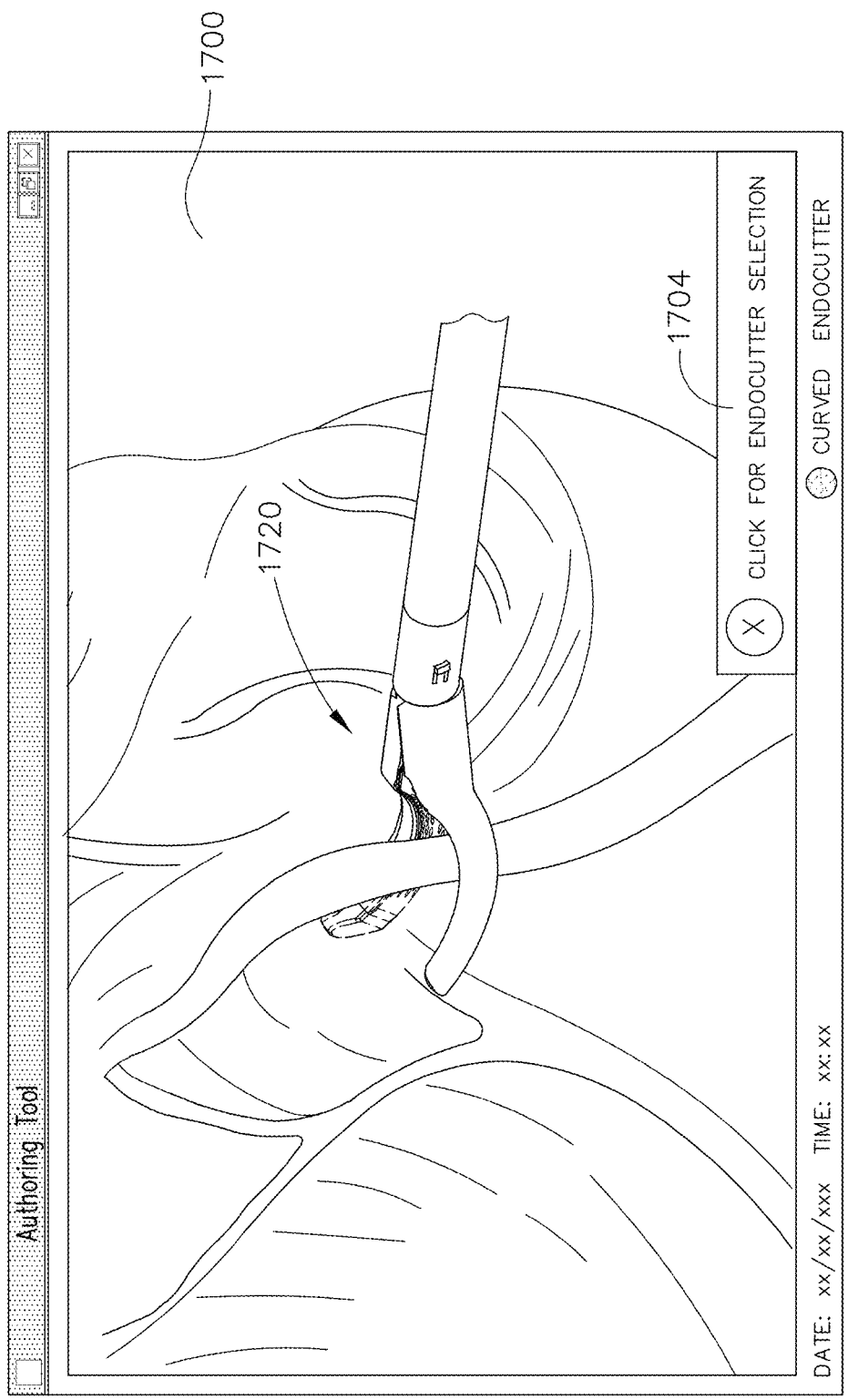
FIG. 35 is an elevation view of the external screen of FIG. 34 depicting a notification according to various embodiments of the present disclosure.
Figure 36:
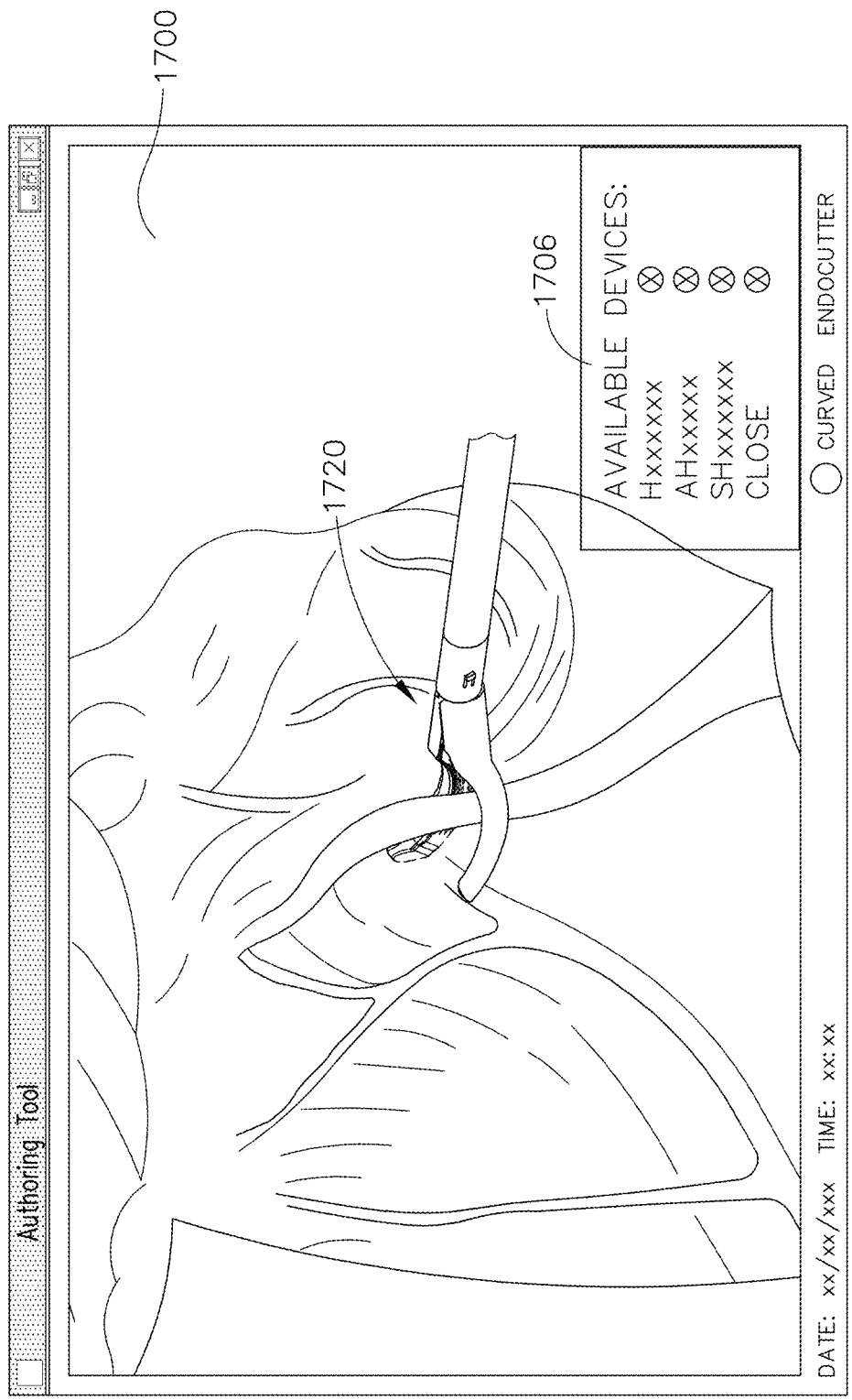
FIG. 36 is an elevation view of the external screen of FIG. 34 depicting a selection menu according to various embodiments of the present disclosure.

In certain instances, the surgical system can include a proximity sensor. For example, the external display and/or wireless receiver can comprise a proximity sensor, which can detect when a surgical instrument is brought within a predefined range thereof. Referring primarily to FIGS. 35 and 36, when the display 1700 and/or wireless receiver detect a surgical instrument, the display can notify the user. In certain circumstances, the display and/or wireless receiver may detect multiple surgical instruments. Referring to FIG. 35, the display 1700 can include a non-obtrusive notification 1704, for example, which can communicate to the user that a surgical instrument, or multiple surgical instruments, have been detected in the proximity of the display 1700. Accordingly, using the controls for the display 1700, such as a computer, for example, the user can click the notification 1704 to open the menu 1706 of instrument selections (FIG. 36). The menu 1706 can depict the available surgical instruments, for example, and the user can select the preferred surgical instrument for broadcasting on the display 1700. For example, the menu 1706 can depict the serial numbers and/or names of the available surgical instruments.

In certain instances, the selected surgical instrument can provide feedback to the operator to confirm its selection. For example, the selected surgical instrument can provide auditory or haptic feedback, for example. Additionally, the selected surgical instrument can broadcast at least a portion of its feedback to the external display 1700. In certain instances, the operator can select multiple surgical instruments and the display 1700 can be shared by the selected surgical instruments. Additionally or alternatively, the operating room can include multiple displays and at least one surgical instrument can be selected for each display, for example. Various surgical system features and/or components are further described in U.S. patent application Ser. No. 13/974,166, filed Aug. 23, 2013, and titled FIRING MEMBER RETRACTION DEVICES FOR POWERED SURGICAL INSTRUMENTS, now U.S. Pat. No. 9,700,310, which is hereby incorporated by reference in its entirety.

The entire disclosures of:

- U.S. Pat. No. 5,403,312, entitled ELECTROSURGICAL HEMOSTATIC DEVICE, which issued on Apr. 4, 1995;
- U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
- U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
- U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
- U.S. Pat. No. 7,670,334, entitled SURGICAL INSTRUMENT HAVING AN ARTICULATING END EFFECTOR, which issued on Mar. 2, 2010;
- U.S. Pat. No. 7,753,245, entitled SURGICAL STAPLING INSTRUMENTS, which issued on Jul. 13, 2010;
- U.S. Pat. No. 8,393,514, entitled SELECTIVELY ORIENTABLE IMPLANTABLE FASTENER CARTRIDGE, which issued on Mar. 12, 2013;
- U.S. patent application Ser. No. 11/343,803, entitled SURGICAL INSTRUMENT HAVING RECORDING CAPABILITIES, now U.S. Pat. No. 7,845,537;
- U.S. patent application Ser. No. 12/031,573, entitled SURGICAL CUTTING AND FASTENING INSTRUMENT HAVING RF ELECTRODES, filed Feb. 14, 2008;
- U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
- U.S. patent application Ser. No. 12/235,782, entitled MOTOR-DRIVEN SURGICAL CUTTING INSTRUMENT, now U.S. Pat. No. 8,210,411;
- U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
- U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;
- U.S. patent application Ser. No. 12/893,461, entitled STAPLE CARTRIDGE, filed Sep. 29, 2012, now U.S. Pat. No. 8,733,613;
- U.S. patent application Ser. No. 13/036,647, entitled SURGICAL STAPLING INSTRUMENT, filed Feb. 28, 2011, now U.S. Pat. No. 8,561,870;
- U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
- U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;
- U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;
- U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;
- U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and
- U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

In accordance with various embodiments, the surgical instruments described herein may comprise one or more processors (e.g., microprocessor, microcontroller) coupled to various sensors. In addition, to the processor(s), a storage (having operating logic) and communication interface, are coupled to each other.

As described earlier, the sensors may be configured to detect and collect data associated with the surgical device. The processor processes the sensor data received from the sensor(s).

The processor may be configured to execute the operating logic. The processor may be any one of a number of single or multi-core processors known in the art. The storage may comprise volatile and non-volatile storage media configured to store persistent and temporal (working) copy of the operating logic.

In various embodiments, the operating logic may be configured to process the collected biometric associated with motion data of the user, as described above. In various embodiments, the operating logic may be configured to perform the initial processing, and transmit the data to the computer hosting the application to determine and generate instructions. For these embodiments, the operating logic may be further configured to receive information from and provide feedback to a hosting computer. In alternate embodiments, the operating logic may be configured to assume a larger role in receiving information and determining the feedback. In either case, whether determined on its own or responsive to instructions from a hosting computer, the operating logic may be further configured to control and provide feedback to the user.

In various embodiments, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other embodiments, the operating logic may be implemented in hardware such as a gate array.

In various embodiments, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various embodiments, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various embodiments, the processor may be packaged together with the operating logic. In various embodiments, the processor may be packaged together with the operating logic to form a System in Package (SiP). In various embodiments, the processor may be integrated on the same die with the operating logic. In various embodiments, the processor may be packaged together with the operating logic to form a System on Chip (SoC).

Various embodiments may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application program interfaces (APIs), and so forth. The firmware may be stored in a memory of the processor 3008 which may comprise a nonvolatile memory (NVM), such as in bit-masked read-only memory (ROM) or flash memory. In various implementations, storing the firmware in ROM may preserve flash memory. The nonvolatile memory (NVM) may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A surgical instrument for use by an operator in a surgical procedure, said surgical instrument comprising:
   a handle assembly movable between a plurality of positions, said handle assembly comprising an interface;
   an elongate shaft;
   an end effector extending distally from said elongate shaft;
   and a control system, comprising:
      a processor; and
      a memory coupled to said processor to store program instructions, which when executed from said memory cause said processor to toggle between a plurality of interface configurations, wherein each of said interface configurations is associated with one of said positions.

2. The surgical instrument of claim 1, wherein said plurality of interface configurations comprise a first interface configuration and a second interface configuration, wherein said plurality of positions comprise a first position and a second position, and wherein said program instructions, when executed from said memory, cause said processor to adopt said first interface configuration while said handle assembly is in said first position, and adopt said second interface configuration while said handle assembly is in said second position.

3. The surgical instrument of claim 2, further comprising a screen, wherein said first interface configuration comprises a first orientation of said screen, and wherein said second interface configuration comprises a second orientation of said screen which is different from said first orientation.

4. The surgical instrument of claim 2, wherein said interface includes a first switch and a second switch, said first and second switches are operable by the operator to articulate said end effector relative to said elongate shaft.

5. The surgical instrument of claim 4, wherein said first switch is operable by the operator to articulate said end effector in a first direction when said processor is generating said first interface configuration, and wherein said first switch is operable by the operator to articulate said end effector in a second direction, different from said first direction, when said processor is generating said second interface configuration.

6. The surgical instrument of claim 5, wherein said second switch is operable by the operator to articulate said end effector in said second direction when said processor is generating said first interface configuration, and wherein said second switch is operable by the operator to articulate said end effector in said first direction when said processor is generating said second interface configuration.

7. A surgical instrument for use by an operator in a surgical procedure, said surgical instrument comprising:
   an interface comprising a plurality of operational controls;
   an elongate shaft;
   an end effector extending distally from said elongate shaft; and
   a control system, comprising:
      a processor; and
      a memory coupled to said processor to store program instructions, which when executed from said memory cause said processor to toggle said interface between a primary interface configuration and a secondary interface configuration, wherein said plurality of operational controls are configured to perform operational functions while said interface is in said primary interface configuration, wherein said plurality of operational controls are configured to perform navigational functions while said interface is in said secondary interface configuration, wherein said navigational functions are related to said operational functions.

8. The surgical instrument of claim 7, wherein said interface comprises a display.

9. The surgical instrument of claim 8 further comprising a navigational menu accessible through said display while said interface is in said secondary interface configuration.

10. The surgical instrument of claim 9, wherein said navigational menu comprises an articulation menu, wherein said plurality of operational controls comprise an articulation control, wherein said articulation control is operable to articulate said end effector relative to said elongate shaft in said primary interface configuration, and wherein said articulation control is operable to access said articulation menu in said secondary interface configuration.

11. A surgical instrument for use by an operator in a surgical procedure, said surgical instrument comprising:
   an elongate shaft;
   an end effector extending distally from said elongate shaft, said end effector comprising a staple cartridge, said staple cartridge including a plurality of staples movable between an unfired configuration and a fired configuration;
   a firing mechanism configured to move said plurality of staples to said fired configuration;
   an interface comprising a touchscreen, wherein said touchscreen comprises a firing icon; and
   a control system, comprising:
      a processor; and
      a memory coupled to said processor to store program instructions, which when executed from said memory cause said processor to detect a firing input signal generated when the operator selects said firing icon, wherein said program instructions, when executed from said memory, cause said processor to respond to said detection of said firing input signal by activating said firing mechanism to move said plurality of staples to said fired configuration.

12. The surgical instrument of claim 11 further comprising an articulation mechanism configured to articulate said end effector relative to said elongate shaft, wherein said touch screen comprises an articulation icon, wherein said program instructions, when executed from said memory, cause said processor to detect an articulation input signal generated when the operator selects said articulation icon, and wherein said program instructions, when executed from said memory, cause said processor to respond to said articulation input signal by activating said articulation mechanism to articulate said end effector.

13. A surgical assembly, comprising,
   a surgical instrument for use by an operator in a surgical procedure, said surgical instrument comprising:
      a handle assembly comprising a primary interface, said primary interface comprising a plurality of primary controls;

an elongate shaft extending distally from said handle assembly; and an end effector extending distally from said elongate shaft, wherein said plurality of primary controls are manually operable to actuate said end effector; and a remote operating unit comprising a secondary interface, said secondary interface comprising a plurality of secondary controls, wherein said plurality of secondary controls are operable to remotely actuate said end effector.

14. The surgical assembly of claim 13, wherein said plurality of primary controls are actuatable to generate primary control signals, wherein said plurality of secondary controls are actuatable to generate secondary control signals, and wherein said secondary control signals are configured to mimic said primary control signals.

15. The surgical assembly of claim 14, wherein said surgical instrument comprises a receiver, wherein said remote operating unit comprises a transmitter configured to transmit said secondary control signals to said receiver.

16. The surgical assembly of claim 14, wherein said surgical instrument comprises a controller, said controller comprising:

a processor configured to receive said primary control signals and said secondary control signals; and a memory coupled to said processor to store program instructions, which when executed from said memory cause said processor to actuate said end effector in response to at least one of said primary control signals and said secondary control signals.

\* \* \* \* \*